US009035777B2

(12) United States Patent
Bangera et al.

(10) Patent No.: US 9,035,777 B2
(45) Date of Patent: May 19, 2015

(54) COMPUTATIONAL SYSTEMS AND METHODS FOR MONITORING MEDICATION EVENTS INCLUDING USE OF A CAMERA AND DATA COMPARISON

(75) Inventors: Mahalaxmi Gita Bangera, Renton, WA (US); Roderick A. Hyde, Redmond, WA (US); Jordin T. Kare, San Jose, CA (US); Eric C. Leuthardt, St. Louis, MO (US); Elizabeth A. Sweeney, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 411 days.

(21) Appl. No.: 13/593,917

(22) Filed: Aug. 24, 2012

(65) Prior Publication Data
US 2014/0055589 A1 Feb. 27, 2014

(51) Int. Cl.
G08B 21/00 (2006.01)
G06F 19/00 (2011.01)
A61B 5/00 (2006.01)

(52) U.S. Cl.
CPC .......... *G06F 19/3418* (2013.01); *A61B 5/6898* (2013.01); *A61B 5/0022* (2013.01); *A61B 5/0077* (2013.01); *A61B 5/4833* (2013.01); *A61B 5/4848* (2013.01); *G06F 19/3456* (2013.01); *A61B 2562/0204* (2013.01); *A61B 2576/00* (2013.01)

(58) Field of Classification Search
USPC ............. 340/573.1, 539.12, 309.16; 600/300; 368/10; 705/2; 348/77
See application file for complete search history.

(56) References Cited

U.S. PATENT DOCUMENTS

| 6,097,295 | A  | 8/2000  | Griesinger et al. |
|-----------|----|---------|-------------------|
| 6,150,942 | A  | 11/2000 | O'Brien           |
| 6,841,391 | B2 | 1/2005  | Lewis et al.      |
| 7,226,164 | B2 | 6/2007  | Abourizk et al.   |
| 7,245,956 | B2 | 7/2007  | Matthews et al.   |
| 7,261,857 | B2 | 8/2007  | Suslick et al.    |

(Continued)

FOREIGN PATENT DOCUMENTS

| WO | WO 03/048789 A2  | 6/2003  |
|----|------------------|---------|
| WO | WO 2007/136523 A2 | 11/2007 |

OTHER PUBLICATIONS

Azevedo et al.; "Micropower Impulse Radar"; Science & Technology Review; Jan./Feb. 1996; pp. 17-29.

(Continued)

*Primary Examiner* — Jeffery Hofsass

(57) ABSTRACT

Computer-based systems and computer-implemented methods are described for monitoring medication events for an individual. Computer-based systems include systems for monitoring medication events relating to an individual, including: circuitry for analyzing data for an identifier of a first medication event for an individual; circuitry for analyzing the data for at least one attribute of an individual; circuitry for analyzing the data for at least one attribute relating to a medication during the first medication event; circuitry for analyzing the data for at least one feature of visual information and at least one feature of non-visual information relating to the individual during the first medication event; circuitry for analyzing the received data for a time associated with the first medication event; circuitry for determining a compliance likelihood for the first medication event based on the analyses of the received data; and circuitry for indicating the determined compliance likelihood.

37 Claims, 102 Drawing Sheets

(56) References Cited

U.S. PATENT DOCUMENTS

| | | |
|---|---|---|
| 7,272,431 B2 | 9/2007 | McGrath |
| 7,330,101 B2 | 2/2008 | Sekura |
| 7,340,503 B2 | 3/2008 | Washburn |
| 7,616,111 B2 | 11/2009 | Covannon et al. |
| 7,639,120 B2 | 12/2009 | Sekura |
| 7,782,189 B2 | 8/2010 | Spoonhower et al. |
| 7,811,234 B2 | 10/2010 | McGrath |
| 7,944,342 B2 | 5/2011 | Sekura |
| 7,945,461 B2 | 5/2011 | Sekura |
| 7,956,727 B2 | 6/2011 | Loncar |
| 8,060,249 B2 | 11/2011 | Bear et al. |
| 2004/0123667 A1 | 7/2004 | McGrath |
| 2004/0249257 A1 | 12/2004 | Tupin, Jr. et al. |
| 2004/0249258 A1 | 12/2004 | Tupin, Jr. et al. |
| 2005/0041531 A1 | 2/2005 | Sekura |
| 2006/0055392 A1 | 3/2006 | Passmore et al. |
| 2006/0058694 A1 | 3/2006 | Clark et al. |
| 2007/0048180 A1 | 3/2007 | Gabriel et al. |
| 2007/0048181 A1 | 3/2007 | Chang et al. |
| 2008/0045832 A1 | 2/2008 | McGrath |
| 2008/0050839 A1 | 2/2008 | Suslick et al. |
| 2008/0281630 A1 | 11/2008 | Sekura |
| 2009/0227882 A1 | 9/2009 | Foo |
| 2010/0042430 A1 | 2/2010 | Bartfeld |
| 2010/0166604 A1 | 7/2010 | Lim et al. |
| 2010/0219097 A1 | 9/2010 | Ramasubramanian et al. |
| 2010/0283601 A1 | 11/2010 | Tai et al. |
| 2011/0295127 A1 | 12/2011 | Sandler et al. |

OTHER PUBLICATIONS

Culhane et al.; "Accelerometers in rehabilitation medicine for older adults"; Age and Aging; bearing a date of 2005; pp. 556-560; vol. 34; Oxford University Press.

De Oliveira et al.; "Exploring Persuasive Techniques for Medication Compliance"; Apr. 11, 2010; pp. 1-4; WISH 2010; ACM 978-1-60558-246—Jul. 9, 2004; Atlanta, Georgia, USA.

Galloway et al.; "A Simple, Novel Method for Assessing Medication Adherence: Capsule Photographs Taken With Cellular Telephones"; J Addict Med; Sep. 2011; pp. 170-174; vol. 5, No. 3; American Society of Addiction Medicine.

Harland et al.; "Electric potential probes—new directions in the remote sensing of the human body"; Measurement Science and Technology; bearing a date of 2002; pp. 163-169; vol. 13; Institute of Physics Publishing Ltd.

Harland et al.; "High resolution ambulatory electrocardiographic monitoring using wrist-mounted electric potential sensors"; Measurement Science and Technology; bearing a date of 2003; pp. 923-928; vol. 14; Institute of Physics Publishing Ltd.

Karlen et al.; "The Phone Oximeter"; EMBC Unconference 2011; bearing a date of Jul. 22, 2011; one page; Electrical and Computer Engineering in Medicine, The University of British Columbia, Vancouver, Canada.

Kuzmych et al.; "Carbon nanotube sensors for exhaled breath components"; Nanotechnology; bearing a date of 2007; pp. 1-7; vol. 18; Institute of Physics Publishing Ltd.

Prance et al.; "Adaptive Electric Potential Sensors for smart signal acquisition and processing"; Journal of Physics, Conference Series, Sensors and their Applications XIV (SENSORS07); bearing a date of 2007; pp. 1-5; vol. 76, No. 012025; Institute of Physics Publishing Ltd.

U.S. Appl. No. 13/593,882, Bangera et al.
U.S. Appl. No. 13/593,840, Bangera et al.
U.S. Appl. No 14/305,210, Bangera et al.

FIG. 2

200 A system for monitoring medication events relating to an individual

210 Circuitry for analyzing received data for an identifier of a first medication event for an individual 220 Circuitry for analyzing the received data for at least one attribute of an individual 230 Circuitry for analyzing the received data for at least one attribute relating to a medication during the first medication event 240 Circuitry for analyzing the received data for at least one feature of visual information relating to the individual during the first medication event 250 Circuitry for analyzing the received data for at least one feature of non-visual information relating to the individual during the first medication event 260 Circuitry for analyzing the received data for a time associated with the first medication event 270 Circuitry for determining a compliance likelihood for the first medication event based on the analyses of the received data 280 Circuitry for indicating the determined compliance likelihood for the first medication event

FIG. 3

200 A system for monitoring medication events relating to an individual

210 Circuitry for analyzing received data for an identifier of a first medication event for an individual 300 Circuitry for analyzing received data encoded in a transmission originating from a cell phone 310 Circuitry for analyzing received data encoded in a transmission originating from a portable computing device 320 Circuitry for analyzing received data encoded in a transmission originating from a fixed position camera unit 330 Circuitry for analyzing received data for an identifier that includes a code 340 Circuitry for analyzing received data for an identifier that includes at least one visual information feature

200 A system for monitoring medication events relating to an individual

210 Circuitry for analyzing received data for an identifier of a first medication event for an individual

400 Circuitry for analyzing received data for an identifier that includes at least one non-visual information feature

410 Circuitry for analyzing received data for a radio-frequency identification (RFID) code

220 Circuitry for analyzing the received data for at least one attribute of an individual

420 Circuitry for associating the identifier of the first medication event with an expected individual;
Circuitry for retrieving one or more specific identifiers associated with the expected individual;
Circuitry for analyzing the received data for the presence or absence of at least one of the one or more specific identifiers; and
Circuitry for indicating the presence or absence of the expected individual based on the analysis

200 A system for monitoring medication events relating to an individual

210

220 Circuitry for analyzing the received data for at least one attribute of an individual 500 Circuitry for associating the identifier of the first medication event with an expected individual;
Circuitry for retrieving one or more attributes associated with the expected individual;
Circuitry for comparing the retrieved one or more attributes associated with the expected individual with the received data;
Circuitry for determining, based on the comparison, a confirmation likelihood for the expected individual; and
Circuitry for indicating the determined confirmation likelihood for the expected individual

200 A system for monitoring medication events relating to an individual

210

220 Circuitry for analyzing the received data for at least one attribute of an individual 600 Circuitry for analyzing the received data for at least one attribute of the individual;
Circuitry for comparing the at least one attribute of the individual with a set of attribute parameters for an expected individual;
Circuitry for determining, based on the comparison, an attribute score for the at least one attribute of the individual

200 A system for monitoring medication events relating to an individual

210

220

230 Circuitry for analyzing the received data for at least one attribute relating to a medication during the first medication event 700 Circuitry for analyzing the received data for an attribute that includes at least one visual information feature 710 Circuitry for analyzing the received data for an attribute that includes at least one non-visual information feature 720 Circuitry for analyzing the received data for an attribute that includes a radio-frequency identification (RFID) code

| 200 A system for monitoring medication events relating to an individual |
|---|
| 210 |
| 220 |
| 230 Circuitry for analyzing the received data for at least one attribute relating to a medication during the first medication event<br><br>*800 Circuitry for analyzing the received data for at least one attribute of the medication;*<br>*Circuitry for comparing the at least one attribute of the medication with a set of attribute parameters for an expected medication;*<br>*Circuitry for determining, based on the comparison, an attribute score for the at least one attribute of the medication* |
| 240 |
| 250 |
| 260 |
| 270 |
| 280 |

FIG. 9

200 A system for monitoring medication events relating to an individual

210

220

230 Circuitry for analyzing the received data for at least one attribute relating to a medication during the first medication event 900 Circuitry for associating the identifier of the first medication event with an expected medication;
Circuitry for retrieving one or more specific identifiers associated with the expected medication;
Circuitry for analyzing the received data for the presence or absence of at least one of the one or more specific identifiers; and
Circuitry for indicating the presence or absence of the expected medication based on the analysis

200 A system for monitoring medication events relating to an individual

210

220

230 Circuitry for analyzing the received data for at least one attribute relating to a medication during the first medication event

1000 Circuitry for associating the identifier of the first medication event with an expected medication;
Circuitry for retrieving one or more attributes associated with the expected medication;
Circuitry for comparing the retrieved one or more attributes associated with the expected medication with the received data;
Circuitry for determining, based on the comparison, a confirmation likelihood for the expected medication; and
Circuitry for indicating the determined confirmation likelihood for the expected medication

| 200 A system for monitoring medication events relating to an individual |
|---|
| 210 |
| 220 |
| 230 |
| 240 Circuitry for analyzing the received data for at least one feature of visual information relating to the individual during the first medication event <br> *1100 Circuitry for identifying a visual information component of the received data; Circuitry for comparing the identified visual information component of the received data with at least one visual information parameter; and Circuitry for determining a likelihood of sufficiency for the visual information component of the received data based on the comparison* |
| 250 |
| 260 |
| 270 |
| 280 |

FIG. 12

200 A system for monitoring medication events relating to an individual

210

220

230

240 Circuitry for analyzing the received data for at least one feature of visual information relating to the individual during the first medication event > 1200 Circuitry for associating the identifier of the first medication event with a set of visual information parameters for a standard medication event;
> Circuitry for comparing the at least one feature of visual information relating to the individual during the first medication event with the set of visual information parameters for the standard medication event;
> Circuitry for determining, based on the comparison, a medication event compliance score for the first medication event; and
> Circuitry for indicating the determined medication event compliance score for the first medication event

200 A system for monitoring medication events relating to an individual

210

220

230

240

250 Circuitry for analyzing the received data for at least one feature of non-visual information relating to the individual during the first medication event > 1300 Circuitry for analyzing the received data for at least one feature of non-visual information including near-infrared (IR) information > 1310 Circuitry for analyzing the received data for at least one feature of non-visual information including auditory information > 1320 Circuitry for analyzing the received data for at least one feature of non-visual information including thermal information > 1330 Circuitry for analyzing the received data for at least one feature of non-visual information including kinetic information

```
200 A system for monitoring medication events relating to an
individual
┌─────────────────────────────────────────────────────────────┐
│ 210                                                         │
└─────────────────────────────────────────────────────────────┘
┌─────────────────────────────────────────────────────────────┐
│ 220                                                         │
└─────────────────────────────────────────────────────────────┘
┌─────────────────────────────────────────────────────────────┐
│ 230                                                         │
└─────────────────────────────────────────────────────────────┘
┌─────────────────────────────────────────────────────────────┐
│ 240                                                         │
└─────────────────────────────────────────────────────────────┘
250  Circuitry for analyzing the received data for at least
one feature of non-visual information relating to the
individual during the first medication event
   ┌ ─ ─ ─ ─ ─ ─ ─ ─ ─ ─ ─ ─ ─ ─ ─ ─ ─ ─ ─ ─ ─ ─ ─ ─ ─ ─ ─ ┐
     1400  Circuitry for analyzing the received data for at
   │ least one feature of non-visual information including   │
     micropower impulse radar (MIR) information
   └ ─ ─ ─ ─ ─ ─ ─ ─ ─ ─ ─ ─ ─ ─ ─ ─ ─ ─ ─ ─ ─ ─ ─ ─ ─ ─ ─ ┘
   ┌ ─ ─ ─ ─ ─ ─ ─ ─ ─ ─ ─ ─ ─ ─ ─ ─ ─ ─ ─ ─ ─ ─ ─ ─ ─ ─ ─ ┐
   │ 1410  Circuitry for identifying a non-visual information│
   │ component of the received data;                         │
   │ Circuitry for comparing the identified non-visual       │
   │ information component of the received data with at least│
   │ one non-visual information parameter; and               │
   │ Circuitry for determining a likelihood of sufficiency for the│
   │ non-visual information component of the received data   │
   │ based on the comparison                                 │
   └ ─ ─ ─ ─ ─ ─ ─ ─ ─ ─ ─ ─ ─ ─ ─ ─ ─ ─ ─ ─ ─ ─ ─ ─ ─ ─ ─ ┘
┌─────────────────────────────────────────────────────────────┐
│ 260                                                         │
└─────────────────────────────────────────────────────────────┘
┌─────────────────────────────────────────────────────────────┐
│ 270                                                         │
└─────────────────────────────────────────────────────────────┘
┌─────────────────────────────────────────────────────────────┐
│ 280                                                         │
└─────────────────────────────────────────────────────────────┘
```

FIG. 15

200 A system for monitoring medication events relating to an individual

210

220

230

240

250 Circuitry for analyzing the received data for at least one feature of non-visual information relating to the individual during the first medication event 1500 Circuitry for associating the identifier of the first medication event with a set of non-visual information parameters for a standard medication event;
Circuitry for comparing the at least one feature of non-visual information relating to the individual during the first medication event with the set of non-visual information parameters for the standard medication event;
Circuitry for determining, based on the comparison, a medication event compliance score for the first medication event; and
Circuitry for indicating the determined medication event compliance score for the first medication event

| 200 A system for monitoring medication events relating to an individual |
|---|
| 210 |
| 220 |
| 230 |
| 240 |
| 250 |
| 260 Circuitry for analyzing the received data for a time associated with the first medication event<br>*1600 Circuitry for identifying a time component in the received data;*<br>*Circuitry for comparing the identified time component with at least one time parameter associated with an expected medication event for the individual; and*<br>*Circuitry for determining, based on the comparisons, a time score for the first medication event based on the received data* |
| 270 |
| 280 |

FIG. 17

200 A system for monitoring medication events relating to an individual

210

220

230

240

250

260 Circuitry for analyzing the received data for a time associated with the first medication event 1700 Circuitry for identifying a time component in the received data;
Circuitry for associating the identifier of a first medication event for an individual with an expected medication time for the individual;
Circuitry for comparing the identified time component with the expected medication time;
Circuitry for determining, based on the comparison, a medication event time compliance score for the first medication event; and
Circuitry for indicating the determined medication event time compliance score for the first medication event

200 A system for monitoring medication events relating to an individual

210

220

230

240

250

260

270 Circuitry for determining a compliance likelihood for the first medication event based on the analyses of the received data 1800 Circuitry for comparing the analyses with a set of parameters for a standard medication event; and
Circuitry for calculating, based on the comparison, a compliance likelihood for the first medication event 1810 Circuitry for comparing the analyses with a set of parameters for an expected medication event for the individual; and
Circuitry for calculating, based on the comparison, a compliance likelihood for the individual with the expected medication event

200 A system for monitoring medication events relating to an individual

210

220

230

240

250

260

270

280

1900 Circuitry for saving the determined compliance likelihood for the first medication event into memory 1910 Circuitry for saving the determined compliance likelihood for the first medication event into a health record for the individual 1920 Circuitry for comparing the determined compliance likelihood for the first medication event to a compliance goal for the individual; and
Circuitry for indicating the comparison

FIG. 20

200 A system for monitoring medication events relating to an individual

210

220

230

240

250

260

270

280

2000 Circuitry for the determined compliance likelihood for the first medication event to a determined compliance likelihood for a second medication event for the individual;
Circuitry for comparing the determined compliance likelihood for the first medication event and the determined compliance likelihood for the second medication event to a compliance goal for the individual; and
Circuitry for indicating the comparison 2010 Circuitry for receiving data 2020 Circuitry for saving received data into a memory 2030 Circuitry for saving the analyses of the received data into a memory

FIG. 21

200 A system for monitoring medication events relating to an individual

210

220

230

240

250

260

270

280

2100 Circuitry for saving the analysis of the received data for an identifier of a first medication event for an individual into a memory 2110 Circuitry for saving the analysis of the received data for at least one attribute of an individual into a memory 2120 Circuitry for saving the analysis of the received data for at least one attribute relating to a medication during the first medication event into a memory 2130 Circuitry for saving the analyses of the received data for at least one feature of visual information relating to the individual during the first medication event into a memory

FIG. 22

200 A system for monitoring medication events relating to an individual

210

220

230

240

250

260

270

280

2200 Circuitry for saving the analyses of the received data for at least one feature of non-visual information relating to the individual during the first medication event into a memory 2210 Circuitry for saving the analysis of the received data for a time associated with the first medication event into a memory 2220 Circuitry for saving the analysis with a set of standard analysis parameters for a standard medication event;
Circuitry for determining, based on the comparison, if the analyses are within the standard analysis parameters for a standard medication event; and
Circuitry for indicating the determination 2230 Circuitry for saving the determination into a memory

FIG. 23

200 A system for monitoring medication events relating to an individual

2300 Circuitry for analyzing received data for an identifier of a second medication event for the individual;
Circuitry for analyzing received data for the at least one attribute of the individual;
Circuitry for analyzing the received data for the at least one attribute relating to a medication during the second medication event;
Circuitry for analyzing the received data for at least one feature of visual information relating to the individual during the second medication event;
Circuitry for analyzing the received data for at least one feature of non-visual information relating to the individual during the second medication event;
Circuitry for analyzing the received data for a time associated with the second medication event;
Circuitry for determining a compliance likelihood for the second medication event based on the analyses of the received data; and
Circuitry for indicating the determined compliance likelihood for the second medication event 2310 Circuitry for comparing the determined compliance likelihood for the first medication event and the determined compliance likelihood for the second medication event;
Circuitry for determining a composite compliance likelihood for the first and second medication events;
Circuitry for saving the composite compliance likelihood into a memory; and
Circuitry for indicating the composite compliance likelihood

FIG. 24

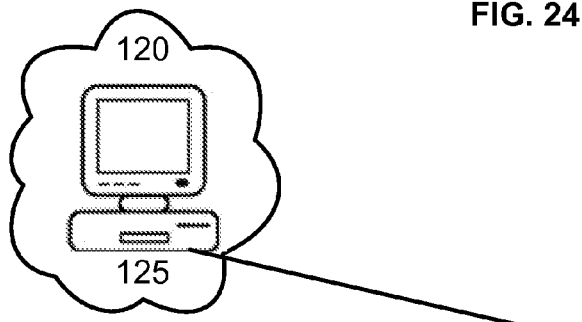

2400 A computer-readable storage medium including executable instructions for monitoring medication events relating to an individual 2410 Instructions for analyzing received data for an identifier of a first medication event for an individual 2420 Instructions for analyzing the received data for at least one attribute of an individual 2430 Instructions for analyzing the received data for at least one attribute relating to a medication during the first medication event 2440 Instructions for analyzing the received data for at least one feature of visual information relating to the individual during the first medication event 2450 Instructions for analyzing the received data for at least one feature of non-visual information relating to the individual during the first medication event 2460 Instructions for analyzing the received data for a time associated with the first medication event 2470 Instructions for determining a compliance likelihood for the first medication event based on the analyses of the received data 2480 Instructions for indicating the determined compliance likelihood for the first medication event

FIG. 25

2500 A method for monitoring medication events relating to an individual

2510 Analyzing received data for an identifier of a first medication event for an individual, the received data origination from at least one monitoring device 2520 Analyzing the received data for at least one attribute of an individual 2530 Analyzing the received data for at least one attribute relating to a medication during the first medication event 2540 Analyzing the received data for at least one feature of visual information relating to the individual during the first medication event 2550 Analyzing the received data for at least one feature of non-visual information relating to the individual during the first medication event 2560 Analyzing the received data for a time associated with the first medication event 2570 Determining a compliance likelihood for the first medication event based on the analyses of the received data 2580 Indicating the determined compliance likelihood for the first medication event

FIG. 26

> 2600 A system for monitoring medication events
>
> > 2610 Circuitry for accepting data regarding a medication event for an individual
> >
> > 2620 Circuitry for extracting, from the accepted data regarding the medication event for the individual, one or more identifiers of the medication
> >
> > 2630 Circuitry for comparing the one or more identifiers of the medication with a set of standard medication identifier parameters
> >
> > 2640 Circuitry for extracting, from the accepted data regarding the medication event for the individual, one or more visual features of the medication event
> >
> > 2650 Circuitry for comparing the one or more visual features of the medication event with a set of medication event parameters
> >
> > 2660 Circuitry for extracting, from the accepted data regarding the medication event for the individual, one or more non-visual features of the medication event
> >
> > 2670 Circuitry for comparing the one or more non-visual features of the medication event with the set of medication event parameters
> >
> > 2680 Circuitry for extracting, from the accepted data regarding the medication event for the individual, a time associated with the medication event
> >
> > 2690 Circuitry for comparing the time associated with the medication event with an expected medication event time for the individual
> >
> > 2695 Circuitry for saving the comparisons into a memory

FIG. 27

2600 A system for monitoring medication events

2610 Circuitry for accepting data regarding a medication event for an individual

2700 Circuitry for accepting data originating from a cell phone

2710 Circuitry for accepting data originating from a portable computing device

2720 Circuitry for accepting data originating from a fixed position camera unit

2730 Circuitry for accepting data originating from a plurality of devices

2740 Circuitry for accepting data originating from a micropower impulse radar (MIR) device

2600 A system for monitoring medication events

2610

2620 Circuitry for extracting, from the accepted data regarding the medication event for the individual, one or more identifiers of the medication > 2800 Circuitry for extracting visual data
>
> 2810 Circuitry for extracting radio frequency identification (RFID) information 2630 Circuitry for comparing the one or more identifiers of the medication with a set of standard medication identifier parameters > 2820 Circuitry for comparing visual features 2640 Circuitry for extracting, from the accepted data regarding the medication event for the individual, one or more visual features of the medication event > 2830 Circuitry for extracting one or more visual features over time

2600 A system for monitoring medication events

2610

2620

2630

2640

2650 Circuitry for comparing the one or more visual features of the medication event with a set of medication event parameters 2900 Circuitry for determining, from a set of standard medication event visual features, at least one expected visual feature; and
Circuitry for comparing the accepted data regarding a medication event for the individual with the determined at least one expected visual feature 2660 Circuitry for extracting, from the accepted data regarding the medication event for the individual, one or more non-visual features of the medication event 2910 Circuitry for extracting one or more non-visual features over time

2600 A system for monitoring medication events

2610

2620

2630

2640

2650

2660 Circuitry for extracting, from the accepted data regarding the medication event for the individual, one or more non-visual features of the medication event 3000 Circuitry for extracting one or more audio features 3010 Circuitry for extracting one or more near-infrared (IR) features 3020 Circuitry for extracting one or more thermal features 3030 Circuitry for extracting one or more features detectable by micropower impulse radar (MIR)

| 2600 A system for monitoring medication events |
|---|
| 2610 |
| 2620 |
| 2630 |
| 2640 |
| 2650 |
| 2660 |
| 2670 |
| 2680 |
| 2690 Circuitry for comparing the time associated with the medication event with an expected medication event time for the individual<br><br>3300 Circuitry for determining, from a set of standard medication event times, at least one expected medication event time; and<br>Circuitry for comparing the extracted time associated with the medication event with the determined at least one expected medication event time |
| 2695 |
| 3310 Circuitry for determining, from the comparison of the one or more identifiers of the medication with the set of standard medication identifier parameters, if the one or more identifiers of the medication are within the set of standard medication identifier parameters |

FIG. 34

2600 A system for monitoring medication events

2610

2620

2630

2640

2650

2660

2670

2680

2690

2695

3400 Circuitry for determining, from the comparison of the one or more non-visual features of the medication event with a set of medication event parameters, if the one or more non-visual features of the medication event are within the set of medication event parameters 3410 Circuitry for determining, from the comparison of the time associated with the medication event with the expected medication event time for the individual, if the time associated with the medication event is within the expected medication event time for the individual

FIG. 35

2600 A system for monitoring medication events
- 2610
- 2620
- 2630
- 2640
- 2650
- 2660
- 2670
- 2680
- 2690
- 2695
- | 3500 Circuitry for saving one or more of the comparisons into a medical record for the individual
- | 3510 Circuitry for determining, from the comparisons, a medication compliance score for the medication event
- | 3520 Circuitry for indicating one or more of the comparisons
- | 3530 Circuitry for activating, depending on one or more of the comparisons, an alert indicator

FIG. 36

2600 A system for monitoring medication events

3600 Circuitry for accepting data regarding a second medication event for the individual;
Circuitry for extracting, from the accepted data regarding the second medication event for the individual, one or more identifiers of the medication;
Circuitry for comparing the one or more identifiers of the medication with a set of standard medication identifier parameters;
Circuitry for extracting, from the accepted data regarding the second medication event for the individual, one or more visual features of the medication event;
Circuitry for comparing the one or more visual features of the second medication event with a set of medication event parameters;
Circuitry for extracting, from the accepted data regarding the second medication event for the individual, one or more non-visual features of the second medication event;
Circuitry for comparing the one or more non-visual features of the second medication event with the set of medication event parameters;
Circuitry for extracting, from the accepted data regarding the second medication event for the individual, a time associated with the second medication event;
Circuitry for comparing the time associated with the second medication event with an expected second medication event time for the individual; and
Circuitry for saving the comparisons associated with the second medication event into a memory 3610 Circuitry for determining, from the saved comparisons associated with the medication event and the comparisons associated with the second medication event, if the medication events meet at least one standard; and
circuitry for activating an indicator in response to the determination

FIG. 37

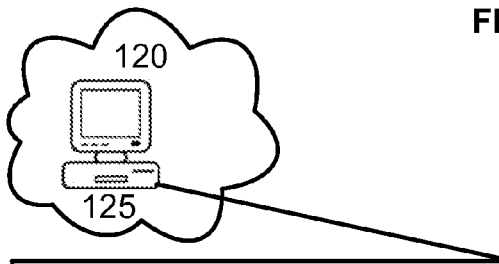

3700 A computer-readable storage medium including executable instructions for monitoring medication events relating to an individual 3710 Instructions for accepting data regarding a medication event for an individual 3720 Instructions for extracting, from the accepted data regarding the medication event for the individual, one or more identifiers of the medication 3730 Instructions for comparing the one or more identifiers of the medication with a set of standard medication identifier parameters 3740 Instructions for extracting, from the accepted data regarding the medication event for the individual, one or more visual features of the medication event 3750 Instructions for comparing the one or more visual features of the medication event with a set of medication event parameters 3760 Instructions for extracting, from the accepted data regarding the medication event for the individual, one or more non-visual features of the medication event 3770 Instructions for comparing the one or more non-visual features of the medication event with the set of medication event parameters 3780 Instructions for extracting, from the accepted data regarding the medication event for the individual, a time associated with the medication event 3790 Instructions for comparing the time associated with the medication event with an expected medication event time for the individual 3795 Instructions for saving the comparisons into a memory

FIG. 38

- 3800 A method for monitoring medication events
  - 3810 Accepting data regarding a medication event for an individual
  - 3820 Extracting, from the accepted data regarding the medication event for the individual, one or more identifiers of the medication
  - 3830 Comparing the one or more identifiers of the medication with a set of standard medication identifier parameters
  - 3840 Extracting, from the accepted data regarding the medication event for the individual, one or more visual features of the medication event
  - 3850 Comparing the one or more visual features of the medication event with a set of medication event parameters
  - 3860 Extracting, from the accepted data regarding the medication event for the individual, one or more non-visual features of the medication event
  - 3870 Comparing the one or more non-visual features of the medication event with the set of medication event parameters
  - 3880 Extracting, from the accepted data regarding the medication event for the individual, a time associated with the medication event
  - 3890 Comparing the time associated with the medication event with an expected medication event time for the individual
  - 3895 Saving the comparisons into a memory

FIG. 39

> 3900 A system for monitoring medication events
>
>> 3910 Circuitry for associating a time interval with a first medication event for an individual
>
>> 3920 Circuitry for identifying a start of the time interval associated with the first medication event
>
>> 3930 Circuitry for activating an indicator in response to the identification of the start of the time interval associated with the first medication event
>
>> 3940 Circuitry for activating at least one camera unit associated with the individual, the activating in response to the identification of the start of the time interval associated with the first medication event
>
>> 3950 Circuitry for identifying an end of the time interval associated with the first medication event
>
>> 3960 Circuitry for accepting data relating to the time interval associated with the first medication event from the at least one camera unit
>
>> 3970 Circuitry for deactivating the at least one camera unit in response to the identification of the end of the time interval associated with the first medication event

FIG. 40

3900 A system for monitoring medication events

3910 Circuitry for associating a time interval with a first medication event for an individual > 4000 Circuitry for associating a clock time interval with the first medication event > 4010 Circuitry for associating an elapsed time interval with the first medication event

3920 Circuitry for identifying a start of the time interval associated with the first medication event > 4020 Circuitry for identifying the start of a clock time interval associated with the first medication event > 4030 Circuitry for identifying the start of an elapsed time interval associated with the first medication event

3930 Circuitry for activating an indicator in response to the identification of the start of the time interval associated with the first medication event > 4040 Circuitry for activating a visual indicator > 4050 Circuitry for activating an auditory indicator > 4060 Circuitry for activating a vibratory indicator

3900 A system for monitoring medication events

3910

3920

3930

3940 Circuitry for activating at least one camera unit associated with the individual, the activating in response to the identification of the start of the time interval associated with the first medication event > 4100 Circuitry for activating at least one camera unit within a mobile phone > 4110 Circuitry for activating at least one camera unit within a portable computing device > 4120 Circuitry for activating at least one camera unit within a fixed position camera unit > 4130 Circuitry for activating a plurality of camera units > 4140 Circuitry for activating at least one camera unit including activating non-visual components of the at least one camera unit

3900 A system for monitoring medication events

3910

3920

3930

3940 Circuitry for activating at least one camera unit associated with the individual, the activating in response to the identification of the start of the time interval associated with the first medication event 4200 Circuitry for activating at least one camera unit including a microphone 4210 Circuitry for activating at least one camera unit including a RFID detector 4220 Circuitry for activating at least one camera unit for video data acquisition 4230 Circuitry for activating at least one camera unit for a series of data acquisition events 4240 Circuitry for activating at least one camera unit for data acquisition including near-infrared (IR) data

- 3900 A system for monitoring medication events
  - 3910
  - 3920
  - 3930
  - 3940 Circuitry for activating at least one camera unit associated with the individual, the activating in response to the identification of the start of the time interval associated with the first medication event
    - 4300 Circuitry for activating at least one camera unit for data acquisition including thermal data
    - 4310 Circuitry for activating at least one micropower impulse radar (MIR) device
  - 3950 Circuitry for identifying an end of the time interval associated with the first medication event
    - 4320 Circuitry for associating a clock time interval with the end of the time interval associated with the first medication event
    - 4330 Circuitry for associating an elapsed time interval with the end of the time interval associated with the first medication event
  - 3960
  - 3970

FIG. 44

- 3900 A system for monitoring medication events
  - 3910
  - 3920
  - 3930
  - 3940
  - 3950
  - 3960 Circuitry for accepting data relating to the time interval associated with the first medication event from the at least one camera unit
    - 4400 Circuitry for accepting data generated by the at least one camera unit during the time interval associated with the first medication event
    - 4410 Circuitry for accepting data relating to the time interval associated with the first medication event from each of a plurality of camera units
  - 3970 Circuitry for deactivating the at least one camera unit in response to the identification of the end of the time interval associated with the first medication event
    - 4420 Circuitry for deactivating at least one camera unit within a mobile phone
    - 4430 Circuitry for deactivating at least one camera unit within a portable computing device

FIG. 45

3900 A system for monitoring medication events

3910

3920

3930

3940

3950

3960

3970 Circuitry for deactivating the at least one camera unit in response to the identification of the end of the time interval associated with the first medication event 4500 Circuitry for deactivating at least one camera unit within a fixed position camera unit 4510 Circuitry for deactivating a plurality of camera units 4520 Circuitry for activating an indicator in response to the circuitry for accepting data relating to the time interval associated with the first medication event from the at least one camera unit 4530 Circuitry for saving the accepted data relating to the time interval associated with the first medication event from the at least one camera unit into a memory

FIG. 46

3900 A system for monitoring medication events

| 3910 |
| 3920 |
| 3930 |
| 3940 |
| 3950 |
| 3960 |
| 3970 |

4600 Circuitry for processing the accepted data relating to the time interval associated with the first medication event from the at least one camera unit into a transmission; and
Circuitry for transmitting the processed data 4610 Circuitry for activating an indicator in response to the identification of the end of the time interval associated with the first medication event 4620 Circuitry for retrieving at least one attribute of the individual from memory;
Circuitry for examining the accepted data for the at least one attribute of the individual;
Circuitry for forming an identification result for the individual from the examination; and
Circuitry for transmitting the identification result for the individual

FIG. 47

3900 A system for monitoring medication events

3910

3920

3930

3940

3950

3960

3970

4700 Circuitry for retrieving at least one attribute of the medication from memory;
Circuitry for examining the accepted data for the at least one attribute of the medication;
Circuitry for forming an identification result for the medication from the examination; and
Circuitry for transmitting the identification result for the medication 4710 Circuitry for initiating a transmission in response to the identification of the start of the time interval associated with the first medication event

FIG. 48

3900 A system for monitoring medication events

3910

3920

3930

3940

3950

3960

3970

4800 Circuitry for associating a second time interval with a second medication event for the individual;
Circuitry for identifying a start of the second time interval associated with the second medication event;
Circuitry for activating an indicator in response to the identification of the start of the second time interval associated with the second medication event;
Circuitry for activating at least one camera unit associated with the individual, the activating in response to the identification of the start of the second time interval associated with the second medication event;
Circuitry for identifying an end of the second time interval associated with the second medication event;
Circuitry for accepting data relating to the second time interval associated with the second medication event from the at least one camera unit; and
Circuitry for deactivating the at least one camera unit in response to the identification of the end of the second time interval associated with the second medication event

FIG. 49

3900 A system for monitoring medication events

3910

3920

3930

3940

3950

3960

3970

4900 Circuitry for comparing the time interval associated with the first medication event and the second time interval associated with the second medication event with a standard time interval; and
Circuitry for activating an indicator if either the time interval associated with the first medication event or the second time interval associated with the second medication event are distinct from the standard time interval 4910 Circuitry for comparing the accepted data relating to the time interval associated with the first medication event with a set of standard medication event parameters;
Circuitry for comparing the accepted data relating to the second time interval associated with the second medication event with a set of standard medication event parameters; and
Circuitry for activating an indicator if either the accepted data relating to the time interval associated with the first medication event or the accepted data relating to the second time interval associated with the second medication event are distinct from the set of standard medication event parameters

FIG. 50

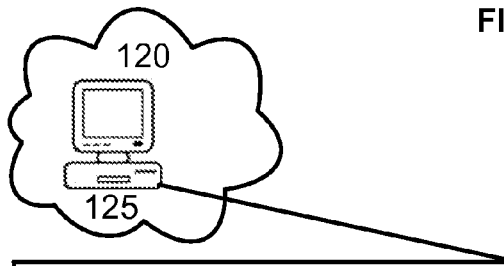

5000 A computer-readable storage medium including executable instructions for monitoring medication events 5010 Instructions for associating a time interval with a first medication event for an individual 5020 Instructions for identifying a start of the time interval associated with the first medication event 5030 Instructions for activating an indicator in response to the identification of the start of the time interval associated with the first medication event 5040 Instructions for activating at least one camera unit associated with the individual, the activating in response to the identification of the start of the time interval associated with the first medication event 5050 Instructions for identifying an end of the time interval associated with the first medication event 5060 Instructions for accepting data relating to the time interval associated with the first medication event from the at least one camera unit 5070 Instructions for deactivating the at least one camera unit in response to the identification of the end of the time interval associated with the first medication event

FIG. 51

5100 A method for monitoring medication events

5110 Associating a time interval with a first medication event for an individual 5120 Identifying a start of the time interval associated with the first medication event 5130 Activating an indicator in response to the identification of the start of the time interval associated with the first medication event 5140 Activating at least one camera unit associated with the individual, the activating in response to the identification of the start of the time interval associated with the first medication event 5150 Identifying an end of the time interval associated with the first medication event 5160 Accepting data relating to the time interval associated with the first medication event from the at least one camera unit 5170 Deactivating the at least one camera unit in response to the identification of the end of the time interval associated with the first medication event

FIG. 52

- 5200 A system for monitoring medication events
  - 5210 Circuitry for identifying a start of a time interval associated with a first medication event for an individual
  - 5220 Circuitry for activating at least one camera unit associated with the individual, the activating in response to the identification of the start of the time interval
  - 5230 Circuitry for accepting data from the at least one camera unit, the data including both visual and non-visual data
  - 5240 Circuitry for providing at least one sufficiency parameter for visual data from the first medication event
  - 5250 Circuitry for providing at least one sufficiency parameter for non-visual data from the first medication event
  - 5260 Circuitry for comparing the accepted data from the at least one camera unit with the provided at least one sufficiency parameter for visual data and with the provided at least one sufficiency parameter for non-visual data
  - 5270 Circuitry for determining, from the comparison, if the accepted data from the at least one camera unit is sufficient
  - 5280 Circuitry for activating an indicator in response to the determined sufficiency
  - 5290 Circuitry for identifying an end of the time interval associated with the first medication event
  - 5295 Circuitry for deactivating the at least one camera unit in response to the identification of the end of the time interval associated with the first medication event

FIG. 53

5200 A system for monitoring medication events

5210 Circuitry for identifying a start of a time interval associated with a first medication event for an individual

5300 Circuitry for identifying the start of a clock time interval

5310 Circuitry for identifying the start of an elapsed time interval

5220 Circuitry for activating at least one camera unit associated with the individual, the activating in response to the identification of the start of the time interval

5320 Circuitry for activating at least one camera unit within a mobile device associated with the individual

5330 Circuitry for activating at least one camera unit at a fixed location associated with the individual

5200 A system for monitoring medication events

5210

5220

5230 Circuitry for accepting data from the at least one camera unit, the data including both visual and non-visual data 5400 Circuitry for accepting data including at least two visual images 5410 Circuitry for accepting data including video data 5420 Circuitry for accepting data including near-infrared (IR) data 5430 Circuitry for accepting data including thermal data 5440 Circuitry for accepting data including audio data 5450 Circuitry for accepting data including RF (radio frequency) data 5460 Circuitry for accepting data including micropower impulse radar (MIR)-generated data

5200 A system for monitoring medication events

5210

5220

5230

5240 Circuitry for providing at least one sufficiency parameter for visual data from the first medication event 5500 Circuitry for providing at least one sufficiency parameter for visual data specific to the individual 5510 Circuitry for providing at least one sufficiency parameter for visual data including a range of values 5520 Circuitry for providing at least one sufficiency parameter for visual data including a minimum value

5200 A system for monitoring medication events

5210

5220

5230

5240

5250

5260 Circuitry for comparing the accepted data from the at least one camera unit with the provided at least one sufficiency parameter for visual data and with the provided at least one sufficiency parameter for non-visual data 5700 Circuitry for comparing the accepted data from the at least one camera unit with at least one minimum value for visual data and at least one minimum value for non-visual data 5710 Circuitry for comparing the accepted data from the at least one camera unit with at least one range of values for visual data and at least one range of values for non-visual data 5720 Circuitry for comparing the accepted data from the at least one camera unit with at least one sufficiency parameter for visual data specific to the individual and at least one sufficiency parameter for non-visual data specific to the individual

5200 A system for monitoring medication events

5210

5220

5230

5240

5250

5260

5270 Circuitry for determining, from the comparison, if the accepted data from the at least one camera unit is sufficient 5800 Circuitry for determining that the accepted data from the at least one camera unit is insufficient 5280 Circuitry for activating an indicator in response to the determined sufficiency 5810 Circuitry for activating a visual indicator 5820 Circuitry for activating an audio indicator 5290 Circuitry for identifying an end of the time interval associated with the first medication event 5830 Circuitry for identifying the end of a clock time interval 5840 Circuitry for identifying the end of an elapsed time interval

5200 A system for monitoring medication events

5210

5220

5230

5240

5250

5260

5270

5280

5290

5295

6000 Circuitry for saving determined sufficiency in a memory

6010 Circuitry for transmitting the determined sufficiency

6020 Circuitry for identifying, in response to the determined sufficiency, a start of a time interval associated with a supplementary medication event for the individual 6030 Circuitry for activating an indicator in response to the identification of the start of the time interval associated with the first medication event 6040 Circuitry for deactivating an indicator in response to the identification of the end of the time interval associated with the first medication event

FIG. 62

5200 A system for monitoring medication events

6200 Circuitry for identifying a start of a second time interval associated with a second medication event for the individual;
Circuitry for activating the at least one camera unit associated with the individual, the activating in response to the identification of the start of the second time interval;
Circuitry for accepting data from the at least one camera unit, the data including both visual and non-visual data;
circuitry for providing the at least one sufficiency parameter for visual data from the second medication event;
Circuitry for providing the at least one sufficiency parameter for non-visual data from the second medication event;
Circuitry for comparing the accepted data from the at least one camera unit with the provided at least one sufficiency parameter for visual data and with the provided at least one sufficiency parameter for non-visual data;
Circuitry for determining, from the comparison, if the accepted data from the at least one camera unit is sufficient;
Circuitry for activating an indicator in response to the determined sufficiency;
circuitry for identifying an end of the second time interval associated with the second medication event; and
Circuitry for deactivating the at least one camera unit in response to the identification of the end of the time interval associated with the second medication event 6210 Circuitry for identifying, in response to the determined sufficiency of the second medication event, a start of a time interval associated with a supplementary medication event for the individual

FIG. 63

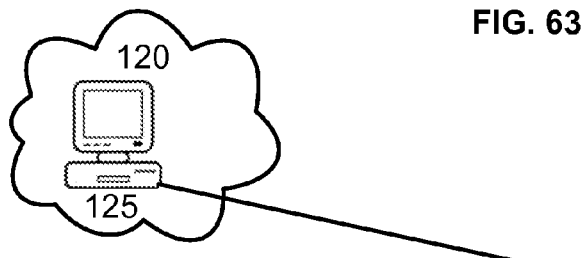

6300 A computer-readable storage medium including executable instructions for monitoring medication events 6310 Instructions for identifying a start of a time interval associated with a first medication event for an individual 6320 Instructions for activating at least one camera unit associated with the individual, the activating in response to the identification of the start of the time interval 6330 Instructions for accepting data from the at least one camera unit, the data including both visual and non-visual data 6340 Instructions for providing at least one sufficiency parameter for visual data from the first medication event 6350 Instructions for providing at least one sufficiency parameter for non-visual data from the first medication event 6360 Instructions for comparing the accepted data from the at least one camera unit with the provided at least one sufficiency parameter for visual data and with the provided at least one sufficiency parameter for non-visual data 6370 Instructions for determining, from the comparison, if the accepted data from the at least one camera unit is sufficient 6380 Instructions for activating an indicator in response to the determined sufficiency 6390 Instructions for identifying an end of the time interval associated with the first medication event 6395 Instructions for deactivating the at least one camera unit in response to the identification of the end of the time interval associated with the first medication event

FIG. 64

6400 A method for monitoring medication events

6410 Identifying a start of a time interval associated with a first medication event for an individual

6420 Activating at least one camera unit associated with the individual, the activating in response to the identification of the start of the time interval

6430 Accepting data from the at least one camera unit, the data including both visual and non-visual data

6440 Providing at least one sufficiency parameter for visual data from the first medication event

6450 Providing at least one sufficiency parameter for non-visual data from the first medication event

6460 Comparing the accepted data from the at least one camera unit with the provided at least one sufficiency parameter for visual data and with the provided at least one sufficiency parameter for non-visual data

6470 Determining, from the comparison, if the accepted data from the at least one camera unit is sufficient

6480 Activating an indicator in response to the determined sufficiency

6490 Identifying an end of the time interval associated with the first medication event

6495 Deactivating the at least one camera unit in response to the identification of the end of the time interval associated with the first medication event

FIG. 65

6500 A system for monitoring medication events

6510 Circuitry for accepting first data from a camera unit associated with an individual

6520 Circuitry for providing a set of medication intervention parameters for the individual

6530 Circuitry for comparing the accepted first data from the camera unit associated with the individual with the provided set of medication intervention parameters for the individual

6540 Circuitry for determining if the accepted first data is within the provided set of medication intervention parameters

6550 Circuitry for activating at least one indicator in response to the first determination

6560 Circuitry for accepting second data from the camera unit associated with the individual, the second data obtained after the activation of the at least one indicator

6570 Circuitry for analyzing the accepted second data for at least one attribute relating to the medication event

6580 Circuitry for comparing the accepted second data with the provided set of medication intervention parameters for the individual

6590 Circuitry for determining if the accepted second data is within the provided set of medication intervention parameters

6595 Circuitry for activating the at least one indicator in response to the second determination

FIG. 66

6500 A system for monitoring medication events

6510 Circuitry for accepting first data from a camera unit associated with an individual

6600 Circuitry for accepting visual data and accepting non-visual data

6610 Circuitry for accepting data from a camera unit integral to a mobile device

6620 Circuitry for accepting data from a camera unit integral to a fixed-location device

6630 Circuitry for accepting data including at least two visual images

6640 Circuitry for accepting data including video data

6650 Circuitry for accepting data including near-infrared (IR) data

6500 A system for monitoring medication events

6510 Circuitry for accepting first data from a camera unit associated with an individual

6700 Circuitry for accepting data including radio frequency (RF) data

6710 Circuitry for accepting data including data from a micropower impulse radar (MIR) device

6720 Circuitry for accepting data including thermal data

6730 Circuitry for accepting data including audio data

6520 Circuitry for providing a set of medication intervention parameters for the individual

6740 Circuitry for providing a set of medication intervention parameters for the individual including time parameters

6750 Circuitry for providing a set of medication intervention parameters for the individual including visual parameters

| 6530 |
|---|
| 6540 |
| 6550 |
| 6560 |
| 6570 |
| 6580 |
| 6590 |
| 6595 |

FIG. 68

6500 A system for monitoring medication events

6510

6520 Circuitry for providing a set of medication intervention parameters for the individual > 6800 Circuitry for providing a set of medication intervention parameters for the individual including audio parameters > 6810 Circuitry for providing a set of medication intervention parameters for the individual including near-infrared (IR) parameters > 6820 Circuitry for providing a set of medication intervention parameters for the individual including thermal parameters > 6830 Circuitry for providing a set of medication intervention parameters for the individual including micropower impulse radar parameters

6500 A system for monitoring medication events

6510

6520

6530 Circuitry for comparing the accepted first data from the camera unit associated with the individual with the provided set of medication intervention parameters for the individual 6900 Circuitry for comparing the accepted first data with at least one minimum sufficiency parameter 6910 Circuitry for comparing the accepted first data with a set of parameters associated with the individual 6920 Circuitry for comparing the accepted first data with a range of sufficiency parameters 6930 Circuitry for comparing the accepted first data with a series of minimum medication intervention parameters

6500 A system for monitoring medication events

6510

6520

6530

6540 Circuitry for determining if the accepted first data is within the provided set of medication intervention parameters 7000 Circuitry for determining that the accepted first data either is within the provided set of medication intervention parameters or is not within the provided set of medication intervention parameters 6550 Circuitry for activating at least one indicator in response to the first determination 7010 Circuitry for activating a visual indicator 7020 Circuitry for activating an audio indicator 7030 Circuitry for activating a vibratory indicator

6500 A system for monitoring medication events

6510

6520

6530

6540

6550

6560 Circuitry for accepting second data from the camera unit associated with the individual, the second data obtained after the activation of the at least one indicator

| 7100 Circuitry for accepting second data from at least one camera unit, the second data including at least one time value

| 7110 Circuitry for accepting data including visual data, non-visual data, and at least one time value 6570 Circuitry for analyzing the accepted second data for at least one attribute relating to the medication event

| 7120 Circuitry for presenting at least one attribute relating to a medication event; and
| Circuitry for analyzing the accepted second data for the at least one attribute relating to a medication event

6500 A system for monitoring medication events

6510

6520

6530

6540

6550

6560

6570 Circuitry for analyzing the accepted second data for at least one attribute relating to the medication event 7200 Circuitry for analyzing the accepted second data for at least one visual attribute 7210 Circuitry for analyzing the accepted second data for at least one non-visual attribute 6580 Circuitry for comparing the accepted second data with the provided set of medication intervention parameters for the individual 7220 Circuitry for comparing both visual data and non-visual data

6500 A system for monitoring medication events

6510

6520

6530

6540

6550

6560

6570

6580

6590 Circuitry for determining if the accepted second data is within the provided set of medication intervention parameters 7300 Circuitry for determining that the accepted second data either is within the provided set of medication intervention parameters or is not within the provided set of medication intervention parameters 6595 Circuitry for activating the at least one indicator in response to the second determination 7310 Circuitry for activating at least one visual indicator 7320 Circuitry for activating at least one audio indicator 7330 Circuitry for activating at least one vibratory indicator

FIG. 74

6500 A system for monitoring medication events

| 6510 |
| 6520 |
| 6530 |
| 6540 |
| 6550 |
| 6560 |
| 6570 |
| 6580 |
| 6590 |
| 6595 |

7400 Circuitry for presenting at least one attribute of the individual; and
Circuitry for analyzing the accepted first data for the at least one attribute of the individual 7410 Circuitry for presenting at least one attribute of the individual; and
Circuitry for analyzing the accepted second data for the at least one attribute of the individual 7420 Circuitry for saving the accepted first data in a memory 7430 Circuitry for saving the accepted second data in a memory

FIG. 75

6500 A system for monitoring medication events

| 6510 |
| 6520 |
| 6530 |
| 6540 |
| 6550 |
| 6560 |
| 6570 |
| 6580 |
| 6590 |
| 6595 |

7500 Circuitry for processing the at least one accepted first data;
Circuitry for processing the at least one accepted second data;
Circuitry for integrating the processed at least one accepted first data and the processed at least one accepted second data into a medication record; and
Circuitry for saving the medication record in a memory 7510 Circuitry for processing the determination if the accepted first data is within the provided set of medication intervention parameters into a first result; and
Circuitry for transmitting the first result

FIG. 76

| 6500 A system for monitoring medication events |
|---|
| 6510 |
| 6520 |
| 6530 |
| 6540 |
| 6550 |
| 6560 |
| 6570 |
| 6580 |
| 6590 |
| 6595 |
| 7600 Circuitry for processing the determination if the accepted second data is within the provided set of medication intervention parameters into a second result; and Circuitry for transmitting the second result |

FIG. 77

6500 A system for monitoring medication events

6510

6520

6530

6540

6550

6560

6570

6580

6590

6595

7710 Circuitry for accepting third data from the camera unit associated with the individual, the third data obtained after the activation of the at least one indicator in response to the second determination;
Circuitry for analyzing the accepted third data for the at least one attribute relating to the medication event;
Circuitry for comparing the accepted third data with the provided set of medication intervention parameters for the individual;
Circuitry for determining if the accepted third data is within the provided set of medication intervention parameters; and
Circuitry for activating the at least one indicator in response to the third determination

FIG. 78

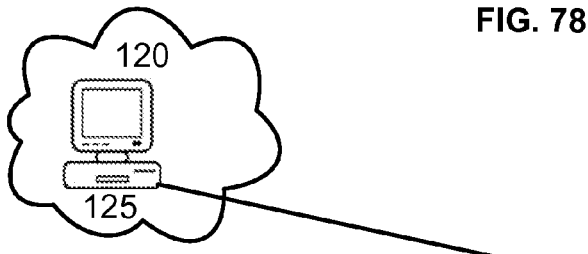

7800 A computer-readable storage medium including executable instructions for monitoring medication events 7810 Instructions for accepting first data from a camera unit associated with an individual 7820 Instructions for providing a set of medication intervention parameters for the individual 7830 Instructions for comparing the accepted first data from the camera unit associated with the individual with the provided set of medication intervention parameters for the individual 7840 Instructions for determining if the accepted first data is within the provided set of medication intervention parameters 7850 Instructions for activating at least one indicator in response to the first determination 7860 Instructions for accepting second data from the camera unit associated with the individual, the second data obtained after the activation of the at least one indicator 7870 Instructions for analyzing the accepted second data for at least one attribute relating to the medication event 7880 Instructions for comparing the accepted second data with the provided set of medication intervention parameters for the individual 7890 Instructions for determining if the accepted second data is within the provided set of medication intervention parameters 7895 Instructions for activating the at least one indicator in response to the second determination

FIG. 79

7900 A method for monitoring medication events

- 7910 Accepting first data from a camera unit associated with an individual

- 7920 Providing a set of medication intervention parameters for the individual

- 7930 Comparing the accepted first data from the camera unit associated with the individual with the provided set of medication intervention parameters for the individual

- 7940 Determining if the accepted first data is within the provided set of medication intervention parameters

- 7950 Activating at least one indicator in response to the first determination

- 7960 Accepting second data from the camera unit associated with the individual, the second data obtained after the activation of the at least one indicator

- 7970 Analyzing the accepted second data for at least one attribute relating to the medication event

- 7980 Comparing the accepted second data with the provided set of medication intervention parameters for the individual

- 7990 Determining if the accepted second data is within the provided set of medication intervention parameters

- 7995 Activating the at least one indicator in response to the second determination

FIG. 80

8000 A system for monitoring medication events

8010 Circuitry for providing a set of attributes for an individual, the set of attributes identifiable in camera unit data

8020 Circuitry for providing a set of medication condition parameters for the individual, the set of medication condition parameters identifiable in camera unit data

8030 Circuitry for accepting first data from at least one camera unit

8040 Circuitry for comparing the accepted first data with the provided set of attributes for the individual and with the provided set of medication condition parameters for the individual

8050 Circuitry for determining, from the comparison, if the accepted first data includes attributes of the individual and meets the medication condition parameters

8060 Circuitry for initiating a first medication intervention event, dependent on the determination from the comparison

8070 Circuitry for accepting second data from the at least one camera unit

8080 Circuitry for providing a set of parameters for the first medication intervention event, the set of first medication intervention parameters identifiable in camera unit data

8085 Circuitry for comparing the accepted second data with the provided set of attributes for the individual and with the provided set of parameters for the first medication intervention event

8090 Circuitry for determining, from the comparison, if the accepted second data includes attributes of the individual and meets the parameters for the first medication intervention event

8095 Circuitry for activating at least one indicator in response to the second determination

FIG. 81

8000 A system for monitoring medication events

8010 Circuitry for providing a set of attributes for an individual, the set of attributes identifiable in camera unit data 8100 Circuitry for providing non-visual attributes 8110 Circuitry for providing a set of attributes identifiable in camera unit data originating with a mobile device 8120 Circuitry for providing a set of attributes identifiable in camera unit data originating with a fixed position camera unit 8130 Circuitry for providing a set of attributes identifiable in camera unit data including at least two visual images 8140 Circuitry for providing a set of attributes identifiable in camera unit data including video data

8000 A system for monitoring medication events

8010 Circuitry for providing a set of attributes for an individual, the set of attributes identifiable in camera unit data 8200 Circuitry for providing a set of attributes identifiable in camera unit data including near-infrared (IR) data 8210 Circuitry for providing a set of attributes identifiable in camera unit data including thermal data 8220 Circuitry for providing a set of attributes identifiable in camera unit data including audio data 8230 Circuitry for providing a set of attributes identifiable in camera unit data including micropower impulse radar (MIR) data 8240 Circuitry for providing a set of attributes specific to the individual

- 8000 A system for monitoring medication events
  - 8010
  - 8020 Circuitry for providing a set of medication condition parameters for the individual, the set of medication condition parameters identifiable in camera unit data
    - 8300 Circuitry for providing visual parameters and providing non-visual parameters
    - 8310 Circuitry for providing a set of parameters identifiable in camera unit data originating with a mobile device
    - 8320 Circuitry for providing a set of parameters identifiable in camera unit data originating with a fixed position camera unit
    - 8330 Circuitry for providing a set of parameters including at least two visual parameters
    - 8340 Circuitry for providing a set of parameters identifiable in video data
  - 8030
  - 8040
  - 8050
  - 8060
  - 8070
  - 8080
  - 8085
  - 8090
  - 8095

FIG. 84

8000 A system for monitoring medication events

8010

8020 Circuitry for providing a set of medication condition parameters for the individual, the set of medication condition parameters identifiable in camera unit data 8400 Circuitry for providing a set of parameters including audio parameters 8410 Circuitry for providing a set of parameters including thermal parameters 8420 Circuitry for providing a set of parameters including near-infrared (IR) parameters 8430 Circuitry for providing a set of parameters including radio frequency (RF) parameters 8440 Circuitry for providing a set of parameters including micropower impulse radar (MIR) parameters

8000 A system for monitoring medication events

8010

8020 Circuitry for providing a set of medication condition parameters for the individual, the set of medication condition parameters identifiable in camera unit data > 8500 Circuitry for providing a set of parameters specific to the individual

8030 Circuitry for accepting first data from at least one camera unit

> 8510 Circuitry for accepting both visual and non-visual data
>
> 8520 Circuitry for accepting video data
>
> 8530 Circuitry for accepting audio data
>
> 8540 Circuitry for accepting thermal data
>
> 8550 Circuitry for accepting near-infrared (IR) data
>
> 8560 Circuitry for accepting radio frequency (RF) data

8000 A system for monitoring medication events

| 8010 |
|---|

| 8020 |
|---|

8030 Circuitry for accepting first data from at least one camera unit

> 8600 Circuitry for accepting micropower impulse radar (MIR) data

> 8610 Circuitry for accepting data from a camera unit integral to a mobile device > 8620 Circuitry for accepting data from a camera unit integral to a fixed-position device > 8630 Circuitry for accepting data from a plurality of camera units 8040 Circuitry for comparing the accepted first data with the provided set of attributes for the individual and with the provided set of medication condition parameters for the individual > 8640 Circuitry for comparing a subset of the accepted first data with the provided set of medication condition parameters for the individual and with the provided set of medication condition parameters for the individual

| 8050 |
|---|
| 8060 |
| 8070 |
| 8080 |
| 8085 |
| 8090 |
| 8095 |

FIG. 87

| 8000 A system for monitoring medication events |
|---|
| 8010 |
| 8020 |
| 8030 |
| 8040 Circuitry for comparing the accepted first data with the provided set of attributes for the individual and with the provided set of medication condition parameters for the individual |
|     8700 Circuitry for comparing visual and non-visual components of the accepted first data with the provided set of medication condition parameters for the individual and with the provided set of medication condition parameters for the individual |
| 8050 Circuitry for determining, from the comparison, if the accepted first data includes attributes of the individual and meets the medication condition parameters |
|     8710 Circuitry for determining, from the comparison, if the accepted first data meets both visual and non-visual aspects of the medication condition parameters |
| 8060 |
| 8070 |
| 8080 |
| 8085 |
| 8090 |
| 8095 |

FIG. 88

- 8000 A system for monitoring medication events
  - 8010
  - 8020
  - 8030
  - 8040
  - 8050
  - 8060 Circuitry for initiating a first medication intervention event, dependent on the determination from the comparison
    - 8800 Circuitry for activating at least one indicator
    - 8810 Circuitry for activating at least one alarm
  - 8070 Circuitry for accepting second data from the at least one camera unit
    - 8820 Circuitry for accepting second data including both visual and non-visual aspects
    - 8830 Circuitry for accepting second data including at least one time value
    - 8840 Circuitry for accepting data including a personal identifier of the individual
  - 8080
  - 8085
  - 8090
  - 8095

FIG. 89

8000 A system for monitoring medication events

8010

8020

8030

8040

8050

8060

8070 Circuitry for accepting second data from the at least one camera unit

8900 Circuitry for accepting data from a plurality of camera units

8080 Circuitry for providing a set of parameters for the first medication intervention event, the set of first medication intervention parameters identifiable in camera unit data 8910 Circuitry for providing a set of parameters including minimum values 8920 Circuitry for providing a set of both visual and non-visual parameters 8930 Circuitry for providing a set of parameters including a range of values

| 8000 A system for monitoring medication events |
|---|
| 8010 |
| 8020 |
| 8030 |
| 8040 |
| 8050 |
| 8060 |
| 8070 |
| 8080 |
| 8085 |
| 8090 Circuitry for determining, from the comparison, if the accepted second data includes attributes of the individual and meets the parameters for the first medication intervention event |
|    9000 Circuitry for comparing accepted data including both visual and non-visual data with the provided set of attributes for the individual and with the provided set of medication intervention parameters for the individual |
|    9010 Circuitry for determining, from the comparison, if the accepted second data meets both visual and non-visual aspects of the medication condition parameters |
| 8095 Circuitry for activating at least one indicator in response to the second determination |
|    9020 Circuitry for activating at least one visual indicator |

FIG. 91

8000 A system for monitoring medication events

8010

8020

8030

8040

8050

8060

8070

8080

8085

8090

8095

9100 Circuitry for saving the first determination in a memory

9110 Circuitry for saving the second determination in a memory

9120 Circuitry for saving the accepted first data in a memory

9130 Circuitry for saving the accepted second data in a memory

FIG. 92

8000 A system for monitoring medication events

8010

8020

8030

8040

8050

8060

8070

8080

8085

8090

8095

9200 Circuitry for processing the at least one accepted first data;
Circuitry for processing the at least one accepted second data;
Circuitry for integrating the processed at least one accepted first data and the processed at least one accepted second data into a medication record; and
Circuitry for saving the medication record in a memory 9210 Circuitry for processing the if the accepted first data includes attributes of the individual and meets the medication condition parameters into a first result; and
Circuitry for transmitting the first result

FIG. 93

8000 A system for monitoring medication events

8010

8020

8030

8040

8050

8060

8070

8080

8085

8090

8095

9300 Circuitry for indicating, to at least one system user, the initiating a first medication intervention event 9310 Circuitry for indicating, to at least one system user, the determining, from the comparison, if the accepted second data includes attributes of the individual and meets the parameters for the first medication intervention event

FIG. 94

8000 A system for monitoring medication events
- 8010
- 8020
- 8030
- 8040
- 8050
- 8060
- 8070
- 8080
- 8085
- 8090
- 8095

9400 Circuitry for accepting third data from the at least one camera unit;
Circuitry for providing a set of parameters for a second medication intervention event, the set of second medication intervention parameters identifiable in camera unit data;
Circuitry for comparing the accepted third data with the provided set of attributes for the individual and with the provided set of parameters for the second medication intervention event;
Circuitry for determining, from the comparison, if the accepted third data includes attributes of the individual and meets the parameters for the second medication intervention event; and
Circuitry for activating at least one indicator in response to the third determination

FIG. 95

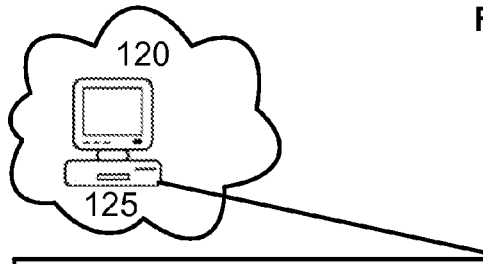

9500 A computer-readable storage medium including executable instructions for monitoring medication events 9510 Instructions for providing a set of attributes for an individual, the set of attributes identifiable in camera unit data 9520 Instructions for providing a set of medication condition parameters for the individual, the set of medication condition parameters identifiable in camera unit data 9530 Instructions for accepting first data from at least one camera unit 9540 Instructions for comparing the accepted first data with the provided set of attributes for the individual and with the provided set of medication condition parameters for the individual 9550 Instructions for determining, from the comparison, if the accepted first data includes attributes of the individual and meets the medication condition parameters 9560 Instructions for initiating a first medication intervention event, dependent on the determination from the comparison 9570 Instructions for accepting second data from the at least one camera unit 9580 Instructions for providing a set of parameters for the first medication intervention event, the set of first medication intervention parameters identifiable in camera unit data 9585 Instructions for comparing the accepted second data with the provided set of attributes for the individual and with the provided set of parameters for the first medication intervention event 9590 Instructions for determining, from the comparison, if the accepted second data includes attributes of the individual and meets the parameters for the first medication intervention event 9595 Instructions for activating at least one indicator in response to the second determination

FIG. 96

> 9600 A method for monitoring medication events
>> 9610 Providing a set of attributes for an individual, the set of attributes identifiable in camera unit data
>> 9620 Providing a set of medication condition parameters for the individual, the set of medication condition parameters identifiable in camera unit data
>> 9630 Accepting first data from at least one camera unit
>> 9640 Comparing the accepted first data with the provided set of attributes for the individual and with the provided set of medication condition parameters for the individual
>> 9650 Determining, from the comparison, if the accepted first data includes attributes of the individual and meets the medication condition parameters
>> 9660 Initiating a first medication intervention event, dependent on the determination from the comparison
>> 9670 Accepting second data from the at least one camera unit
>> 9680 Providing a set of parameters for the first medication intervention event, the set of first medication intervention parameters identifiable in camera unit data
>> 9685 Comparing the accepted second data with the provided set of attributes for the individual and with the provided set of parameters for the first medication intervention event
>> 9690 Determining, from the comparison, if the accepted second data includes attributes of the individual and meets the parameters for the first medication intervention event
>> 9695 Activating at least one indicator in response to the second determination

FIG. 98

9800 A method for monitoring medication events relating to an individual

9810 Presenting a set of parameters for determining a first medication event for an individual, the set of parameters including at least one visual parameter and at least one non-visual parameter 9820 Comparing received data with the set of parameters for determining the first medication event for the individual 9830 Determining a compliance likelihood for the first medication event based on the comparison 9840 Indicating the determined compliance likelihood for the first medication event on a computing device

FIG. 99

9900 A system for monitoring medication events relating to an individual

9910 Circuitry for presenting a set of parameters for determining a first medication event for an individual, the set of parameters including at least one visual parameter and at least one non-visual parameter > 9950 Circuitry including at least one visual parameter specific to the individual;
> Circuitry including at least one visual parameter specific to a medication;
> Circuitry including at least one non-visual parameter specific to the individual; and
> Circuitry including at least one non-visual parameter specific to the medication 9920 Circuitry for comparing received data with the set of parameters for determining the first medication event for the individual 9930 Circuitry for determining a compliance likelihood for the first medication event based on the comparison 9940 Circuitry for indicating the determined compliance likelihood for the first medication event on a computing device > 9960 Circuitry for saving the determined compliance likelihood into a memory > 9970 Circuitry for saving the determined compliance likelihood into a medical record for the individual > 9980 Circuitry for initiating a transmission including the determined compliance likelihood > 9990 Circuitry for saving the received data into a memory

FIG. 100

10000 A system for monitoring medication events relating to an individual

10010 Circuitry for determining a start of a medication event interval for an individual 10020 Circuitry for receiving data from at least one camera unit associated with the individual, the data including both visual data and non-visual data 10030 Circuitry for presenting a set of parameters for determining a first medication event for an individual, the set of parameters including at least one visual parameter and at least one non-visual parameter 10040 Circuitry for comparing the received data with the set of parameters for determining the first medication event for the individual 10050 Circuitry for determining a compliance likelihood for the first medication event based on the comparison 10060 Circuitry for indicating the determined compliance likelihood for the first medication event

FIG. 101

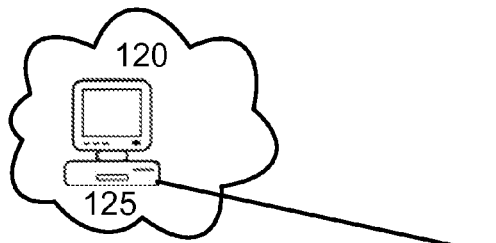

10100 A computer-readable storage medium including executable instructions for monitoring medication events relating to an individual 10110 Instructions for determining a start of a medication event interval for an individual 10120 Instructions for receiving data from at least one camera unit associated with the individual, the data including both visual data and non-visual data 10130 Instructions for presenting a set of parameters for determining a first medication event for an individual, the set of parameters including at least one visual parameter and at least one non-visual parameter 10140 Instructions for comparing the received data with the set of parameters for determining the first medication event for the individual 10150 Instructions for determining a compliance likelihood for the first medication event based on the comparison 10160 Instructions for indicating the determined compliance likelihood for the first medication event

10200 A method for monitoring medication events relating to an individual

10210 Determining a start of a medication event interval for an individual

10220 Receiving data from at least one camera unit associated with the individual, the data including both visual data and non-visual data 10230 Presenting a set of parameters for determining a first medication event for an individual, the set of parameters including at least one visual parameter and at least one non-visual parameter 10240 Comparing the received data with the set of parameters for determining the first medication event for the individual 10250 Determining a compliance likelihood for the first medication event based on the comparison 10260 Indicating the determined compliance likelihood for the first medication event

COMPUTATIONAL SYSTEMS AND METHODS FOR MONITORING MEDICATION EVENTS INCLUDING USE OF A CAMERA AND DATA COMPARISON

CROSS-REFERENCE TO RELATED APPLICATIONS

The present application is related to the following listed application(s) (the "Related Applications"). All subject matter of the Related Applications and of any and all parent, grandparent, great-grandparent, etc. applications of the Related Applications, is incorporated herein by reference to the extent such subject matter is not inconsistent herewith.

RELATED APPLICATIONS

U.S. patent application No. 13/593,840, entitled COMPUTATIONAL SYSTEMS AND METHODS FOR MONITORING MEDICATION EVENTS, naming Mahalaxmi Gita Bangera, Roderick A. Hyde, Jordin T. Kare, Eric C. Leuthardt, Elizabeth A. Sweeney, and Lowell L. Wood, Jr. as inventors, filed 24 Aug. 2012.

U.S. patent application No. 13/593,882, entitled COMPUTATIONAL SYSTEMS AND METHODS FOR MONITORING MEDICATION EVENTS, naming Mahalaxmi Gita Bangera, Roderick A. Hyde, Jordin T. Kare, Eric C. Leuthardt, Elizabeth A. Sweeney, and Lowell L. Wood, Jr. as inventors, filed 24 Aug. 2012.

SUMMARY

In some embodiments, a system includes but is not limited to a system for monitoring medication events relating to an individual, including: circuitry for analyzing received data for an identifier of a first medication event for an individual; circuitry for analyzing the received data for at least one attribute of an individual; circuitry for analyzing the received data for at least one attribute relating to a medication during the first medication event; circuitry for analyzing the received data for at least one feature of visual information relating to the individual during the first medication event; circuitry for analyzing the received data for at least one feature of non-visual information relating to the individual during the first medication event; circuitry for analyzing the received data for a time associated with the first medication event; circuitry for determining a compliance likelihood for the first medication event based on the analyses of the received data; and circuitry for indicating the determined compliance likelihood for the first medication event. In one aspect, a system includes computer-readable storage medium including executable instructions for monitoring medication events relating to an individual, the computer-readable storage medium including: instructions for analyzing received data for an identifier of a first medication event for an individual; instructions for analyzing the received data for at least one attribute of an individual; instructions for analyzing the received data for at least one attribute relating to a medication during the first medication event; instructions for analyzing the received data for at least one feature of visual information relating to the individual during the first medication event; instructions for analyzing the received data for at least one feature of non-visual information relating to the individual during the first medication event; instructions for analyzing the received data for a time associated with the first medication event; instructions for determining a compliance likelihood for the first medication event based on the analyses of the received data; and instructions for indicating the determined compliance likelihood for the first medication event. In addition to the foregoing, other system aspects are described in the claims, drawings, and text forming a part of the present disclosure.

In some embodiments, a computer-readable storage medium includes executable instructions for monitoring medication events relating to an individual, the computer-readable storage medium including: instructions for analyzing received data for an identifier of a first medication event for an individual; instructions for analyzing the received data for at least one attribute of an individual; instructions for analyzing the received data for at least one attribute relating to a medication during the first medication event; instructions for analyzing the received data for at least one feature of visual information relating to the individual during the first medication event; instructions for analyzing the received data for at least one feature of non-visual information relating to the individual during the first medication event; instructions for analyzing the received data for a time associated with the first medication event; instructions for determining a compliance likelihood for the first medication event based on the analyses of the received data; and instructions for indicating the determined compliance likelihood for the first medication event. In addition to the foregoing, other computer product aspects are described in the claims, drawings, and text forming a part of the present disclosure.

In some embodiments, a method includes but is not limited to a method for monitoring medication events relating to an individual, including: analyzing received data for an identifier of a first medication event for an individual, the received data originating from at least one monitoring device; analyzing the received data for at least one attribute of an individual; analyzing the received data for at least one attribute relating to a medication during the first medication event; analyzing the received data for at least one feature of visual information relating to the individual during the first medication event; analyzing the received data for at least one feature of non-visual information relating to the individual during the first medication event; analyzing the received data for a time associated with the first medication event; determining a compliance likelihood for the first medication event based on the analyses of the received data; and indicating the determined compliance likelihood for the first medication event. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2 depicts a system for monitoring medication events relating to an individual.

FIG. 3 illustrates aspects of the system of FIG. 2.

FIG. 4 shows aspects of the system of FIG. 2.
FIG. 5 depicts aspects of the system of FIG. 2.
FIG. 6 illustrates aspects of the system of FIG. 2.
FIG. 7 shows aspects of the system of FIG. 2.
FIG. 8 depicts aspects of the system of FIG. 2.
FIG. 9 illustrates aspects of the system of FIG. 2.
FIG. 10 shows aspects of the system of FIG. 2.
FIG. 11 depicts aspects of the system of FIG. 2.
FIG. 12 illustrates aspects of the system of FIG. 2.
FIG. 13 illustrates aspects of the system of FIG. 2.
FIG. 14 shows aspects of the system of FIG. 2.
FIG. 15 depicts aspects of the system of FIG. 2.
FIG. 16 illustrates aspects of the system of FIG. 2.
FIG. 17 shows aspects of the system of FIG. 2.
FIG. 18 depicts aspects of the system of FIG. 2.
FIG. 19 illustrates aspects of the system of FIG. 2.
FIG. 20 shows aspects of the system of FIG. 2.
FIG. 21 depicts aspects of the system of FIG. 2.
FIG. 22 illustrates aspects of the system of FIG. 2.
FIG. 23 shows aspects of the system of FIG. 2.
FIG. 24 depicts a system including computer-readable storage medium including executable instructions for monitoring medication events relating to an individual.
FIG. 25 illustrates a flowchart of a method for monitoring medication events relating to an individual.
FIG. 26 depicts a system for monitoring medication events.
FIG. 27 illustrates aspects of the system of FIG. 26.
FIG. 28 shows aspects of the system of FIG. 26.
FIG. 29 depicts aspects of the system of FIG. 26.
FIG. 30 illustrates aspects of the system of FIG. 26.
FIG. 33 shows aspects of the system of FIG. 26.
FIG. 34 depicts aspects of the system of FIG. 26.
FIG. 35 illustrates aspects of the system of FIG. 26.
FIG. 36 shows aspects of the system of FIG. 26.
FIG. 37 depicts a system including computer-readable storage medium including executable instructions for monitoring medication events relating to an individual.
FIG. 38 illustrates a flowchart of a method for monitoring medication events relating to an individual.
FIG. 39 shows a system for monitoring medication events.
FIG. 40 shows aspects of the system of FIG. 39.
FIG. 41 depicts aspects of the system of FIG. 39.
FIG. 42 illustrates aspects of the system of FIG. 39.
FIG. 43 shows aspects of the system of FIG. 39.
FIG. 44 depicts aspects of the system of FIG. 39.
FIG. 45 illustrates aspects of the system of FIG. 39.
FIG. 46 shows aspects of the system of FIG. 39.
FIG. 47 depicts aspects of the system of FIG. 39.
FIG. 48 illustrates aspects of the system of FIG. 39.
FIG. 49 shows aspects of the system of FIG. 39.
FIG. 50 depicts a system including computer-readable storage medium including executable instructions for monitoring medication events.
FIG. 51 illustrates a flowchart of a method for monitoring medication events.
FIG. 52 shows a system for monitoring medication events.
FIG. 53 shows aspects of the system of FIG. 52.
FIG. 54 depicts aspects of the system of FIG. 52.
FIG. 55 illustrates aspects of the system of FIG. 52.
FIG. 57 depicts aspects of the system of FIG. 52.
FIG. 58 illustrates aspects of the system of FIG. 52.
FIG. 60 depicts aspects of the system of FIG. 52.
FIG. 62 shows aspects of the system of FIG. 52.
FIG. 63 depicts a system including computer-readable storage medium including executable instructions for monitoring medication events.
FIG. 64 illustrates a flowchart of a method for monitoring medication events.
FIG. 65 shows a system for monitoring medication events.
FIG. 66 shows aspects of the system of FIG. 65.
FIG. 67 depicts aspects of the system of FIG. 65.
FIG. 68 illustrates aspects of the system of FIG. 65.
FIG. 69 shows aspects of the system of FIG. 65.
FIG. 70 depicts aspects of the system of FIG. 65.
FIG. 71 illustrates aspects of the system of FIG. 65.
FIG. 72 shows aspects of the system of FIG. 65.
FIG. 73 depicts aspects of the system of FIG. 65.
FIG. 74 illustrates aspects of the system of FIG. 65.
FIG. 75 shows aspects of the system of FIG. 65.
FIG. 76 depicts aspects of the system of FIG. 65.
FIG. 77 illustrates aspects of the system of FIG. 65.
FIG. 78 depicts a system including computer-readable storage medium including executable instructions for monitoring medication events.
FIG. 79 illustrates a flowchart of a method for monitoring medication events.
FIG. 80 shows a system for monitoring medication events.
FIG. 81 shows aspects of the system of FIG. 80.
FIG. 82 depicts aspects of the system of FIG. 80.
FIG. 83 illustrates aspects of the system of FIG. 80.
FIG. 84 shows aspects of the system of FIG. 80.
FIG. 85 depicts aspects of the system of FIG. 80.
FIG. 86 illustrates aspects of the system of FIG. 80.
FIG. 87 shows aspects of the system of FIG. 80.
FIG. 88 depicts aspects of the system of FIG. 80.
FIG. 89 illustrates aspects of the system of FIG. 80.
FIG. 90 shows aspects of the system of FIG. 80.
FIG. 91 depicts aspects of the system of FIG. 80.
FIG. 92 illustrates aspects of the system of FIG. 80.
FIG. 93 shows aspects of the system of FIG. 80.
FIG. 94 depicts aspects of the system of FIG. 80.
FIG. 95 shows a system including computer-readable storage medium including executable instructions for monitoring medication events.
FIG. 96 illustrates a flowchart of a method for monitoring medication events.
FIG. 98 illustrates a flowchart of a method for monitoring medication events.
FIG. 99 shows a system for monitoring medication events relating to an individual.
FIG. 100 depicts a system for monitoring medication events relating to an individual.
FIG. 101 shows a system including computer-readable storage medium including executable instructions for monitoring medication events relating to an individual.
FIG. 102 illustrates a flowchart of a method for monitoring medication events relating to an individual.

DETAILED DESCRIPTION

Figure 1:
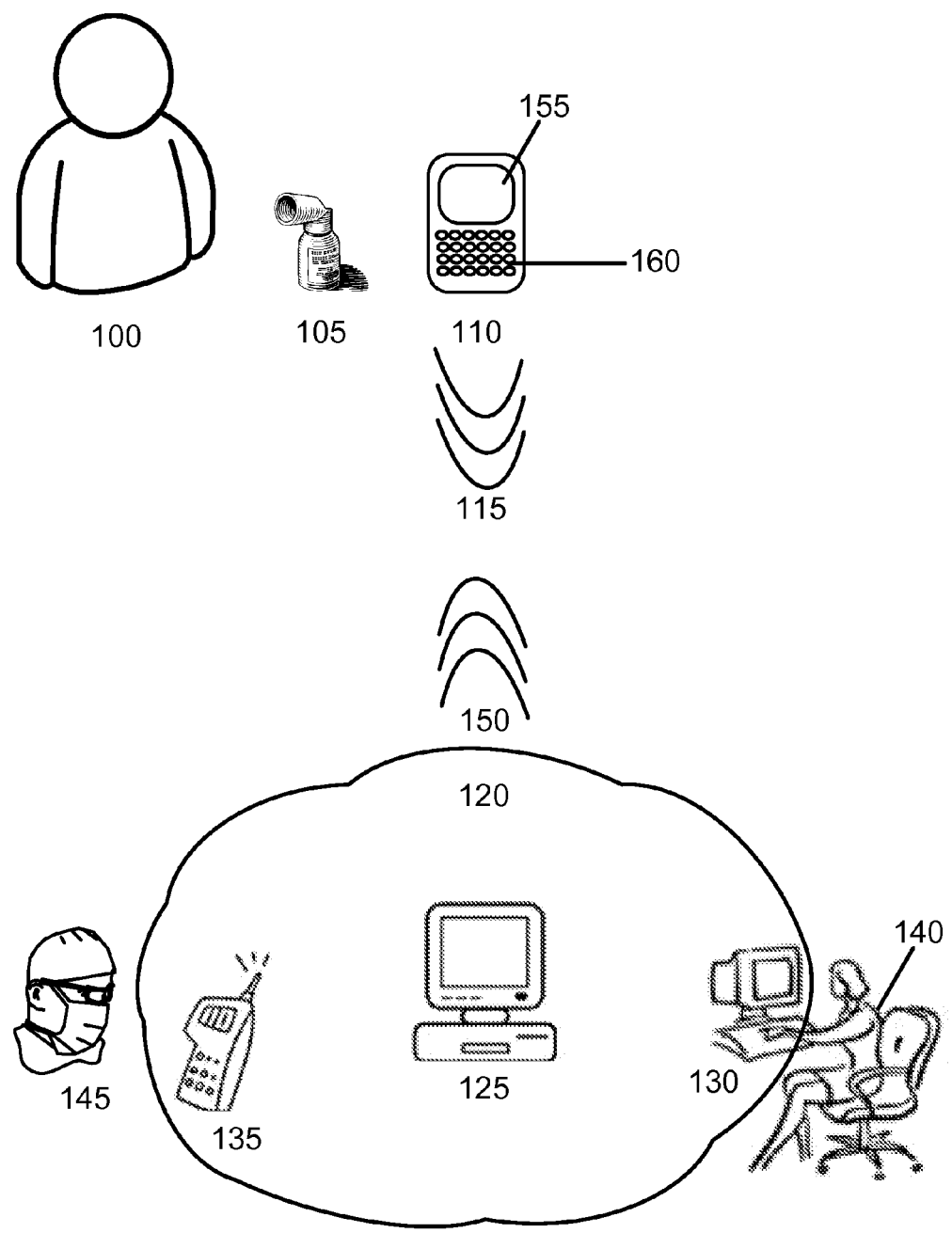
FIG. 1 is a illustrates aspects of a system for monitoring medication events relating to an individual.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Implementations may include executing a special-purpose instruction sequence or invoking circuitry for enabling, triggering, coordinating, requesting, or otherwise causing one or more occurrences of the functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit).

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., Wikipedia, Logic gates, http://en.wikipedia.org/wiki/Logic_gates (as of Jun. 5, 2012, 21:03 GMT).

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., Wikipedia, Computer architecture, http://en.wikipedia.org/wiki/Computer_architecture (as of Jun. 5, 2012, 21:03 GMT). The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "1111000010101111000011110011111" (a 32 bit instruction). Machine language is typically incomprehensible by most humans (e.g., the above example was just ONE instruction, and some personal computers execute more than two billion instructions every second).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configuration, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

The herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting. For example, in some embodiments the systems and methods described herein can be implemented as a computer program product comprising an article of manufacture and bearing instructions. For example, in some embodiments the systems and methods described herein can be implemented as computer architecture comprising at least one level. For example, in some embodiments the systems and methods described herein can be implemented as a device specified by computational language. The logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such.

The systems and methods described herein are intended for use to monitor medication compliance for individuals who have received instructions to take one or more medications as part of a medication regimen under the care of a medical professional. The systems and methods described herein may also be useful for individuals who have a history of non-compliance with medication regimens to confirm their adherence to the regimen. The systems and methods described herein can assist to ensure that the individual has complied with the medication regimen instructions, for example with the instructions for dosages and times of administration. The systems and methods described herein can also assist to ensure that the individual has complied with the medication regimen instructions, for example in response to a medical event that would indicate medical intervention is appropriate (e.g. labored breathing indicating a potential asthma event, or unsteady gait indicating dizziness and a likelihood of a fainting event). The systems and methods described herein can also assist to ensure that the individual has complied with the medication regimen instructions, for example in response to a current medical impairment (e.g. instructions to take a medication in response to wheezing when breathing). The systems and methods described herein can also assist to ensure that the individual has complied with the medication regimen instructions, for example in response to imminent medical impairment (e.g. instructions to take a medication in response to tremors indicating the onset of a seizure).

The combination of recording visual as well as non-visual data over the period of the medication event can also assist with detection of intentional "spoofing," or attempts to by an individual to make the record appear that they have taken their medication when in fact they have not. The combination of visual data (e.g. an individual putting pills in his or her mouth) as well as non-visual data (e.g. the sound of swallowing, or the thermal change in the throat as the medication is swallowed) can provide additional support for compliance with a medication regimen.

Monitoring data obtained from the methods and systems described herein can be integrated into a health record or a health history for the individual, for example for later review by a health care provider or for insurance purposes. The monitoring data described herein includes a combination of visual data (such as generated by a camera) and non-visual data (such as audio data, thermal data, near-IR data, MIR data or RF data) over the time of the medication event to ensure that a full record is captured and recorded of the individual taking the medication.

In some embodiments, methods and systems described herein can include an alert system, wherein a caregiver is notified when the system does not receive data indicating that an individual has taken his or her medication on time. In some embodiments, methods and systems described herein can include an alert system, wherein a caregiver is notified when the system does not receive data indicating that an individual has taken his or her medication in response to a specific medical event, such as wheezing, unsteady gait, or fever. In some situations, a lack of compliance with a medication regimen can have serious health implications for an individual, and a caregiver can be notified to intervene. Such systems may be helpful, for example, for individuals who have periods of confusion and may need to be reminded with a phone call from a caregiver or other means to ensure compliance with their medication regimen. In some embodiments, methods and systems described herein can include an alert system, wherein the individual is reminded when it is time for a medication. This may be helpful for individuals who have periods of confusion or forgetfulness.

For a more complete understanding, reference now is made to the following descriptions taken in connection with the accompanying drawings. The use of the same symbols in different drawings typically indicates similar or identical drawings, unless context indicates otherwise. With reference now to FIG. 1, shown is an example that illustrates aspects of a system for monitoring medication events relating to an individual that may serve as a context for introducing one or more processes and/or devices described herein. The description of FIG. 1 can be applied, for example, as a context for the description of FIGS. 2-102 herein. In some embodiments, the systems and methods described herein can be utilized by an individual to record and document his or her compliance with a medication regimen (e.g. for insurance reimbursement purposes or as part of an individual medical record). In some embodiments, the systems and methods described herein can be utilized by an insurance provider to confirm medication compliance. In some embodiments, the systems and methods described herein can be utilized by researchers to obtain data regarding medication compliance for patients with particular diagnoses or types of medication regimens. In some embodiments, the systems and methods described herein can be utilized by a medical caregiver team to confirm and document compliance of an individual with a medication regimen. In some embodiments, the systems and methods described herein can be utilized by a medical caregiver team to ensure that a patient has complied with a medication regimen. In some embodiments, the systems and methods described herein can be utilized by a medical caregiver team to ensure a complete medical record of an individual patient's medication history. In some embodiments, the systems and methods described herein can be utilized by a medical caregiver team to record medication compliance by a patient when there is a possibility of medication overdose, underdose, or multiple drug interactions. Monitoring of medication events can be of particular importance when utilized with patients with specific medical issues, such as psychosis, memory loss, or sensitivities to high or low medication levels. Monitoring of medication events can be important to confirm that an appropriate medication regimen has been followed by an individual exhibiting physical symptoms of a medical need. For example, wheezing can indicate a need for asthma medication. For example, blood pressure changes can indicate a need for diuretics. For example, an unsteady gait can indicate a need for anti-seizure medication.

In some embodiments, an individual has predetermined individualized medication intervention parameters accessible to the system that indicate when a medication event is required as part of a medication regimen for that individual. The medication intervention parameters can include those that indicate a specific physiologic condition of the individual, which the medical caregiver has determined require a medication event as part of the medication regimen. The medication intervention parameters can include specific physical symptoms or indicators that a medication event is necessary for a particular individual. For example, an asthmatic individual can have medication intervention parameters that include wheezing for a period of time or to a degree of loudness. For example, an asthmatic individual can have medication intervention parameters that include levels of and/or ratios of gasses in exhaled breath, such as nitric oxide, nitric dioxide and carbon dioxide. See US Patent Application Nos.: 2007/0048180 to Gabriel et al., "Nanoelectronic breath analyzer and asthma monitor;" 2007/0048181 to Chang et al., "Carbon dioxide nanosensor and respiratory CO2 monitors;" 2006/0055392 to Passmore et al., "Remotely communicating, battery-powered nanostructure sensor devices;" 2008/0050839 to Suslick and McNamara, "Apparatus and method for detecting lung cancer using exhaled breath;" and International Application No. PCT/US2007/010836 to Gabriel et al., "Nanoelectronic breath analyzer and asthma monitor;" which are each incorporated herein by reference. See also Kuzmych et al., "Carbon nanotube sensors for exhaled breath components," Nanotechnology 18 (2007), which is incorporated by reference herein. For example, an epileptic individual can have medication intervention parameters that include slurring speech, unsteady gait, or falling. For example, a diabetic individual can have medication intervention parameters that include dilated pupils, unsteady gait, or falling. For example, a diabetic individual can have medication intervention parameters that include acetones and/or ketones in breath. See U.S. Pat. No.: 6,841,391 to Lewis et al., "Medical applications of artificial olfactometry;" and U.S. Pat. No. 7,261,857 to Suslick et al., "Colorimetric artificial nose having an array of dyes and method for artificial olfaction;" as well as US Patent Application No. 2010/0166604 to Lim et al., "Colorimetric sensor arrays based on nanoporous pigments," which are each incorporated herein by reference. For example, an individual with a cardiac or respiratory impairment can have medication intervention parameters that include blood oxygenation levels that indicate hyoxemia.

FIG. 1 illustrates an individual 100 and at least one medication 105 associated with the individual 100 and administered to the individual 100 as part of a medication regimen including a series of medication events. An individual 100 is an individual person who, under the care or oversight of a medical professional, has a pre-established medication regimen including periodic medication events for one or more medications 105. An individual 100 has a medication regimen including periodic medication events with one or more medications 105. A "medication," as used herein, refers to a medicinal agent, drug or medicament administered to an individual person under the instructions of a medical professional for use in the medical diagnosis, cure, treatment or prevention of disease. For example, a medication can include one or more drugs formulated in pill, capsule, or liquid forms. For example, a medication can include one or more drugs administered via an inhaler device. For example, a medication can include one or more drugs administered via topical application. For example, a medication can include one or more drugs administered via transdermal application, such as with a transdermal patch. For example, a medication can include or one or more drugs administered via injection, such as with a syringe device. A medication event can include multiple medications. A medication event can include multiple medications administered in different modalities, for example one or more drugs formulated in pill form as well as one or more drugs administered via topical application. A medication can include one or more medicinal agents available only under the supervision of a medical professional (e.g. prescription medication). For example, a medication can include a medication prescribed for the treatment of anxiety, pain, mental health issues, heart disease, diabetes, asthma or other respiratory disease, allergy, contraception, infection or cancer. For example, a medication can include Cymbalta®, Enbrel®, Actos®, Singulair®, Seroquel®, Abilify®, Advair Diskus®, or Lipitor®. A medication can include one or more medicinal agents that are generally available (e.g. non-prescription or over-the-counter medication) that are included in the medication regimen by a medical professional. For example, a medication can include aspirin, ibuprofen, naproxen, dextromethorphan, ephedrine, diphenhydramine, or vitamin supplements. A medication 105 can be self-administered to the individual, such as when an individual takes pills, drinks a liquid medicament, or uses an inhaler. The medication 105 can be partially administered to the individual with assistance, such as when a second person assists the individual 100 to take pills, drink a liquid medicament, or use an inhaler.

A "medication event," as used herein, refers to an administration or application of a specific dosage of one or more medications to an individual either by themselves or with assistance as part of a medication regimen. A medication event can include a time window for administration of one or more medications, such as "daily at 2 PM" or "every 6 hours" wherein the time window starts at those times. A medication event can be triggered by a specific event for the individual, such as "administer within 30 minutes of the completion of a meal" or "begin inhaler administration at least 1 hour before the start of strenuous exercise."

A "medication regimen," as used herein, is a schedule of medication events for an individual. A medication regimen is specified by a medical professional and is directed to a particular individual. For example, a medication regimen can include daily, weekly, or monthly schedules of medication dosages and times of administration. A medication regimen can include two or more medications, each with their specific instructions for dosage amounts and times of administration to an individual. A medication regimen can include alternate, backup or substitute instructions. For example, a medication regimen can include instructions such as "when medication X is not taken in the first time window for administration, double the dosage at the next time window." For example, a medication regimen can include instructions such as "when medication Y is not taken in a time window for administration, take the recommended dosage within 30 minutes of the end of the next meal." A medication regimen can include instructions relative to a secondary event. For example, a medication regimen can include instructions for medication events contingent on one or more secondary events. For example, a medication regimen can include instructions for medication events after a particular blood sugar reading for a diabetic. For example, a medication regimen can include instructions for medication events after a particular blood pressure reading for an individual. For example, a medication regimen can include instructions for medication events after a patient reports a symptom, such as pain or nausea. A medication event can include instructions for medication events in response to a physiologic indicator. For example, a medication regimen can include instructions for medication events after a high breath ketone reading for an individual. For example, a medication regimen can include instructions for medication events after detection of an abnormal heart rhythm. For example, a medication regimen can include instructions for medication events after detection of hyoxemia.

As used herein, "visual information" refers to information derived from a visual source, such as information acquired from a camera. As used herein, "visual information" can include, for example, information acquired from a digital camera as one or more images taken in a time series. As used herein, "visual information" can include, for example, information acquired from a digital camera using a video function of the camera. For example, visual information can include the analysis of an individual's eye pupil characteristics. See U.S. Pat. No.: 6,097,295 to Griesinger et al., "Apparatus for Determining the Alertness of a Driver," and U.S. Pat. No. 7,226,164 to Abourizk et al., "Method and Apparatus for Testing Sleepiness," which are each incorporated herein by reference. Visual information can include information that is the basis of an analysis of facial and body characteristics, such as to monitor an individual for physical and mental impairment (e.g. increased movement, reduced movement, spasmodic or disordered movement). Similarly, as used herein, "visual data" includes data that is derived from a detection of a visual event, such as through a series of camera images or a video.

As used herein, "non-visual information" refers to information derived from a non-visual source, such as information derived from a sound, a temperature, a vibration, a wave in a non-visual frequency, or other non-visual sources. As used herein, "non-visual information" can include, for example, information acquired from a near-IR source. As used herein, "non-visual information" can include, for example, thermal information, such as acquired from a temperature measuring device. As used herein, "non-visual information" can include, for example, information derived from a radio-frequency identification (RFID) tag and acquired by a reader. The RFID tag can be attached, for example, to an identification item worn by the patient (i.e. an identification bracelet including a RFID tag). The RFID tag can be attached, for example, to a medication label or packaging. The RFID tag can be attached, for example, to the medication itself See: U.S. Pat. No. 7,616, 111 to Covannon et al., titled "System to Monitor the Ingestion of Medicines;" and U.S. Pat. No. 7,782,189 to Spoonhower and Covannon, titled "System to Monitor the Ingestion of Medicines," which are each incorporated by reference herein. As used herein, "non-visual information" can include, for example, information derived from an audio source. As used herein, "non-visual information" can include, for example, information acquired from a micropower impulse radar (MIR). See: "Micropower Impulse Radar," Azevedo and McEwan, Science and Technology Review, January/February 1996, pages 17-29; and US Patent Application Publications No. 2004/0249257 and 2004/0249258 to Tupin et al., each titled "Article of Manufacture for Extracting Physiological Data Using Ultra-Wideband Radar and Improved Signal Processing Techniques," which are all incorporated by reference herein. As used herein, "non-visual information" can include, for example, information derived from a ultra-wideband radar source. See, for example, US Patent Application Publication No. 2009/0227882 to Foo, titled "Ultra Wideband Monitoring Systems and Antennas," which is incorporated by reference herein. As used herein, "non-visual information" can include, for example, information derived from a reflected electromagnetic signal. See: U.S. Pat. No. 7,272,431 to McGrath, titled "Remote-Sensing Method and Device;" and U.S. Pat. No. 7,811,234 to McGrath, titled "Remote-Sensing Method and Device;" which are each incorporated by reference herein. As used herein, "non-visual information" can include, for example, information derived from an audio or auditory source, such as acquired by a microphone. Audio monitoring of speech can be used to monitor for cognitive, psychiatric, physical, or other impairment. As used herein, "non-visual information" can include, for example, information derived from the motion of the individual, such as acquired by an accelerometer. See Culhane et al., "Accelerometers in rehabilitation medicine for older adults," *Age and Aging* 34:556-560 (2005), which is incorporated by reference herein. As used herein, "non-visual information" can include, for example, information derived from blood oxygenation levels, and acquired by infrared photometry. See Karlen et al., "The Phone Oximeter," EMBC Unconference 2011, which is incorporated by reference herein. As used herein, "non-visual information" can include, for example, information derived from heart rhythms and rates, and acquired from acoustic and vibrational sensors. See, for example, US Patent Application No. 2011/0295127 to Sandler and Mansy, "Vibro-acoustic Detection of Cardiac Conditions," which is incorporated by reference herein. As used herein, "non-visual information" can include, for example, information derived from heart rhythms and rates, and acquired from electric potential sensors. See, for example: US Patent Application No. 2006/0058694 to Clark et al., "Electrodynamic Sensors and Applications Thereof;" International Publication Number WO 03/048789 to Clark et al., "Electrodynamic Sensors and Applications Thereof;" and U.S. Pat. No. 7,245,956 to Matthews et al., "Unobtrusive Measurement System for Bioelectric Signals," which are each incorporated herein by reference. See also: Harland et al., "Electric potential probes—new directions in the remote sensing of the human body," *Meas. Sci. Technol.* 13: 163-169 (2002); and Prance et al., Adaptive electric potential sensors for smart signal acquisition and processing," *Journal of Physics: Conference Series* 76 (2007), which are each incorporated herein by reference. As used herein, "non-visual information" can include, for example, information derived from heart rhythms and rates, and acquired from an electromagnetic signal reflected off the individual of interest. See, for example, U.S. Pat. No. 7,272, 431 to McGrath, "Remote-sensing Method and Device," and US Patent Application Nos. 2004/0123667 to McGrath, "Remote-sensing Method and Device," and 2008/0045832 to McGrath, "Remote-sensing Method and Device," which are each incorporated herein by reference. As used herein, "non-visual information" can include, for example, information derived from chemicals present in an individual's breath and indicating the physiological state of the individual. For example, ketones and acetone have been used as indicators of an insulin insufficiency in diabetic individuals. A sensor configured to acquire information regarding specific breath components of an individual at a given time can be utilized by the system as an indicator of physiological distress. See, for example, U.S. Pat. No. 6,841,391 to Lewis et al., "Medical Applications of Artificial Olfactometry," and U.S. Pat. No. 7,261,857 to Suslick et al., "Colorimetric Artificial Nose having an Array of Dyes and Method for Artificial Olfaction," as well as US Patent Application No. 2010/0166604, to Lim et al., "Colorimetric Sensor Arrays Based on Nanoporous Pigments," which are each incorporated by reference herein. Also by way of example, levels of nitric oxide, nitric dioxide and carbon dioxide, as well as the ratios fo these gasses, have been used as indicators of an imminent asthma attack in some at-risk individuals. A sensor configured to acquire information regarding specific breath components of an individual at a given time can be utilized by the system as an indicator of physiological risk. See, for example: US Patent Application Nos. 2007/0048180 to Gabriel et al., "Nanoelectronic breath analyzer and asthma monitor;" 2007/0048181 to Chang et al., "Carbon dioxide nanosensor and respiratory CO2 monitors;" 2006/0055392 to Passmore et al., "Remotely communicating, battery-powered nanostructure sensor devices;" 2008/0050839 to Suslick and McNamara, "Apparatus and method for detecting lung cancer using exhaled breath;" and International Application No. PCT/US2007/010836 to Gabriel et al., "Nanoelectronic breath analyzer and asthma monitor;" which are each incorporated herein by reference. See also Kuzmych et al., "Carbon nanotube sensors for exhaled breath components," Nanotechnology 18 (2007), which is incorporated by reference herein. Similarly, as used herein, "non-visual data," as used herein, refers to data that is acquired from the detection of a non-visual event, such as a sound, a temperature, a vibration, a wave in a non-visual frequency, or other non-visual sources such as those described herein.

There is at least one monitoring device 110 in the area nearby to the individual 100 during the periodic medication events. The at least one monitoring device 110 is capable of acquiring visual as well as non-visual data during the administration of medication 105 to the individual 100 (i.e. the medication event) and transmitting this data to a computer system 120. The monitoring device can be a dedicated device or it can be included as part of a multi-functional device. For example, a monitoring device can include a tablet computer, laptop, smartphone, or similar device. The monitoring device can be a mobile device. The monitoring device can be a fixed-position device, or a device that is designed to be fixed to a particular location. For example, the monitoring device can be a digital camera device configured to be affixed to a wall. The monitoring device 110 can include at least one camera unit that is capable of acquiring visual and non-visual data. For example, a monitoring device can include a portable computing device including a camera unit that can acquire data from the near-infrared (IR) spectrum as well as the visual spectrum. For example, a monitoring device can include a portable computing device including a camera unit and a microphone unit. For example, a monitoring device can include a portable computing device including a camera unit and a RFID transceiver. In some embodiments, the at least one monitoring device 110 can also include other features, such as a keyboard 160 and a screen 155. In some embodiments, there are a plurality of monitoring devices.

A monitoring device 110 processes the visual and non-visual data acquired during a medication event and transmits processed information to a computer system 120. In some embodiments, at least one monitoring device 110 transmits signals 115 via wireless communication to a computer system 120. In some embodiments, at least one monitoring device 110 transmits signals 115 via a wired connection to a computer system 120. In some embodiments, the at least one monitoring device 110 is configured to receive signals 150 transmitted from the computer system 120. In some embodiments, at least one monitoring device 110 is configured to receive signals 150 transmitted from the computer system 120 via wireless communication. In some embodiments, at least one monitoring device 110 is configured to receive signals 150 transmitted from the computer system 120 via a wired connection. For example, the at least one monitoring device 110 can be configured to receive transmission signals 150 over a telephone wire, an optical fiber cable, or a dedicated signal transmission wire.

A system 120 includes one or more computing devices functionally integrated to operate together. For example, a system 120 can include one or more main computing units 125 as well as one or more secondary computing units 130. A system 120 can include one or more secondary computing units 130 configured to be operable by a user 140, such as a member of the medical caregiver team. A system 120 can include one or more mobile computing devices 135 configured to be operable by a user 145, such as a member of the medical caregiver team. Although users 140, 145 is shown/described herein as a single illustrated figure, users 140, 145 may be representative of a human user, a robotic user (e.g., computational entity), and/or substantially any combination thereof (e.g., a user may be assisted by one or more robotic agents) unless context dictates otherwise. In general, the same may be said of "sender" and/or other entity-oriented terms as such terms are used herein unless context dictates otherwise. A mobile computing device 135 can be integrated with a multipurpose mobile computing device, such as a smartphone, PDA, tablet or communication device. The computing devices 125, 130, 135 of a system 120 are configured to be able to send and receive information in the form of signals between the computing devices 125, 130, 135. The computing devices 125, 130, 135 of a system 120 can include input devices, such as keyboards, computer mices, or touchpads. The computing devices 125, 130, 135 of a system 120 can include devices to present results visually to a system user 140, 145 such as monitors, lights, or displays. The computing devices 125, 130, 135 of a system 120 can include devices that present results or alert system users 140, 145 of results through non-visual means, such as buzzers, speakers, and vibratory elements. In some embodiments, there may be a dedicated alert device, such as a light or audible alarm, attached to the computer system 120. The computing devices 125, 130, 135 of a system 120 can include memory devices integral to or attached. For example, a main computing unit 125 or a secondary computing unit 130, 135 can include internal computer memory. For example, a main computing unit 125 or a secondary computing unit 130, 135 can be attached to an additional device configured to store computer memory. The computer system 120 can include one or more transmission devices, including, for example, transmitters, receivers, or transceivers. The transmission devices of the system 120 can be configured to transmit and receive information between components of the system (e.g. a main computing unit 125 and a secondary computing unit 135) or to another device (e.g. a monitoring device 110).

An individual 100, such as shown in FIG. 1, has a personalized medication regimen preset by one or more members of the medical caregiver team (e.g. users 140 and 145). The medication regimen includes instructions for the administration of a specific dose of a medication 105 at a particular time or within a time window, or a medication event. At least one monitoring device 110 is positioned in the vicinity of the individual 100 at an orientation and distance to generate both visual and non-visual data regarding the medication event. In some embodiments, the individual 100 can operate the at least one monitoring device 110, such as turning it on, positioning it, etc. In some embodiments, the individual 100 does not operate the at least one monitoring device 110. For example, the monitoring device 110 may be a fixed-position device that is not turned on and off by the individual 100.

FIG. 2 illustrates further aspects of the systems and methods described herein. FIG. 2 illustrates diagram of aspects of a system for monitoring medication events relating to an individual. The system can be a computer system such as depicted in FIG. 1 and described herein. The system 200 depicted in FIG. 2 includes electrical circuitry. The circuitry of the system 200 is configured to carry out a series of logical processes. As illustrated in FIG. 2, a system 200 for monitoring medication events relating to an individual includes one or more circuitry components 210, 220, 230, 240, 250, 260, 270, 280. The circuitry is configured to carry out specific processes.

The system 200 includes circuitry 210 for analyzing received data for an identifier of a first medication event for an individual. An identifier of a first medication event is a predetermined identifier of the medication event. For example, the system can analyze received data for a personal identifier, such as a name, patient ID number, or identifying code. For example, the system can analyze received data for a visually apparent identifier, such as a bar code, a matrix barcode, or visual features of a medication label. For example, the system can analyze received data for a non-visually apparent identifier, such as a auditory signal like the individual stating his or her medication, the individual stating a specific phrase, such as "I am taking my medication now," or a particular sound. For example, the system can analyze received data for a non-visually apparent identifier, such as a RFID identifier specific to a medication label. In some embodiments, there can be more than one identifier of a first medication event for an individual. For example, the system can be preset to recognize either a bar code or a RFID identifier specific to a medication label as an identifier. In some embodiments, there can be a combination of features to form the identifier of a first medication event for an individual. For example, the identifier can include visual data from a bar code on the medication label in combination with auditory data including the individual stating "I am taking my medication now."

The system 200 includes circuitry 220 for analyzing the received data for at least one attribute of the individual. An "attribute of the individual," as used herein, is a predetermined attribute identifiable by the system in the received data that identifies the specific individual(s) detected by the monitoring device and included in the transmitted data from the monitoring device. For example, an attribute of the individual can include a visually apparent aspect of the individual to whom the medication is administered, such as aspects of the facial features of the individual. For example, an attribute of the individual can include a non-visually apparent aspect of the individual to whom the medication is administered, such as a code identifier from a keypad or other input device. For example, an attribute of the individual can include audio data of the individual stating his or her name. For example, an attribute of the individual can include a RFID code from an object associated with the individual (such as a card or bracelet) and scanned by a monitoring device. For example, an attribute of the individual can include an image of a fingerprint of the individual. For example, an attribute of the individual can include facial attributes (e.g. eye color, distance between eyes, nose shape, etc.) or other biometric attributes. In some embodiments, there can be more than one attribute of the individual. For example, the system can be preset to recognize either a bar code or a RFID identifier specific to an individual's identification card or tag as an attribute associated with the individual by the system. In some embodiments, there can be a combination of features to form the attribute of the individual. For example, an attribute of the individual can include visual data from a bar code on a patient ID tag in combination with auditory data including the individual stating his or her name.

The system 200 includes circuitry 230 for analyzing the received data for at least one attribute relating to a medication during the first medication event. An attribute relating to a medication during the first medication event is an predetermined attribute of the medication that is detected during the first medication event. For example, an attribute relating to a medication during the first medication event can include a visual aspect of the medication, such as pill color, in combination with time data that identifies the attribute of the medication as detected during the first medication event.

The system 200 includes circuitry 240 for analyzing the received data for at least one feature of visual information relating to the individual during the first medication event. A feature of visual information relating to the individual during the first medication event is an predetermined feature of visual information relating to the individual that is detected during the first medication event. For example, a feature of visual information can include visual images of the individual placing one or more pills into his or her mouth and then swallowing the pills, in combination with time data. For example, a feature of visual information can include visual images of the individual placing an inhaler in his or her mouth and activating the inhaler, in combination with time data.

The system 200 includes circuitry 250 for analyzing the received data for at least one feature of non-visual information relating to the individual during the first medication event. A feature of non-visual information relating to the individual during the first medication event is an predetermined feature of non-visual information relating to the individual that is detected during the first medication event. For example, a feature of non-visual information can include the sounds of the individual swallowing the pills, in combination with time data. For example, a feature of visual information can include auditory data of the individual placing an inhaler in his or her mouth and activating the inhaler, in combination with time data.

The system 200 includes circuitry 260 for analyzing the received data for a time associated with the first medication event. A time associated with a medication event is a predetermined time within a time window as part of a preset medication regimen. For example, a time associated with a medication event can be a time within a time window of when the medication event should occur in accord with the medication regimen. For example, the time associated with a medication event can be a clock time, such as "between 4 and 430 PM." For example, the time associated with a medication event can be a relative time, such as "3 to 4 hours after the end of the last medication event."

The system 200 includes circuitry 270 for determining a compliance likelihood for the first medication event based on the analyses of the received data. The standards for determining a compliance likelihood are predetermined and specific to a particular medication event or type of medication events for an individual. For example, a compliance likelihood can be determined from a series of binary indicators regarding the analyses of the circuitry previously described, 210, 220, 230, 240, 250, 260. For example, a compliance likelihood can be determined from a table of attributes and features of the medication, the individual, and the medication event that should be present in data obtained by the monitoring device during a medication regimen compliant medication event. For example, if all attributes and features of the medication, the individual, and the medication event are present in the data from the monitoring device, the compliance likelihood can be determined to be high, with a value such as 1 or 100%. For example, if all attributes and features of the medication, the individual, and the medication event are not present in the data from the monitoring device, the compliance likelihood can be determined to be less than high, or less than 1 or less than 100%.

The system 200 includes circuitry 280 for indicating the determined compliance likelihood for the first medication event. For example, the circuitry can be configured to indicate the determined compliance likelihood on the display of a computing device that is part of the system (e.g. the remote device 135 of FIG. 1).

FIG. 3 illustrates other aspects of the system 200 depicted in FIG. 2. As shown in FIG. 3, in some embodiments the circuitry 210 for analyzing received data for an identifier of a first medication event for an individual includes additional aspects. FIG. 3 illustrates that in some embodiments the circuitry 210 for analyzing received data for an identifier of a first medication event for an individual includes circuitry 300 for analyzing received data encoded in a transmission originating from a cell phone. For example, a cell phone can be utilized by the individual as a monitoring device (e.g. monitoring device 110 of FIG. 1) to obtain visual and non-visual data during the first medication event. Subsequently, the data regarding the medication event can be transmitted from the cell phone to the system for processing and analysis. The system can include circuitry 300 for analyzing the received data encoded in a transmission originating from the cell phone. FIG. 3 also shows that in some embodiments the circuitry 210 for analyzing received data for an identifier of a first medication event for an individual can include circuitry 310 for analyzing received data encoded in a transmission originating from a portable computing device. For example, a portable computing device, such as a laptop, tablet, or PDA, can be utilized by the individual as a monitoring device (e.g. monitoring device 110 of FIG. 1) to obtain visual and non-visual data during the first medication event. Subsequently, the data regarding the medication event can be transmitted from the portable computing device to the system for further data processing and analysis. The system can include circuitry 310 for analyzing the received data encoded in a transmission originating from the portable computing device. FIG. 3 depicts that the circuitry 210 for analyzing received data for an identifier of a first medication event for an individual can include, in some embodiments, circuitry 320 for analyzing received data encoded in a transmission from a fixed position camera unit. For example, a fixed position camera unit can be affixed to a wall or furnishing. A fixed position camera unit can be configured as a monitoring device (e.g. monitoring device 110 of FIG. 1) to obtain visual and non-visual data during the first medication event. For example, the fixed position camera unit can be configured to turn on at the appropriate times to obtain data regarding a medication event. Data obtained from a fixed position camera unit can be processed and transmitted to the system 200 for monitoring medication events relating to an individual. FIG. 3 shows that, in some embodiments, the circuitry 210 for analyzing received data for an identifier of a first medication event for an individual can include circuitry 330 for analyzing received data for an identifier that includes a code. For example, the circuitry 210 for analyzing received data for an identifier of a first medication event for an individual can include circuitry 330 for analyzing received data for an identifier that includes a code such as an RFID code, a patient identification code, a code identifying the source of the data (e.g. a cell phone number or location code for a fixed position camera unit) or other codes. An identifier that includes a code can include an identifier of the source of the data (e.g. a cell phone or a fixed position camera unit). An identifier that includes a code can include an identifier of the individual, for example a patient ID code or a RFID code associated with the individual. An identifier that includes a code can include an identifier of the medication event, such as a code identifying the specific type of medication event. An identifier that includes a code can include an identifier of the medication, such as a Q code scanned from the medication label. The code can include an alphanumeric code, a binary code, or other types of codes. FIG. 3 depicts that, in some embodiments, the circuitry 210 for analyzing received data for an identifier of a first medication event for an individual can include circuitry 340 for analyzing the received data for an identifier that includes at least one visual information feature. For example, the circuitry 340 for analyzing the received data for an identifier that includes at least one visual information feature can include circuitry for identifying a visual information feature of the medication, such as the shape and color of a specific type of pills, or the label from a medication container. For example, the circuitry 340 for analyzing the received data for an identifier that includes at least one visual information feature can include circuitry for identifying a visual information feature of the individual, such as facial aspects, coloring, or visual aspects of a tag worn by the individual. For example, the circuitry 340 for analyzing the received data for an identifier that includes at least one visual information feature can include circuitry for identifying a temporal visual information feature, such as the identification of a time from the visual information of a wall clock.

FIG. 4 illustrates other aspects of the system 200 depicted in FIG. 2. As shown in FIG. 4, in some embodiments the circuitry 210 for analyzing received data for an identifier of a first medication event for an individual can include circuitry 400 for analyzing the received data for an identifier that includes at least one non-visual information feature. For example, the identifier of a first medication event can include an identifier that includes an identifier with audio information. For example, an identifier of a first medication event for the individual that includes at least one non-visual information feature can include aspects of an audio recording of the individual saying "I am taking my medication now." For example, an identifier of a first medication event for the individual that includes at least one non-visual information feature can include aspects of an audio recording of a tone, beep or other sound originating from the monitoring device (e.g. 110 in FIG. 1). For example, an identifier of a first medication event for the individual that includes at least one non-visual information feature can include aspects of an audio recording of a sound from a medication administration device, such as an inhaler being used. For example, the identifier of a first medication event can include an identifier that includes an identifier with near-IR information. For example, an identifier of a first medication event for the individual that includes at least one non-visual information feature can include aspects of the near-IR readings of an individual's throat as he or she is swallowing a medication.

FIG. 4 also depicts that, in some embodiments, the circuitry 210 for analyzing received data for an identifier of a first medication event for an individual can include circuitry 410 for analyzing the received data for a radio-frequency identification (RFID) code. For example, the identifier of a first medication event can include an identifier that includes an identifier such as an RFID code that the system can associate with the medication event.

FIG. 4 further illustrates that, in some embodiments, circuitry 220 for analyzing the received data for at least one attribute of an individual includes circuitry 420. Circuitry 420 includes: circuitry for associating the identifier of the first medication event with an expected individual; circuitry for retrieving one or more specific identifiers associated with the expected individual; circuitry for analyzing the received data for the presence or absence of at least one of the one or more specific identifiers; and circuitry for indicating the presence or absence of the expected individual based on the analysis. For example, circuitry 420 can include circuitry for associating the identifier of the first medication event with an expected individual; circuitry for retrieving one or more specific identifiers associated with the expected individual, such as visual identifiers of the individual's body or face; circuitry for analyzing the received data for the presence or absence of at least one of the one or more specific identifiers of the individual's body or face; and circuitry for indicating the presence or absence of the expected individual based on the analysis. For example, if visual identifiers of the expected individual's face are not present in the received data, the circuitry can indicate the absence of the expected individual. For example, circuitry 420 can include circuitry for associating the identifier of the first medication event with an expected individual; circuitry for retrieving one or more specific identifiers associated with the expected individual, such as an identification code that was entered onto the keypad of a monitoring device; circuitry for analyzing the received data for the presence or absence of at least one of the one or more specific identifiers of the expected individual, such as a personal identification code; and circuitry for indicating the presence or absence of the expected individual based on the analysis.

FIG. 5 illustrates further aspects of the system 200 shown in FIG. 2. FIG. 5 depicts that, in some embodiments, circuitry 220 for analyzing the received data for at least one attribute of an individual includes circuitry 500. Circuitry 500 includes circuitry for associating the identifier of the first medication event with an expected medication; circuitry for retrieving one or more attributes associated with the expected medication; circuitry for comparing the retrieved one or more attributes associated with the expected medication with the received data; circuitry for determining, based on the comparison, a confirmation likelihood for the expected medication; and circuitry for indicating the determined confirmation likelihood for the expected medication. For example, in some embodiments, circuitry 500 can include circuitry for associating the identifier of the first medication event with an expected medication; circuitry for retrieving one or more attributes associated with the expected medication, such as visual attributes of pill color and shape; circuitry for comparing the retrieved one or more attributes associated with the expected medication with the received data; circuitry for determining, based on the comparison, a confirmation likelihood for the expected medication; and circuitry for indicating the determined confirmation likelihood for the expected medication. The confirmation likelihood can be presented in different forms depending on the requirements of the embodiment, such as a scale, a percent, a numerical value, a color gradient, or other representation. For example, in some embodiments, circuitry 500 can include circuitry for associating the identifier of the first medication event with an expected medication; circuitry for retrieving one or more attributes associated with the expected medication, such as an expected RFID code from the medication label; circuitry for comparing the retrieved one or more attributes associated with the expected medication with the received data; circuitry for determining, based on the comparison, a confirmation likelihood for the expected medication; and circuitry for indicating the determined confirmation likelihood for the expected medication.

FIG. 6 shows further aspects of the system 200 shown in FIG. 2. FIG. 6 illustrates that, in some embodiments, circuitry 220 for analyzing the received data for at least one attribute of an individual includes circuitry 600 for analyzing the received data for at least one attribute of the individual; circuitry for comparing the at least one attribute of the individual with a set of attribute parameters for an expected individual; and circuitry for determining, based on the comparison, an attribute score for the at least one attribute of the individual. For example, in some embodiments the circuitry 220 for analyzing the received data for at least one attribute of an individual can include circuitry 600 for analyzing the received data for at least one attribute of the individual, such as visual attributes of facial structure; circuitry for comparing the at least one visual attributes of facial structure of the individual with a set of parameters for visual attributes of facial structure for an expected individual; and circuitry for determining, based on the comparison, an attribute score for the visual attributes of facial structure of the individual. For example, the circuitry 600 can be configured to compare eye color, distance between eye sockets, nose shape, and other visual facial features with a set of parameters for visual attributes of facial structure for an expected individual. The system can also include circuitry for determining, based on the comparison, an attribute score for the visual attributes of facial structure of the individual and circuitry for displaying the determination in a visual format such as a graph, table, numerical score, or other visual format. For example, in some embodiments the circuitry 220 for analyzing the received data for at least one attribute of an individual can include circuitry 600 for analyzing the received data for at least one attribute of the individual, such as audio features of a voice recording; circuitry for comparing the at least one audio features of a voice recording of the individual with a set of parameters for audio features of a voice recording for an expected individual; and circuitry for determining, based on the comparison, an attribute score for the audio features of a voice recording of the individual. For example, the circuitry 600 can be configured to compare the tone, cadence, pitch, and other audio features of a voice recording with a set of parameters for audio features of a voice recording for an expected individual. The system can also include circuitry for determining, based on the comparison, an attribute score for the audio features of a voice recording of the individual and circuitry for displaying the determination in a visual format such as a graph, table, numerical score, or other visual format. For example, in some embodiments the circuitry 220 for analyzing the received data for at least one attribute of an individual can include circuitry 600 for analyzing the received data for at least one attribute of the individual, such as an identifier code typed onto a touchpad of a monitoring device (e.g. item numbered 110 in FIG. 1); circuitry for comparing the input identifier code of the individual with a set of parameters for identifier codes for an expected individual, such as with a look-up table; and circuitry for determining, based on the comparison, an attribute score for the identifier code of the individual. The system can also include circuitry for determining, based on the comparison, an attribute score for the identifier code of the individual and circuitry for displaying the determination in a visual format such as a graph, table, numerical score, or other visual format.

FIG. 7 illustrates aspects of the system 200 shown in FIG. 2. FIG. 7 illustrates that, in some embodiments, circuitry 230 for analyzing the received data for at least one attribute relating to a medication during the first medication event includes circuitry 700 for analyzing the received data for an attribute that includes at least one visual information feature. For example, the attribute of the medication that includes at least one visual information feature can include the color and shape of the medication delivery device, visual aspects of the medication label, the color and shape of pills or capsules, or other visual attributes of the medication. FIG. 7 also shows that, in some embodiments, circuitry 230 for analyzing the received data for at least one attribute relating to a medication during the first medication event includes circuitry 710 for analyzing the received data for an attribute that includes at least one non-visual information feature. For example, the circuitry can be configured to analyze the received data for a non-visual attribute such as a RFID code from the medication label, the sound of an inhaler in use, or the near-IR reflection of the medication label or packaging. FIG. 7 further illustrates that, in some embodiments, circuitry 230 for analyzing the received data for at least one attribute relating to a medication during the first medication event includes circuitry 720 analyzing the received data for an attribute that includes a radio-frequency identification (RFID) code. For example, a monitoring device (e.g. item numbered 110 in FIG. 1) can be configured to scan a medication label or packaging with a RF signal, and to accept a return signal with RFID information.

FIG. 8 shows aspects of the system 200 illustrated in FIG. 2. FIG. 8 illustrates that, in some embodiments, circuitry 230 for analyzing the received data for at least one attribute relating to a medication during the first medication event includes circuitry 800 for analyzing the received data for at least one attribute of the medication; circuitry for comparing the at least one attribute of the medication with a set of attribute parameters for an expected medication; and circuitry for determining, based on the comparison, an attribute score for the at least one attribute of the medication. For example, circuitry 800 can include: circuitry configured to analyze the received data for pill color and number; circuitry configured to compare the pill color and number with a set of attribute parameters for an expected medication, including pill number and color; and circuitry for determining, based on the comparison, an attribute score for the pill number and color. The system can also include circuitry for displaying the determined attribute score in a visual format such as a graph, table, numerical score, or other visual format.

FIG. 9 depicts aspects of the system 200 illustrated in FIG. 2. FIG. 9 shows that, in some embodiments, circuitry 230 for analyzing the received data for at least one attribute relating to a medication during the first medication event includes circuitry 900 for associating the identifier of the first medication event with an expected medication; circuitry for retrieving one or more specific identifiers associated with the expected medication; circuitry for analyzing the received data for the presence or absence of at least one of the one or more specific identifiers; and circuitry for indicating the presence or absence of the expected medication based on the analysis. For example, in some embodiments the circuitry 900 includes circuitry for associating the identifier of the first medication event, such as visual information from a medication label, with an expected medication; circuitry for retrieving one or more specific identifiers associated with the expected medication, such as dispenser shape and size; circuitry for analyzing the received data for the presence or absence of at least one of the one or more specific identifiers, such as the dispenser shape or size; and circuitry for indicating the presence or absence of the expected medication based on the analysis. The circuitry for indicating the presence or absence of the expected medication based on the analysis can include circuitry for a graphical indicator, such as a chart, table, text, or graph on a display. The circuitry for indicating the presence or absence of the expected medication based on the analysis can include circuitry for a light indicator, such as a green light indicator.

FIG. 10 shows aspects of the system 200 illustrated in FIG. 2. FIG. 10 illustrates that, in some embodiments, circuitry 230 for analyzing the received data for at least one attribute relating to a medication during the first medication event includes circuitry 1000. Circuitry 1000 includes: circuitry for associating the identifier of the first medication event with an expected medication; circuitry for retrieving one or more attributes associated with the expected medication; circuitry for comparing the retrieved one or more attributes associated with the expected medication with the received data; circuitry for determining, based on the comparison, a confirmation likelihood for the expected medication; and circuitry for indicating the determined confirmation likelihood for the expected medication. For example, circuitry 1000 can include: circuitry for associating the identifier of the first medication event, such as the audio recording of the individual saying "I am taking medication XYZ now," with an expected medication; circuitry for retrieving one or more attributes associated with the expected medication "XYZ," such as visual aspects of the medication label; circuitry for comparing the retrieved visual aspects of the medication label associated with the expected medication "XYZ" with the received data; circuitry for determining, based on the comparison, a confirmation likelihood for the expected medication "XYZ" for the specific medication event; and circuitry for indicating the determined confirmation likelihood for the expected medication "XYZ." For example, circuitry 1000 can include: circuitry for associating the identifier of the first medication event, such as the visual aspects of the medication label, with an expected medication; circuitry for retrieving one or more attributes associated with the expected medication, such as expected visual aspects of the medication label; circuitry for comparing the retrieved visual aspects of the medication label associated with the expected medication with the received data; circuitry for determining, based on the comparison, a confirmation likelihood for the expected medication for the specific medication event; and circuitry for indicating the determined confirmation likelihood for the expected medication. For example, the system can be configured to indicate the determined confirmation likelihood for the expected medication to a medical professional using the system, (e.g. illustrated as 140 and 145 in FIG. 1). The determined confirmation likelihood can be indicated in a light on/light off format, such as a red light or a green light. The determined confirmation likelihood can be indicated in a text, graph, or other format. In some embodiments, the system can include circuitry for initiating an alarm based on the determined confirmation likelihood, such as if the determined confirmation likelihood is below a threshold amount. Such circuitry can, for example, serve as a warning system for an individual or medical caregivers to indicate that the incorrect medication has been administered during the medication event.

FIG. 11 shows aspects of the system 200 depicted in FIG. 2. FIG. 11 illustrates that, in some embodiments, circuitry 240 for analyzing the received data for at least one feature of visual information relating to the individual during the first medication event can include circuitry 1100. Circuitry 1100 includes: circuitry for identifying a visual information component of the received data; circuitry for comparing the identified visual information component of the received data with at least one visual information parameter; and circuitry for determining a likelihood of sufficiency for the visual information component of the received data based on the comparison. For example, circuitry 1100 can include: circuitry for identifying a visual information component of the received data, such as facial features; circuitry for comparing the identified facial features component of the received data with at least one facial feature parameter; and circuitry for determining a likelihood of sufficiency for the facial feature component of the received data based on the comparison. For example, the circuitry 1100 can be configured to determine the likelihood of sufficiency for the facial feature component of the received data in order to confirm that the individual has taken his or her medication (i.e. not "spoofing" the medication event). In some embodiments, circuitry 240 can include circuitry for indicating the determined likelihood of sufficiency for the visual information component of the received data to at least one system user, (e.g. illustrated as 140 and 145 in FIG. 1). Circuitry for indicating the determined likelihood of sufficiency for the visual information component of the received data to at least one system user can include circuitry for depicting a graph, a table, text, or a light indicator. The determined likelihood of sufficiency for the visual information component of the received data can be utilized by the system user, such as a medical caregiver, to determine if the visual information component of the medication event is sufficient to ensure aspects of the medication event happened correctly, such as the medication label was identified, the medication was identified, the individual took the medication correctly, etc.

FIG. 12 shows aspects of the system 200 depicted in FIG. 2. FIG. 12 illustrates that, in some embodiments, circuitry 240 for analyzing the received data for at least one feature of visual information relating to the individual during the first medication event can include circuitry 1200. Circuitry 1200 includes: circuitry for associating the identifier of the first medication event with a set of visual information parameters for a standard medication event; circuitry for comparing the at least one feature of visual information relating to the individual during the first medication event with the set of visual information parameters for the standard medication event; circuitry for determining, based on the comparison, a medication event compliance score for the first medication event; and circuitry for indicating the determined medication event compliance score for the first medication event. For example, in some embodiments circuitry 1200 can include: circuitry for associating the identifier of the first medication event, such as visual features of the individual, with a set of visual information parameters, such as visual features of the individual for a standard medication event; circuitry for comparing the at least one feature of visual information relating to the individual during the first medication event with the set of visual information parameters for the standard medication event; circuitry for determining, based on the comparison, a medication event compliance score for the first medication event; and circuitry for indicating the determined medication event compliance score for the first medication event. In some embodiments, the circuitry for indicating the determined medication event compliance score for the first medication event can include circuitry for indicating a graph, table, text score, or other visual indicator.

FIG. 13 shows aspects of the system 200 illustrated in FIG. 2. FIG. 13 shows that, in some embodiments, circuitry 250 for analyzing the received data for at least one feature of non-visual information relating to the individual during the first medication event includes one or more of circuitry 1300, 1310, 1320 and 1330. FIG. 13 illustrates that circuitry 1300 includes: circuitry for analyzing the received data for the at least one feature of the non-visual information including near-infrared (IR) information. For example, circuitry 1300 can include for analyzing the received data for near-infrared (IR) information regarding the medication event. For example, circuitry 1300 can include for analyzing the received data for near-infrared (IR) information associated with the individual's throat during the medication event, which can serve to validate the medication administration such as with a positional shift during swallowing. For example, circuitry 1300 can include: circuitry for analyzing the received data for near-infrared (IR) information associated with the individual's skin adjacent to administration of a medication via syringe during the medication event, which can serve to validate the medication administration such as with a skin flush after injection of the medication. FIG. 13 further illustrates that circuitry 1310 includes: circuitry for analyzing the received data for the at least one feature of the non-visual information including auditory information. For example, in some embodiments circuitry 1310 can include circuitry for analyzing the received data for auditory information, such as auditory information relating to the individual swallowing, or using an inhaler. FIG. 13 also shows that circuitry 1320 includes: circuitry for analyzing the received data for the at least one feature of the non-visual information including thermal information. For example, in some embodiments circuitry 1320 can include circuitry for analyzing the received data for thermal information associated with the individual's skin adjacent to administration of a medication via syringe during the medication event, which can serve to validate the medication administration such as with a temperature shift after injection of the medication. For example, in some embodiments circuitry 1320 can include circuitry for analyzing the received data for thermal information associated with the individual's throat during the medication event, which can serve to validate the medication administration such as with a temperature change during swallowing. FIG. 13 also depicts that circuitry 250 can include circuitry 1330 for analyzing the received data for the at least one feature of the non-visual information including kinetic information. For example, circuitry 1330 can include circuitry for analyzing the received data for kinetic information, such as the movement of a syringe or inhaler during the medication event. For example, circuitry 1330 can include circuitry for analyzing the received data for kinetic information, such as the motion of the individual to place the syringe for medication administration.

FIG. 14 shows aspects of the system as illustrated in FIG. 2. FIG. 14 shows that, in some embodiments, circuitry 250 for analyzing the received data for at least one feature of non-visual information relating to the individual during the first medication event includes one or more of circuitry 1400, 1410. Circuitry 1400 includes: circuitry for analyzing the received data for the at least one feature of the non-visual information including micropower impulse radar (MIR) information. For example, circuitry 1400 can include circuitry for analyzing the received data for information including micropower impulse radar (MIR) information, such as MIR information relating to the medication administration to the individual and associated physiological effects. See: "Micropower Impulse Radar," Azevedo and McEwan, Science and Technology Review, January/February 1996, pages 17-29; and US Patent Application Publications No. 2004/0249257 and 2004/0249258 to Tupin et al., each titled "Article of Manufacture for Extracting Physiological Data Using Ultra-Wideband Radar and Improved Signal Processing Techniques," which are all incorporated by reference herein. See also: US Patent Application Publication No.

2009/0227882 to Foo, titled "Ultra Wideband Monitoring Systems and Antennas," which is incorporated by reference herein. Circuitry 1410 includes: circuitry for identifying a non-visual information component of the received data; circuitry for comparing the identified non-visual information component of the received data with at least one non-visual information parameter; and circuitry for determining a likelihood of sufficiency for the non-visual information component of the received data based on the comparison. For example, some embodiments of the system can include circuitry for identifying an audio component of the received data; circuitry for comparing the identified audio component of the received data with at least one audio information parameter; and circuitry for determining a likelihood of sufficiency for the audio information component of the received data based on the comparison. For example, the audio information parameter can include a decibel range for audio information, or a signal strength parameter. For example, some embodiments of the system can include circuitry for identifying a RFID signal component of the received data; circuitry for comparing the identified RFID signal component of the received data with at least one RFID signal parameter; and circuitry for determining a likelihood of sufficiency for the RFID signal component of the received data based on the comparison. For example, the RFID signal parameter can include a signal strength or signal quality parameter.

FIG. 15 shows further aspects of the system 200 illustrated in FIG. 2. FIG. 15 shows that, in some embodiments circuitry 250 for analyzing the received data for at least one feature of non-visual information relating to the individual during the first medication event includes: circuitry 1500 for identifying a non-visual information component of the received data; circuitry for comparing the identified non-visual information component of the received data with at least one non-visual information parameter; and circuitry for determining a likelihood of sufficiency for the non-visual information component of the received data based on the comparison. For example, circuitry 1500 can include circuitry for identifying an audio information component of the received data; circuitry for comparing the identified audio information component of the received data with at least one audio information parameter; and circuitry for determining a likelihood of sufficiency for the audio information component of the received data based on the comparison. For example, the at least one audio information parameter can include at least one of: a duration of the audio information, a decibel minimum and maximum for the audio information, and a tone range for the audio information.

FIG. 16 illustrates further aspects of the system 200 shown in FIG. 2. FIG. 16 depicts that, in some embodiments, circuitry 260 for analyzing the received data for a time associated with the first medication event includes circuitry 1600. Circuitry 1600 includes: circuitry for identifying a time component in the received data; circuitry for comparing the identified time component with at least one time parameter associated with an expected medication event for the individual; and circuitry for determining, based on the comparisons, a time score for the first medication event based on the received data. For example, in some embodiments, circuitry 1600 can include: circuitry for identifying a clock time in the received data; circuitry for comparing the identified clock time with at least one time range parameter associated with an expected medication event for the individual (i.e. the expected time range for the medication to be taken based on the medication regimen); and circuitry for determining, based on the comparisons, a time score for the first medication event based on the received data. A time score can include a range, or binary (e.g. yes/no) score. In some embodiments, the system includes circuitry for indicating the determined time score. For example, the determined time score can be indicated in a text, table, graph or color indicator (e.g. red light/green light) format. For example, the determined time score can be indicated on a device utilized by at least one system user, (e.g. illustrated as 140 and 145 in FIG. 1).

FIG. 17 shows aspects of the system 200 illustrated in FIG. 2. FIG. 17 depicts that, in some embodiments, circuitry 260 for analyzing the received data for a time associated with the first medication event includes circuitry 1700. Circuitry 1700 includes: circuitry for identifying a time component in the received data; circuitry for associating the identifier of a first medication event for an individual with an expected medication time for the individual; circuitry for comparing the identified time component with the expected medication time; circuitry for determining, based on the comparison, a medication event time compliance score for the first medication event; and circuitry for indicating the determined medication event time compliance score for the first medication event. For example, circuitry 1700 can include: circuitry for identifying an elapsed time since the last medication event in the received data; circuitry for associating the identifier of a first medication event for an individual with an expected medication time for the individual; circuitry for comparing the identified elapsed time since the last medication event with the expected medication time; circuitry for determining, based on the comparison, a medication event time compliance score for the first medication event; and circuitry for indicating the determined medication event time compliance score for the first medication event. In some embodiments, the system includes circuitry for indicating the determined medication event time compliance score. For example, the determined medication event time compliance score can be indicated in a text, table, graph or color indicator (e.g. red light/yellow light/green light) format. For example, the determined medication event time compliance score can be indicated on a device utilized by at least one system user, (e.g. illustrated as 140 and 145 in FIG. 1).

FIG. 18 illustrates aspects of the system 200 shown in FIG. 2. FIG. 18 illustrates that, in some embodiments, circuitry 270 for determining a compliance likelihood for the first medication event based on the analyses of the received data includes circuitry 1800 and/or circuitry 1810. Circuitry 1800 includes: circuitry for comparing the analyses with a set of parameters for a standard medication event; and circuitry for calculating, based on the comparison, a compliance likelihood for the first medication event. For example, in some embodiments circuitry 1800 includes circuitry for comparing one or more of the analyses with a set of parameters for a standard medication event; and circuitry for calculating, based on the comparison, a compliance likelihood for the first medication event. For example in some embodiments circuitry 1800 includes circuitry for comparing one or more of: the analysis of the received data for at least one attribute of an individual; the analysis of received data for at least one attribute relating to a medication during the first medication event; the analysis of the received data for at least one feature of visual information relating to the individual during the first medication event; the analysis of the received data for at least one feature of non-visual information relating to the individual during the first medication event; and the analysis of the received data for a time associated with the first medication event; and circuitry for calculating, based on the comparison, a compliance likelihood for the first medication event. Circuitry for calculating, based on the comparison, a compliance likelihood for the first medication event can include, for example, calculations based on the analysis results, underlying data or input parameters. Circuitry 1810 includes: circuitry for comparing the analyses with a set of parameters for an expected medication event for the individual; and circuitry for calculating, based on the comparison, a compliance likelihood for the individual with the expected medication event. For example, circuitry 1810 can include circuitry for comparing the analyses with a set of parameters for an expected medication event for the individual, such as time parameters, audio aspect parameters, or visual feature parameters.

FIG. 19 shows aspects of the system 200 illustrated in FIG. 2. FIG. 19 shows that, in some embodiments, the system 200 can include one or more of circuitry 1900, 1910, 1920. Circuitry 1900 includes circuitry for saving the determined compliance likelihood for the first medication event into a memory. For example, the saving the determined compliance likelihood for the first medication event can include saving into a RAM memory. For example, the saving the determined compliance likelihood for the first medication event can include saving into memory in a computer hard drive or removable memory device. Circuitry 1910 includes circuitry for saving the determined compliance likelihood for the first medication event into a health record for the individual. For example, the determined compliance likelihood can be saved into an existing health record for the individual, or saved into a newly generated health record for the individual. Circuitry 1920 includes circuitry for comparing the determined compliance likelihood for the first medication event to a compliance goal for the individual; and circuitry for indicating the comparison. For example, the comparison may communicate to a caregiver or the individual that there has been full compliance, or a lack of compliance.

FIG. 20 illustrates aspects of the system 200 shown in FIG. 2. FIG. 20 depicts that, in some embodiments, the system 200 can include one or more of circuitry 2000, 2010, 2020, 2030. Circuitry 2000 includes: circuitry for comparing the determined compliance likelihood for the first medication event to a determined compliance likelihood for a second medication event for the individual; circuitry for comparing the determined compliance likelihood for the first medication event and the determined compliance likelihood for the second medication event to a compliance goal for the individual; and circuitry for indicating the comparison. Circuitry 2010 includes: circuitry for receiving data. For example, the circuitry 2010 can be configured to receive data from a monitoring device (e.g. as 110 in FIG. 1). For example, the circuitry 2010 can be configured to receive data processed from a signal (e.g. as 115 in FIG. 1). Circuitry 2020 includes: circuitry for saving received data into a memory. For example, the circuitry 2020 can be configured to save data received from a monitoring device (e.g. as 110 in FIG. 1) into memory in a hard drive. For example, the circuitry 2020 can be configured to save data received from a monitoring device (e.g. as 110 in FIG. 1) into memory in a data storage device. Circuitry 2030 includes: circuitry for saving the analyses of the received data into a memory. For example, circuitry 2030 can include saving at least one of: the analysis of the received data for at least one attribute of an individual; the analysis of received data for at least one attribute relating to a medication during the first medication event; the analysis of the received data for at least one feature of visual information relating to the individual during the first medication event; the analysis of the received data for at least one feature of non-visual information relating to the individual during the first medication event; and the analysis of the received data for a time associated with the first medication event.

FIG. 21 shows aspects of the system 200 shown in FIG. 2. FIG. 21 illustrates that, in some embodiments, the system 200 can include one or more of circuitry 2100, 2110, 2120, 2130. Circuitry 2100 includes: circuitry for saving the analysis of the received data for an identifier of a first medication event for an individual into a memory. Circuitry 2110 includes: circuitry for saving the analysis of the received data for at least one attribute of an individual into a memory. Circuitry 2120 includes: circuitry for saving the analysis of the received data for at least one attribute relating to a medication during the first medication event into a memory. Circuitry 2130 includes: circuitry for saving the analysis of the received data for at least one feature of visual information relating to the individual during the first medication event into a memory.

FIG. 22 shows aspects of a system such as illustrated in FIG. 2. FIG. 22 depicts that, in some embodiments, the system 200 can include one or more of circuitry 2200, 2210, 2220. In some embodiments, FIG. 22 depicts that circuitry 2220 can include circuitry 2130. Circuitry 2200 includes: circuitry for saving the analysis of the received data for at least one feature of non-visual information relating to the individual during the first medication event into a memory. Circuitry 2210 includes: circuitry for saving the analysis of the received data for a time associated with the first medication event into a memory. Circuitry 2220 includes: circuitry for comparing the analyses with a set of standard analysis parameters for a standard medication event; circuitry for determining, based on the comparison, if the analyses are within the standard analysis parameters for the standard medication event; and circuitry for indicating the determination. In some embodiments, circuitry 2220 can include circuitry 2230. Circuitry 2230 includes: circuitry for saving the determination into a memory.

FIG. 23 shows aspects of the system as illustrated in FIG. 2. FIG. 23 depicts that, in some embodiments, the system 200 can include circuitry 2300, which can also include circuitry 2310. Although circuitry 210, 220, 230, 240 250, 260, 270 and 280 are not illustrated in FIG. 23 for clarity of presentation, they should be considered to be present in system 200. As shown in FIG. 23, circuitry 2300 includes: circuitry for analyzing received data for an identifier of a second medication event for the individual; circuitry for analyzing received data for the at least one attribute of the individual; circuitry for analyzing the received data for the at least one attribute relating to a medication during the second medication event; circuitry for analyzing the received data for at least one feature of visual information relating to the individual during the second medication event; circuitry for analyzing the received data for at least one feature of non-visual information relating to the individual during the second medication event; circuitry for analyzing the received data for a time associated with the second medication event; circuitry for determining the compliance likelihood for the second medication event based on the analyses of the received data; and circuitry for indicating the determined compliance likelihood for the second medication event. Circuitry 2310 includes: circuitry for comparing the determined compliance likelihood for the first medication event and the determined compliance likelihood for the second medication event; circuitry for determining a composite compliance likelihood for the first and second medication events; circuitry for saving the composite compliance likelihood into a memory; and circuitry for indicating the composite compliance likelihood.

FIG. 24 illustrates aspects of a computer system 120 including at least one main computing unit 125. Although a single main computing unit 125 is illustrated in FIG. 24, in some embodiments there may be a plurality of main computing units 125. A main computing unit 125 includes computer-readable storage medium including executable instructions for monitoring medication events relating to an individual 2400. The computer-readable storage medium including executable instructions for monitoring medication events relating to an individual 2400 includes instructions 2410, 2420, 2430, 2440, 2450, 2460, 2470 and 2480. Instructions 2410 include instructions for analyzing received data for an identifier of a first medication event for an individual. For example, the instruction can include instructions for analyzing received data for an identifier, such as a code identifier, of a first medication event for an individual. Instructions 2420 include instructions for analyzing the received data for at least one attribute of an individual. For example, instructions 2420 can include instructions for analyzing the received data for at least one visual feature of an individual, such as facial features. Instructions 2430 include instructions for analyzing the received data for at least one attribute relating to a medication during the first medication event. For example, instructions 2430 can include instructions for analyzing the received data for the color or shape of pills. For example, instructions 2430 can include instructions for analyzing the received data for the size and shape of an inhaler device. Instructions 2440 include instructions for analyzing the received data for at least one feature of visual information relating to the individual during the first medication event. For example, the instructions 2440 can include instructions for analyzing the received data for visual information relating to the individual placing medication in pill form into his or her mouth. Instructions 2450 include instructions for analyzing the received data for at least one feature of non-visual information relating to the individual during the first medication event. For example, the instructions 2450 can include instructions for analyzing the received data for audio information relating to the use of an inhaler by the individual. For example, the instructions 2450 can include instructions for analyzing the received data for audio information relating to the individual swallowing medication. Instructions 2460 include instructions for analyzing the received data for a time associated with the first medication event. For example, instructions 2460 can include instructions for analyzing the received data for a clock time associated with the first medication event. Instructions 2470 include instructions for determining a compliance likelihood for the first medication event based on the analyses of the received data. Instructions 2480 include instructions for indicating the determined compliance likelihood for the first medication event. For example, the instructions 2480 can include instructions to indicate the determined compliance likelihood for the first medication event on a display attached to the main computing unit 125. For example, the instructions 2480 can include instructions to indicate the determined compliance likelihood for the first medication event on a display attached to a secondary computing unit that are part of a system 120 (e.g. secondary computing units 130, 135 as illustrated in FIG. 1).

In some embodiments, the instructions 2410 for analyzing received data for an identifier of a first medication event for an individual can include instructions for analyzing received data encoded in a transmission originating from a cell phone. For example, an individual can send a transmission from a cell phone or smart phone to the system. In some embodiments, the instructions 2410 for analyzing received data for an identifier of a first medication event for an individual can include instructions for analyzing received data encoded in a transmission originating from a portable computing device. For example, an individual can send a transmission from a laptop, PDA, or tablet computing device to the system. In some embodiments, the instructions 2410 for analyzing received data for an identifier of a first medication event for an individual can include instructions for analyzing received data encoded in a transmission originating from a fixed position camera unit. For example, the medication event can occur in a location within range of a fixed position camera unit, which is configured to transmit data regarding the medication event to the system. In some embodiments, the instructions 2410 for analyzing received data for an identifier of a first medication event for an individual can include instructions for analyzing the received data for an identifier that includes a time value. For example, the instructions can include instructions for analyzing the received data for a clock time value. In some embodiments, the instructions 2410 for analyzing received data for an identifier of a first medication event for an individual can include instructions for analyzing received data for an identifier that includes a code. For example, an individual can enter a code into a keyboard attached to a monitoring device and the code may be transmitted to the system. For example, a code may be automatically generated by the system to identify a specific medication event. In some embodiments, the instructions 2410 for analyzing received data for an identifier of a first medication event for an individual can include instructions for analyzing the received data for an identifier that includes at least one visual information feature. For example, the instructions can include instructions for analyzing the received data for an identifier that includes visual information regarding the individual. For example, the instructions can include instructions for analyzing the received data for an identifier that includes visual information regarding the medication label. For example, the instructions can include instructions for analyzing the received data for an identifier that includes visual information regarding the individual as well as the medication label. In some embodiments, the instructions 2410 for analyzing received data for an identifier of a first medication event for an individual can include instructions for analyzing the received data for an identifier that includes at least one non-visual information feature. For example, the instructions can include instructions for analyzing the received data for an identifier that includes audio information, such as the sound of the individual swallowing or the sound of the individual using an inhaler. For example, the instructions can include instructions for analyzing the received data for an identifier that includes thermal information, such as skin temperature of the individual during the medication event. In some embodiments, the instructions 2410 for analyzing received data for an identifier of a first medication event for an individual can include instructions for analyzing the received data for a radio-frequency identification (RFID) code. For example, an individual or a caregiver can use a monitoring device to receive a RFID signal from the medication packaging, which can then be part of a data transmission from the monitoring device.

In some embodiments, instructions 2420 for analyzing the received data for at least one attribute of an individual can include: instructions for associating the identifier of the first medication event with an expected individual; instructions for retrieving one or more specific identifiers associated with the expected individual; instructions for analyzing the received data for the presence or absence of at least one of the one or more specific identifiers; and instructions for indicating the presence or absence of the expected individual based on the analysis. In some embodiments, instructions 2420 for analyzing the received data for at least one attribute of an individual can include: instructions for associating the identifier of the first medication event with an expected individual;

instructions for retrieving one or more attributes associated with the expected individual; instructions for comparing the retrieved one or more attributes associated with the expected individual with the received data; instructions for determining, based on the comparison, a confirmation likelihood for the expected individual; and instructions for indicating the determined confirmation likelihood for the expected individual. In some embodiments, instructions 2420 for analyzing the received data for at least one attribute of an individual can include: instructions for analyzing the received data for at least one attribute of the individual; instructions for comparing the at least one attribute of the individual with a set of attribute parameters for an expected individual; and instructions for determining, based on the comparison, an attribute score for the at least one attribute of the individual. For example, the instructions can include instructions for comparing at least one facial feature of the individual with a set of facial feature parameters for an expected individual, such as a percentage of the face included in the data, or eye color discernible from the data. The instructions can include instructions for presenting the attribute score in a visual format, such as a table, text, or a graph. The instructions can include instructions for saving the attribute score in a memory.

In some embodiments, instructions 2430 for analyzing the received data for at least one attribute relating to a medication during the first medication event can include instructions for analyzing received data for an attribute that includes at least one visual information feature. For example, the instructions can include instructions for analyzing received data for a visual feature of the medication, such as pill color, size, inhaler shape, medication label, or visual features of the medication packaging. In some embodiments, instructions 2430 for analyzing the received data for at least one attribute relating to a medication during the first medication event can include instructions for analyzing received data for an attribute that includes at least one non-visual information feature. For example, the instructions can include instructions for analyzing received data for an audio attribute of an inhaler, a thermal attribute of a syringe, or a micropower impulse radar (MIR) attribute of the medication. In some embodiments, instructions 2430 for analyzing the received data for at least one attribute relating to a medication during the first medication event can include instructions for analyzing received data for an attribute that includes a radio-frequency identification (RFID) code. For example, a monitoring device can receive RFID signals from the packaging of a medication and transmit those signals to the system for analysis.

In some embodiments, instructions 2430 for analyzing the received data for at least one attribute relating to a medication during the first medication event can include: instructions for analyzing the received data for at least one attribute of the medication; instructions for comparing the at least one attribute of the medication with a set of attribute parameters for an expected medication; and instructions for determining, based on the comparison, an attribute score for the at least one attribute of the medication. In some embodiments, instructions 2430 for analyzing the received data for at least one attribute relating to a medication during the first medication event can include: instructions for associating the identifier of the first medication event with an expected medication; instructions for retrieving one or more specific identifiers associated with the expected medication; instructions for analyzing the received data for the presence or absence of at least one of the one or more specific identifiers; and instructions for indicating the presence or absence of the expected medication based on the analysis. For example, instructions 2430 can include: instructions for associating the identifier of the first medication event with an expected medication, such as an expected medication for a specific individual at that distinct medication event; instructions for retrieving one or more specific identifiers associated with the expected medication, such as visual aspects of the medication packaging; instructions for analyzing the received data for the presence or absence of at least one of the one or more specific identifiers, such as the visual aspects of the medication packaging; and instructions for indicating the presence or absence of the expected medication based on the analysis. The indication can be carried out, for example, on a main computing unit (e.g. item 125 in FIG. 1), or a secondary computing unit (e.g. items 135, 140 in FIG. 1). Instructions for indicating the presence or absence of the expected medication based on the analysis can also be sent to a monitoring device (e.g. item 110 in FIG. 1), for the individual patient or a caregiver at the site of the medication event to obtain a medication confirmation during the medication event. In some embodiments, instructions 2430 for analyzing the received data for at least one attribute relating to a medication during the first medication event can include: instructions for associating the identifier of the first medication event with an expected medication; instructions for retrieving one or more attributes associated with the expected medication; instructions for comparing the retrieved one or more attributes associated with the expected medication with the received data; instructions for determining, based on the comparison, a confirmation likelihood for the expected medication; and instructions for indicating the determined confirmation likelihood for the expected medication.

In some embodiments, instructions 2440 for analyzing the received data for the at least one feature of visual information relating to the individual during the first medication event can include: instructions for identifying a visual information component of the received data; instructions for comparing the identified visual information component of the received data with at least one visual information parameter; and instructions for determining a likelihood of sufficiency for the visual information component of the received data based on the comparison. In some embodiments, instructions 2440 for analyzing the received data for the at least one feature of visual information relating to the individual during the first medication event can include: instructions for associating the identifier of the first medication event with a set of visual information parameters for a standard medication event; instructions for comparing the at least one feature of visual information relating to the individual during the first medication event with the set of visual information parameters for the standard medication event; instructions for determining, based on the comparison, a medication event compliance score for the first medication event; and instructions for indicating the determined medication event compliance score for the first medication event.

In some embodiments, instructions 2450 for analyzing the received data for the at least one feature of non-visual information relating to the individual during the first medication event can include: instructions for analyzing the received data for the at least one feature of non-visual information including near-infrared (IR) information. In some embodiments, instructions 2450 for analyzing the received data for the at least one feature of non-visual information relating to the individual during the first medication event can include: instructions for analyzing the received data for the at least one feature of non-visual information including auditory information. In some embodiments, instructions 2450 for analyzing the received data for the at least one feature of non-visual information relating to the individual during the first medication event can include: instructions for analyzing the received data for the at least one feature of non-visual information including thermal information. In some embodiments, instructions 2450 for analyzing the received data for the at least one feature of non-visual information relating to the individual during the first medication event can include: instructions for analyzing the received data for the at least one feature of non-visual information including kinetic information. In some embodiments, instructions 2450 for analyzing the received data for the at least one feature of non-visual information relating to the individual during the first medication event can include: instructions for analyzing the received data for the at least one feature of non-visual information including micropower impulse radar (MIR) information.

In some embodiments, instructions 2450 for analyzing the received data for the at least one feature of non-visual information relating to the individual during the first medication event can include: instructions for identifying a non-visual information component of the received data; instructions for comparing the identified non-visual information component of the received data with at least one non-visual information parameter; and instructions for determining a likelihood of sufficiency for the non-visual information component of the received data based on the comparison. In some embodiments, instructions 2450 for analyzing the received data for the at least one feature of non-visual information relating to the individual during the first medication event can include: instructions for associating the identifier of the first medication event with a set of non-visual information parameters for a standard medication event; instructions for comparing the at least one feature of non-visual information relating to the individual during the first medication event with the set of non-visual information parameters for the standard medication event; instructions for determining, based on the comparison, a medication event compliance score for the first medication event; and instructions for indicating the determined medication event compliance score for the first medication event.

In some embodiments, instructions 2460 for analyzing the received data for a time associated with the first medication event includes: instructions for identifying a time component in the received data; instructions for comparing the identified time component with at least one time parameter associated with an expected medication event for the individual; and instructions for determining, based on the comparisons, a time score for the first medication event based on the received data. In some embodiments, instructions 2460 for analyzing the received data for a time associated with the first medication event includes: instructions for identifying a time component in the received data; instructions for associating the identifier of a first medication event for an individual with an expected medication time for the individual; instructions for comparing the identified time component with the expected medication time; instructions for determining, based on the comparison, a medication event time compliance score for the first medication event; and instructions for indicating the determined medication event time compliance score for the first medication event.

In some embodiments, instructions 2470 for determining the compliance likelihood for the first medication event based on the analyses of the received data includes: instructions for comparing the analyses with a set of parameters for a standard medication event; and instructions for calculating, based on the comparison, a compliance likelihood for the first medication event. In some embodiments, instructions 2470 for determining the compliance likelihood for the first medication event based on the analyses of the received data includes: instructions for comparing the analyses with a set of parameters for an expected medication event for the individual; and instructions for calculating, based on the comparison, a compliance likelihood for the individual with the expected medication event.

As illustrated in FIG. 24, main computing unit 125 includes computer-readable storage medium including executable instructions for monitoring medication events relating to an individual 2400. The computer-readable storage medium including executable instructions for monitoring medication events relating to an individual 2400 includes instructions 2410, 2420, 22430, 2440, 2450, 2460 and 2470. In some embodiments, the computer-readable storage medium including executable instructions for monitoring medication events relating to an individual 2400 includes additional instructions. In some embodiments, the computer-readable storage medium including executable instructions for monitoring medication events relating to an individual 2400 includes instructions for saving the determined compliance likelihood for the first medication event into memory. For example, the instructions can include instructions for saving the determined compliance likelihood for the first medication event into computer memory, such as a hard drive in the main computing unit 125. In some embodiments, the computer-readable storage medium including executable instructions for monitoring medication events relating to an individual 2400 includes instructions for saving the determined compliance likelihood for the first medication event into a health record for the individual. For example, the instructions can include instructions for saving the determined compliance likelihood into a health record for the individual into computer memory, such as in the main computing unit 125. In some embodiments, the computer-readable storage medium including executable instructions for monitoring medication events relating to an individual 2400 includes instructions for comparing the determined compliance likelihood for the first medication event to a compliance goal for the individual; and instructions for indicating the comparison. For example, the instructions can include instructions for indicating the comparison on a display device attached to the main computing unit 125.

In some embodiments, the computer-readable storage medium including executable instructions for monitoring medication events relating to an individual 2400 includes instructions for instructions for comparing the determined compliance likelihood for the first medication event to a determined compliance likelihood for a second medication event for the individual; instructions for comparing the determined compliance likelihood for the first medication event and the determined compliance likelihood for the second medication event to a compliance goal for the individual; and instructions for indicating the comparison. For example, the instructions can include instructions for indicating the comparison on a display device attached to the main computing unit 125. In some embodiments, the computer-readable storage medium including executable instructions for monitoring medication events relating to an individual 2400 includes instructions for receiving data. For example, the instructions for receiving data can include instructions for receiving data from a monitoring device (e.g. item 110 in FIG. 1).

In some embodiments, the computer-readable storage medium including executable instructions for monitoring medication events relating to an individual 2400 includes instructions for saving received data into a memory. For example, the instructions for saving received data into a memory can include saving received data into computer memory, such as in the main computing unit 125. In some embodiments, the computer-readable storage medium including executable instructions for monitoring medication events relating to an individual 2400 includes instructions for saving the analyses of the received data into a memory. In some embodiments, the computer-readable storage medium including executable instructions for monitoring medication events relating to an individual 2400 includes instructions for saving the analysis of the received data for at least one attribute of an individual into a memory. In some embodiments, the computer-readable storage medium including executable instructions for monitoring medication events relating to an individual 2400 includes instructions for saving the analysis of the received data for at least one attribute relating to a medication during the first medication event into a memory. In some embodiments, the computer-readable storage medium including executable instructions for monitoring medication events relating to an individual 2400 includes instructions for saving the analysis of the received data for at least one feature of visual information relating to the individual during the first medication event into a memory. In some embodiments, the computer-readable storage medium including executable instructions for monitoring medication events relating to an individual 2400 includes instructions for saving the analysis of the received data for at least one feature of non-visual information relating to the individual during the first medication event into a memory. In some embodiments, the computer-readable storage medium including executable instructions for monitoring medication events relating to an individual 2400 includes instructions for saving the analysis of the received data for a time associated with the first medication event into a memory. For example, the instructions for saving one or more of the analyses into a memory can include saving into computer memory, such as in the main computing unit 125.

In some embodiments, the computer-readable storage medium including executable instructions for monitoring medication events relating to an individual 2400 includes instructions for comparing the analyses with a set of standard analysis parameters for a standard medication event; instructions for determining, based on the comparison, if the analyses are within the standard analysis parameters for the standard medication event; and instructions for indicating the determination. In some embodiments, the instructions for determining, based on the comparison, if the analyses are within the standard analysis parameters for the standard medication event includes instructions for saving the determination into a memory. For example, the instructions for saving the determination into a memory can include saving into computer memory, such as in the main computing unit 125. In some embodiments, the computer-readable storage medium including executable instructions for monitoring medication events relating to an individual 2400 includes instructions for analyzing the received data for an identifier of a second medication event for the individual; instructions for analyzing the received data for the at least one attribute of the individual; instructions for analyzing the received data for the at least one attribute relating to a medication during the second medication event; instructions for analyzing the received data for at least one feature of visual information relating to the individual during the second medication event; instructions for analyzing the received data for at least one feature of non-visual information relating to the individual during the second medication event; instructions for analyzing the received data for a time associated with the second medication event; instructions for determining a compliance likelihood for the second medication event based on the analyses of the received data; and instructions for indicating the determined compliance likelihood for the second medication event. In some embodiments, the computer-readable storage medium including executable instructions for monitoring medication events relating to an individual 2400 includes instructions for comparing the determined compliance likelihood for the first medication event and the determined compliance likelihood for the second medication event; instructions for determining a composite compliance likelihood for the first and second medication events; instructions for saving the composite compliance likelihood into a memory; and instructions for indicating the composite compliance likelihood.

FIG. 25 illustrates a flowchart of a method 2500 for monitoring medication events relating to an individual. These method steps can be carried out, for example, by a computer system (e.g. item 120 in FIG. 1). FIG. 25 shows that the method includes a series of steps, 2510, 2520, 2530, 2540, 2550, 2560, 2570, 2580. Method step 2510 includes analyzing received data for an identifier of a first medication event for an individual, the received data originating from at least one monitoring device (e.g. item 110 in FIG. 1). Method step 2520 includes analyzing the received data for at least one attribute of an individual. For example, analyzing the received data for at least one attribute of an individual can include analyzing the received data for a code associated with a particular individual. Method step 2530 includes analyzing the received data for at least one attribute relating to a medication during the first medication event. For example, the method can include analyzing the received data for at least one visual attribute relating to a medication during the first medication event, such as the color and design of the medication packaging. Method step 2540 includes analyzing the received data for at least one feature of visual information relating to the individual during the first medication event. For example, the method can include analyzing the received data for at least one feature of visual information relating to the individual that includes a visual feature, such as facial features of the individual. Method step 2550 includes analyzing the received data for at least one feature of non-visual information relating to the individual during the first medication event. For example, the method can include analyzing the received data for at least one feature of non-visual information relating to the individual that includes an audio feature, such as from a recording of the individual stating "I am taking my medication now." Method step 2560 includes analyzing the received data for a time associated with the first medication event. For example, the method can include analyzing the received data for a clock time associated with the first medication event, such as "between 2:00 PM and 2:30 PM." Method step 2570 includes determining a compliance likelihood for the first medication event based on the analyses of the received data. Method step 2580 includes indicating the determined compliance likelihood for the first medication event. For example, the determined compliance likelihood for the first medication event can be displayed on a monitor attached to the computer system (e.g. item 120 in FIG. 1). Other aspects of the method steps can be identified in the text and claims herein.

FIG. 26 illustrates a system 2600 for monitoring medication events. The system 2600 can, for example, be part of a computer system (see item 120 in FIG. 1). The system 2600 includes circuitry 2610, 2620, 2630, 2640, 2650, 2660, 2670, 2680, 2690, 2695. The circuitry is configured to carry out specific processes. Circuitry 2610 includes circuitry for accepting data regarding a medication event for an individual. Circuitry 2620 includes circuitry for extracting, from the accepted data regarding the medication event for the individual, one or more identifiers of the medication. Circuitry 2630 includes circuitry for comparing the one or more identifiers of the medication with a set of standard medication identifier parameters. Circuitry 2640 includes circuitry for extracting, from the accepted data regarding the medication event for the individual, one or more visual features of the medication event. Circuitry 2650 includes circuitry for comparing the one or more visual features of the medication event with a set of medication event parameters. Circuitry 2660 includes circuitry for extracting, from the accepted data regarding the medication event for the individual, one or more non-visual features of the medication event. Circuitry 2670 includes circuitry for comparing the one or more non-visual features of the medication event with the set of medication event parameters. Circuitry 2680 includes circuitry for extracting, from the accepted data regarding the medication event for the individual, a time associated with the medication event. Circuitry 2690 includes circuitry for comparing the time associated with the medication event with an expected medication event time for the individual. Circuitry 2695 includes circuitry for saving the comparisons into a memory. For example, the circuitry 2695 can include circuitry for saving the comparisons into a computer system memory, (such as part of item 120 in FIG. 1).

FIG. 27 illustrates aspects of the system 2600 for monitoring medication events shown in FIG. 26. FIG. 27 depicts that, in some embodiments, circuitry 2610 for accepting data regarding a medication event for an individual can include one or more of circuitry 2700, 2710, 2720, 2730 and 2740. Circuitry 2610 for accepting data regarding a medication event for an individual can include circuitry 2700 for accepting data originating from a cell phone. For example, a cell phone including a camera and microphone can be used as a monitoring device in a medication event (see, e.g. item 110 in FIG. 1). Circuitry 2610 for accepting data regarding a medication event for an individual can include circuitry 2710 for accepting data originating from a portable computing device. For example, a portable computing device, such as a laptop, PDA or tablet, including a camera and microphone can be used as a monitoring device in a medication event (see, e.g. item 110 in FIG. 1). Circuitry 2610 for accepting data regarding a medication event for an individual can include circuitry 2720 for accepting data originating from a fixed position camera unit. For example, a fixed position camera unit, such as a camera unit configured to be affixed to a wall, and including a microphone, can be used as a monitoring device in a medication event (see, e.g. item 110 in FIG. 1). Circuitry 2610 for accepting data regarding a medication event for an individual can include circuitry 2730 for accepting data originating from a plurality of devices. For example, a plurality of devices, such as more than one fixed position camera unit, such as a camera unit configured to be affixed to a wall, and each including microphones, can be used as a plurality of monitoring devices for a medication event (see, e.g. item 110 in FIG. 1). Circuitry 2610 for accepting data regarding a medication event for an individual can include circuitry 2740 for accepting data originating from a micropower impulse radar (MIR) device. For example, a micropower impulse radar (MIR) device, can be used with a camera as monitoring devices for a medication event (see, e.g. item 110 in FIG. 1).

FIG. 28 shows aspects of the system 2600 for monitoring medication events shown in FIG. 26. FIG. 28 illustrates that, in some embodiments, circuitry 2620 for extracting, from the accepted data regarding the medication event for the individual, one or more identifiers of the medication, includes one or more of circuitry 2800, 2810. Circuitry 2620 for extracting, from the accepted data regarding the medication event for the individual, one or more visual features of the medication can include circuitry 2800 for extracting visual data. For example, circuitry 2800 for extracting visual data can include extracting data originating from a camera device. Circuitry 2620 for extracting, from the accepted data regarding the medication event for the individual, one or more visual features of the medication can include circuitry 2810 for extracting radio frequency identification (RFID) information. For example, circuitry 2810 for extracting radio frequency identification (RFID) information can include extracting data originating from a reflected RFID signal, such as a RFID signal reflected from the medication label.

FIG. 28 depicts aspects of the system 2600 for monitoring medication events shown in FIG. 26. FIG. 28 shows that, in some embodiments, circuitry 2630 for comparing the one or more identifiers of the medication with a set of standard medication identifier parameters, includes circuitry 2820. Circuitry 2630 for comparing the one or more identifiers of the medication with a set of standard medication identifier parameters can include circuitry 2820 for comparing visual features. For example, circuitry 2820 for comparing visual features of the medication, such as size, shape and color of pills. For example, circuitry 2820 for comparing visual features of the medication, such as size, shape and color of a medication dispenser (e.g. a syringe unit or an inhaler unit).

FIG. 28 shows aspects of the system 2600 for monitoring medication events shown in FIG. 26. FIG. 28 illustrates that, in some embodiments, circuitry 2640 for extracting, from the accepted data regarding the medication event for the individual, one or more visual features of the medication event, includes circuitry 2830 for extracting one or more visual features over time. For example, circuitry 2830 for extracting one or more visual features over time can include extracting one or more visual features over time from a series of camera images taken by the same camera device during the medication event. For example, circuitry 2830 for extracting one or more visual features over time can include extracting one or more visual features over time from a video taken by a single camera device during the medication event. For example, circuitry 2830 for extracting one or more visual features over time can include extracting one or more visual features over time from a series of camera images taken by multiple camera units over time during the medication event.

FIG. 29 shows aspects of the system 2600 for monitoring medication events shown in FIG. 26. FIG. 29 illustrates that, in some embodiments, circuitry 2650 for comparing the one or more visual features of the medication event with a set of medication event parameters includes circuitry 2900. Circuitry 2900 includes circuitry for determining, from a set of standard medication event visual features, at least one expected visual feature; and circuitry for comparing the accepted data regarding the medication event for the individual with the determined at least one expected visual feature. For example, the system can utilize a look-up table to obtain a set of standard medication event visual features. The system can then determine, from the set, which of the standard medication event visual features are relevant to a particular medication. A system can determine, for example, that the position of an inhaler relative to the individual's mouth during use is a standard medication event visual features for a particular medication that is administered with an inhaler device. The system can then comparing the accepted data regarding the medication event for the individual with the determined at least one expected visual feature, such as the position of the specific inhaler device relative to the individual's mouth.

FIG. 29 illustrates aspects of the system 2600 for monitoring medication events shown in FIG. 26. FIG. 29 illustrates that, in some embodiments, circuitry 2660 for extracting, from the accepted data regarding the medication event for the individual, one or more non-visual features of the medication event, includes circuitry 2910. Circuitry 2910 includes circuitry for extracting the one or more non-visual features over time. For example, the system can utilize a look-up table to obtain a set of standard medication event visual features. The system can then determine, from the set, which of the standard medication event non-visual features are relevant to a particular medication. A system can determine, for example, that the sound of an inhaler during use is a standard medication event visual features for a particular medication that is administered with an inhaler device. The system can then comparing the accepted data regarding the medication event for the individual with the determined at least one expected non-visual feature, such as the sound generated by a specific inhaler device during use.

FIG. 30 shows aspects of the system 2600 for monitoring medication events shown in FIG. 26. FIG. 30 depicts that, in some embodiments, circuitry 2660 for extracting, from the accepted data regarding the medication event for the individual, one or more non-visual features of the medication event, includes one or more of circuitry 3000, 3010, 3020, 3030. In some embodiments, circuitry 2660 for extracting, from the accepted data regarding the medication event for the individual, one or more non-visual features of the medication event, includes circuitry 3000 for extracting one or more audio features. For example, circuitry 3000 for extracting one or more audio features can include extracting one or more audio features from the use of a medication, such as an inhaler device, during the medication event. For example, circuitry 3000 for extracting one or more audio features can include extracting one or more audio features from the opening of a medication package, such as a particular sound of a package being broken open, during the medication event. For example, circuitry 3000 for extracting one or more audio features can include extracting one or more audio features generated by the individual or a caregiver, such as the individual saying "I am taking my medication now." In some embodiments, circuitry 2660 for extracting, from the accepted data regarding the medication event for the individual, one or more non-visual features of the medication event, includes circuitry 3010 for extracting one or more near-infrared (IR) features. For example, circuitry 3010 for extracting one or more near-infrared (IR) features can include extracting one or more near-IR features from the data obtained during the medication event, such as the near-IR conditions of a medication device. For example, circuitry 3010 for extracting one or more near-infrared (IR) features can include extracting one or more near-IR features from the data obtained during the medication event, such as the near-IR conditions of an individual's throat while drinking during a medication event. For example, circuitry 3010 for extracting one or more near-infrared (IR) features can include extracting one or more near-IR features from the data obtained during the medication event, such as the near-IR conditions of an individual's skin adjacent to an injection site during a medication event. In some embodiments, circuitry 2660 for extracting, from the accepted data regarding the medication event for the individual, one or more non-visual features of the medication event, includes circuitry 3020 for extracting one or more thermal features. For example, circuitry 3020 for extracting one or more thermal features can include extracting one or more thermal features of a medication administration device during the medication event. A change in thermal features can indicate that a medication administration device, such as an inhaler, has been utilized correctly during the medication event. For example, circuitry 3020 for extracting one or more thermal features can include extracting one or more thermal features of an individual's skin during the medication event. A change in thermal features of an individual's skin during the medication event can indicate, for example, that a medication injected via syringe has been properly administered. In some embodiments, circuitry 2660 for extracting, from the accepted data regarding the medication event for the individual, one or more non-visual features of the medication event, includes circuitry 3030 for extracting one or more features detectable by micropower impulse radar (MIR). For example, circuitry 3030 for extracting one or more features detectable by micropower impulse radar (MIR) can include extracting one or more features of an individual's physiology, such as respiration rate or heart rate. See: "Micropower Impulse Radar," Azevedo and McEwan, Science and Technology Review, January/February 1996, pages 17-29; and US Patent Application Publications No. 2004/0249257 and 2004/0249258 to Tupin et al., each titled "Article of Manufacture for Extracting Physiological Data Using Ultra-Wideband Radar and Improved Signal Processing Techniques," which are all incorporated by reference herein. See also: US Patent Application Publication No. 2009/0227882 to Foo, titled "Ultra Wideband Monitoring Systems and Antennas," which is incorporated by reference herein.

Figure 31:
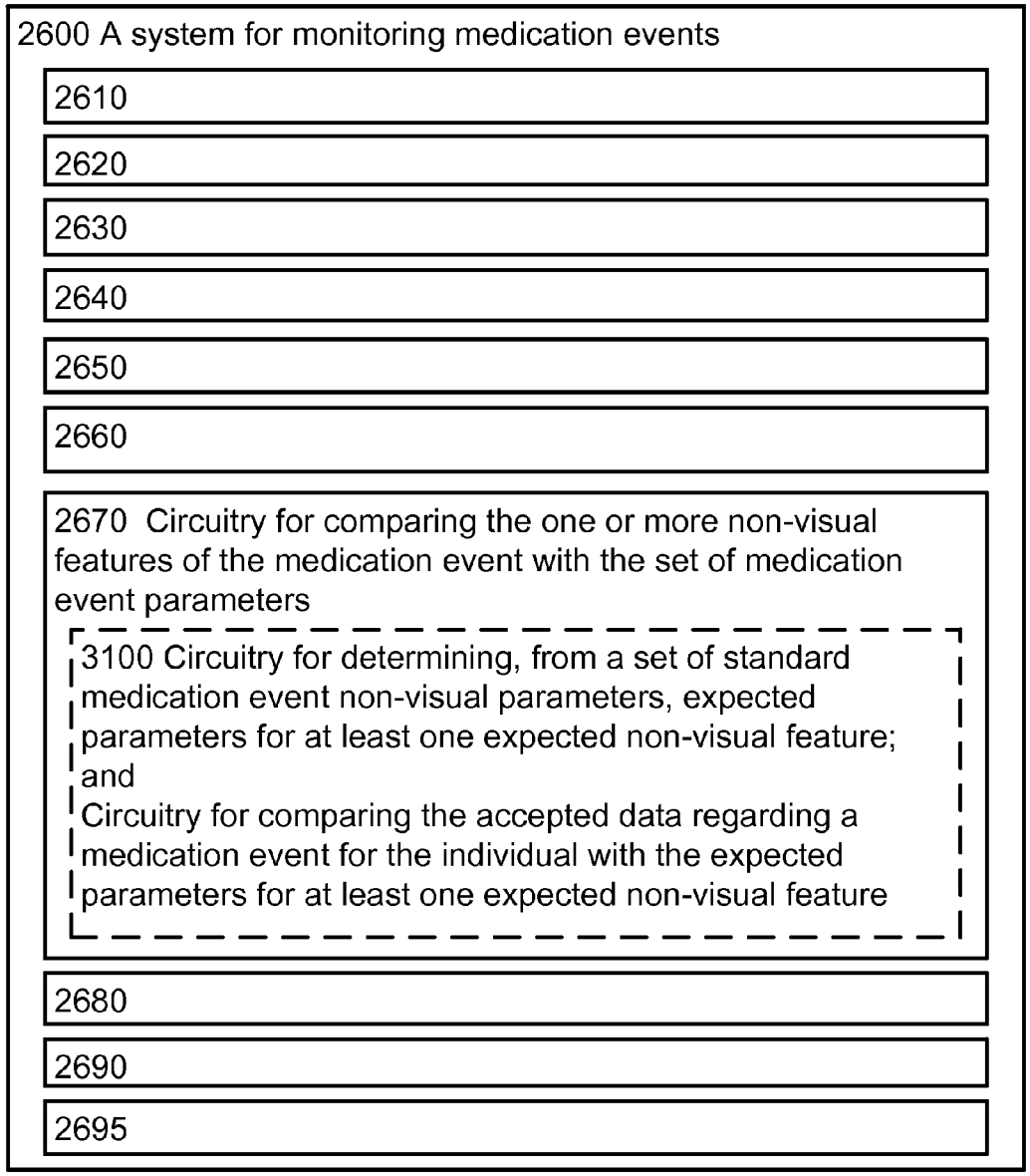
FIG. 31 shows aspects of the system of FIG. 26.

FIG. 31 illustrates aspects of the system 2600 for monitoring medication events shown in FIG. 26. FIG. 31 shows that, in some embodiments, circuitry 2670 for comparing the one or more non-visual features of the medication event with the set of medication event parameters includes circuitry 3100. In some embodiments, circuitry 2670 includes circuitry 3100 for determining, from the set of standard medication event non-visual parameters, expected parameters for at least one expected non-visual feature; and circuitry for comparing the accepted data regarding the medication event for the individual with the expected parameters for at least one expected non-visual feature. For example, circuitry 3100 can include determining, from the set of standard medication event audio parameters, expected parameters for at least one expected audio feature, such as the sound of an inhaler device administering a medication to an individual; and circuitry for comparing the accepted data regarding the medication event for the individual with the expected parameters for at least one expected audio feature. For example, circuitry 3100 can include determining, from the set of standard medication event audio parameters, expected parameters for at least one expected thermal feature, such as the skin temperature of an individual at a site adjacent to an injection during the injection; and circuitry for comparing the accepted data regarding the medication event for the individual with the expected parameters for at least one expected thermal feature.

Figure 32:
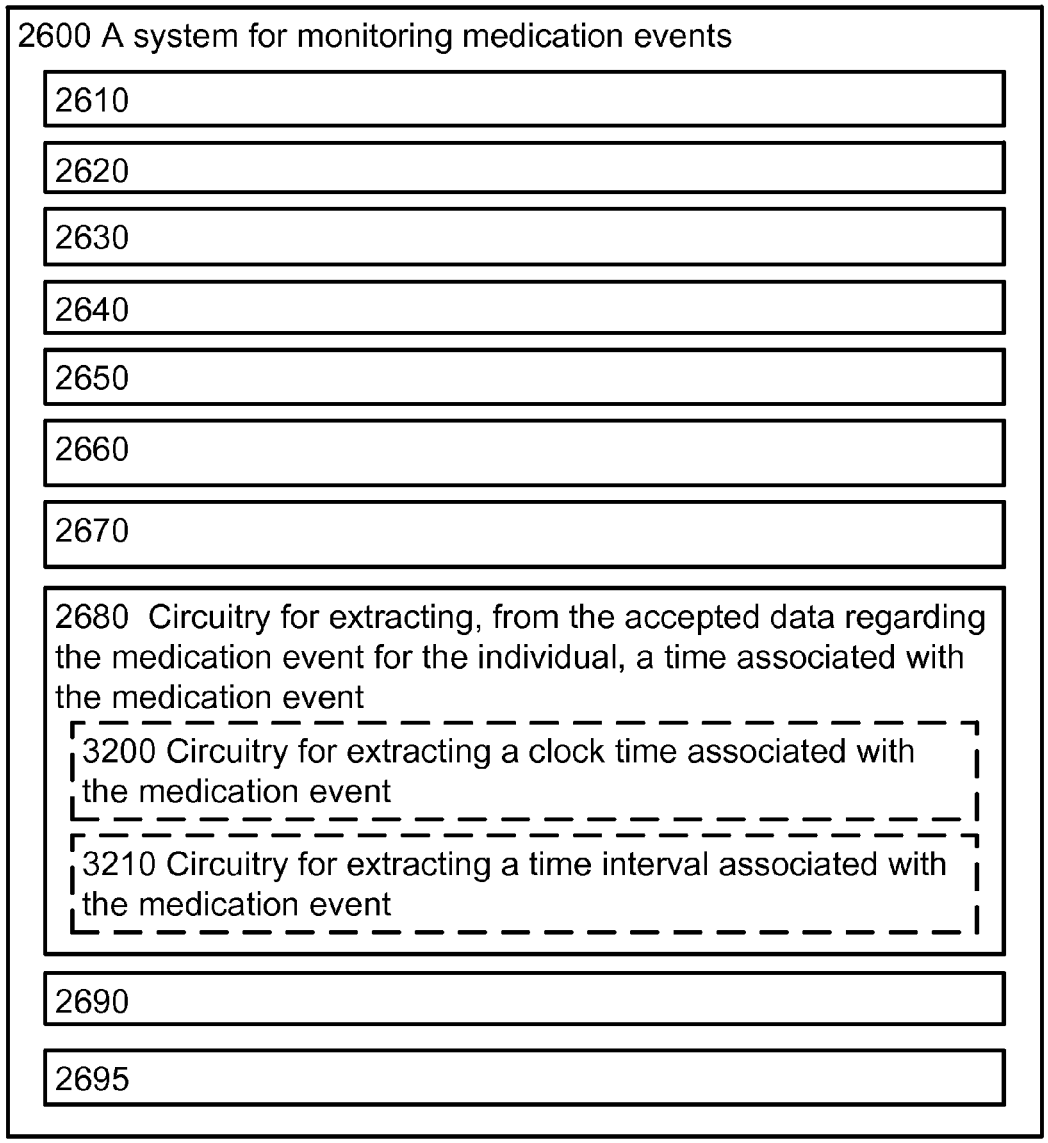
FIG. 32 depicts aspects of the system of FIG. 26.

FIG. 32 shows aspects of the system 2600 for monitoring medication events shown in FIG. 26. FIG. 32 illustrates that, in some embodiments, circuitry 2680 for extracting, from the accepted data regarding the medication event for the individual, a time associated with the medication event includes one or more of circuitry 3200, 3210. Circuitry 3200 includes circuitry for extracting a clock time associated with the medication event. For example, circuitry 3200 can include extracting a clock time associated with the medication event, such as "the next medication event is scheduled for 1:00 PM." Circuitry 3210 includes circuitry for extracting a time interval associated with the medication event. For example, circuitry 3210 can include extracting a time interval associated with the medication event that is a range, such as "the next medication event is scheduled for between 8:30 AM and 9:00 AM." For example, circuitry 3210 can include extracting a time interval associated with the medication event that is an interval from another event, such as a prior medication event for a meal. For example, circuitry 3210 can include extracting a time interval associated with the medication event such as "the next medication event is due no more than 1 hour after the completion of the individual's breakfast."

FIG. 33 depicts aspects of the system 2600 for monitoring medication events shown in FIG. 26. FIG. 33 shows that, in some embodiments, circuitry 2690 for comparing the time associated with the medication event with the expected medication event time for the individual includes circuitry 3300. Circuitry 3300 includes: circuitry for determining, from a set of standard medication event times, at least one expected medication event time; and circuitry for comparing the extracted time associated with the medication event with the determined at least one expected medication event time.

FIG. 33 shows aspects of the system 2600 for monitoring medication events shown in FIG. 26. FIG. 33 illustrates that, in some embodiments, the system includes circuitry 3310. Circuitry 3310 includes circuitry for determining, from the comparison of the one or more identifiers of the medication with the set of standard medication identifier parameters, if the one or more identifiers of the medication are within the set of standard medication identifier parameters. For example, a set of standard medication identifier parameters can include a number of pills, and the system can compare the number of pills detected in the received data with the extected number to determine if the correct number of pills were detected. For example, a set of standard medication identifier parameters can include the color and shape of the medication packaging, and the system can compare and determine if the standard packaging was detected. In some embodiments, the determination if the one or more identifiers of the medication are within the set of standard medication identifier parameters can be indicated to a caregiver, such as through a display device attached to the computer system (e.g. item 120 in FIG. 1). In some embodiments, the determination if the one or more identifiers of the medication are within the set of standard medication identifier parameters can be indicated to the individual, such as through a display device attached to the monitoring device (e.g. item 110 in FIG. 1).

FIG. 34 depicts aspects of the system 2600 for monitoring medication events shown in FIG. 26. FIG. 34 shows that, in some embodiments, the system includes one or more of circuitry 3400, 3410. Circuitry 3400 includes circuitry for determining, from the comparison of the one or more non-visual features of the medication event with the set of medication event parameters, if the one or more non-visual features of the medication event are within the set of medication event parameters. Circuitry 3410 includes circuitry for determining, from the comparison of the time associated with the medication event with the expected medication event time for the individual, if the time associated with the medication event is within the expected medication event time for the individual.

FIG. 35 illustrates aspects of the system 2600 for monitoring medication events shown in FIG. 26. FIG. 35 depicts that, in some embodiments, the system includes one or more of circuitry 3500, 3510, 3520, 3530. Circuitry 3500 includes circuitry for saving one or more of the comparisons into a medical record for the individual. For example, a medical record can be saved into computer memory in the computer system (e.g. item 120 in FIG. 1). Circuitry 3510 includes circuitry for determining, from the comparisons, a medication compliance score for the medication event. In some embodiments, the a medication compliance score for the medication event can be saved into computer memory. In some embodiments, the a medication compliance score for the medication event can be indicated to a caregiver or the individual, such as through a display device attached to the computer system (e.g. item 120 in FIG. 1) or integrated in a monitoring device (e.g. item 110 in FIG. 1). Circuitry 3520 includes circuitry for indicating one or more of the comparisons. For example, the comparisons can be indicated to a caregiver or the individual, such as through a display device attached to the computer system (e.g. item 120 in FIG. 1) or integrated in a monitoring device (e.g. item 110 in FIG. 1). Circuitry 3530 includes circuitry for activating, depending on one or more of the comparisons, an alert indicator. For example, an alert indicator within the computer system (e.g. item 120 in FIG. 1) can be activated to notify caregivers to review the medication event.

FIG. 36 shows aspects of the system 2600 for monitoring medication events shown in FIG. 26. FIG. 36 illustrates that, in some embodiments, the system includes circuitry 3600, which can include circuitry 3610. Circuitry 3600 includes: circuitry for accepting data regarding a second medication event for the individual; circuitry for extracting, from the accepted data regarding the second medication event for the individual, one or more identifiers of the medication; circuitry for comparing the one or more identifiers of the medication with a set of standard medication identifier parameters; circuitry for extracting, from the accepted data regarding the second medication event for the individual, one or more visual features of the medication event; circuitry for comparing the one or more visual features of the second medication event with a set of medication event parameters; circuitry for extracting, from the accepted data regarding the second medication event for the individual, one or more non-visual features of the second medication event; circuitry for comparing the one or more non-visual features of the second medication event with the set of medication event parameters; circuitry for extracting, from the accepted data regarding the second medication event for the individual, a time associated with the second medication event; circuitry for comparing the time associated with the second medication event with an expected second medication event time for the individual; and circuitry for saving the comparisons associated with the second medication event into a memory. Circuitry 3600 can include circuitry 3610, which includes: circuitry for determining, from the saved comparisons associated with the medication event and the comparisons associated with the second medication event, if the medication events meet at least one standard; and circuitry for activating an indicator in response to the determination.

FIG. 37 shows aspects of a computer system 120 including at least one main computing unit 125. Although a single main computing unit 125 is illustrated in FIG. 37, in some embodiments there may be a plurality of main computing units 125. A main computing unit 125 includes computer-readable storage medium including executable instructions for monitoring medication events relating to an individual 3700. The computer-readable storage medium including executable instructions for monitoring medication events relating to an individual 3700 includes instructions 3710, 3720, 3730, 3740, 3750, 3760, 3770, 3780, 3790 and 3795. Instructions 3710 include instructions for accepting data regarding a medication event for an individual. For example, the instructions 3710 can include instructions for accepting data regarding a medication event for an individual from a monitoring device (e.g. item 110 in FIG. 1). Instructions 3720 include instructions for extracting, from the accepted data regarding the medication event for the individual, one or more identifiers of the medication. For example, the instructions 3720 can include instructions for extracting, from the accepted data regarding the medication event for the individual, one or more identifiers of the medication such as color, shape and size of pills for a medication in pill form. For example, the instructions 3720 can include instructions for extracting, from the accepted data regarding the medication event for the individual, one or more identifiers of the medication such as visual aspects of a medication device, such as an inhaler or a syringe. For example, the instructions 3720 can include instructions for extracting, from the accepted data regarding the medication event for the individual, one or more identifiers of the medication such as non-visual identifiers such as a RFID code extracted from a reflection from a RFID tag on the medication or medication packaging. Instructions 3730 include instructions for comparing the one or more identifiers of the medication with a set of standard medication identifier parameters. For example, a RFID code extracted from a reflection from a RFID tag on the medication or medication packaging can be compared to a set of standard RFID codes from medications or medication packaging. Instructions 3740 include instructions for extracting, from the accepted data regarding the medication event for the individual, one or more visual features of the medication event. For example, instructions 3740 can include instructions for extracting, from the accepted data regarding the medication event for the individual, one or more visual features of the medication event from data obtained by a camera unit integrated within a monitoring device (e.g. item 110 in FIG. 1). Instructions 3750 include instructions for comparing the one or more visual features of the medication event with a set of medication event parameters. For example, facial image data from the individual can be compared with a set of visible medication event parameters. Instructions 3760 include instructions for extracting, from the accepted data regarding the medication event for the individual, one or more non-visual features of the medication event. For example, instructions 3760 can include instructions for extracting, from the accepted data regarding the medication event for the individual, one or more audio features of the medication event from data obtained by a microphone integrated within a monitoring device (e.g. item 110 in FIG. 1). Instructions 3770 include instructions for comparing the one or more non-visual features of the medication event with the set of medication event parameters. For example, instructions 3770 can include instructions for comparing the audio features of the medication event with the set of medication event parameters, such as the audio parameters for an inhaler device in use. Instructions 3780 include instructions for extracting, from the accepted data regarding the medication event for the individual, a time associated with the medication event. For example, instructions 3780 can include extracting a clock time. Instructions 3790 include instructions for comparing the time associated with the medication event with an expected medication event time for the individual. For example, instructions 3790 can include instructions for comparing the time associated with the medication event taken from a clock integrated with the monitoring device with an expected medication event time for the individual, such as retrieved from the individual's medication regimen. Instructions 3795 include instructions for saving the comparisons into a memory. For example, instructions 3795 for saving the comparisons into a memory can include saving the comparisons into a computer memory within the computer system 120.

As shown in FIG. 37, instructions 3710 include instructions for accepting data regarding a medication event for an individual. In some embodiments, instructions 3710 include instructions for accepting data originating from a cell phone. For example, the instructions 3710 can include instructions for accepting data regarding a medication event for an individual from a monitoring device (e.g. item 110 in FIG. 1) that is a cell phone. In some embodiments, instructions 3710 include instructions for accepting data originating from a portable computing device. For example, the instructions 3710 can include instructions for accepting data regarding a medication event for an individual from a monitoring device (e.g. item 110 in FIG. 1) that is a portable computing device. In some embodiments, instructions 3710 include instructions for accepting data originating from a fixed position camera unit. For example, the instructions 3710 can include instructions for accepting data regarding a medication event for an individual from a monitoring device (e.g. item 110 in FIG. 1) that is a fixed position camera unit. In some embodiments, instructions 3710 include instructions for accepting data originating from a plurality of devices. For example, the instructions 3710 can include instructions for accepting data regarding a medication event for an individual from a plurality of monitoring devices (e.g. item 110 in FIG. 1) that can include cell phones, portable computing devices (e.g. laptops, table computing devices and PDAs), fixed position camera units, or a combination thereof. In some embodiments, instructions 3710 include instructions for accepting data originating from a micropower impulse radar (MIR) device.

Instructions 3720, as shown in FIG. 37, include instructions for extracting, from the accepted data regarding the medication event for the individual, one or more identifiers of the medication. In some embodiments, instructions 3720 include instructions for extracting visual data. For example, instructions 3720 can include instructions for extracting visual data such as visual aspects of the medication (e.g. pill size, color and shape), visual aspects of the medication administration devices (e.g. syringe or inhaler) or visual aspects of the medication packaging (e.g. box color, logo, bar code or Q code). In some embodiments, instructions 3720 include instructions for extracting radio frequency identification (RFID) information. For example, a monitoring device (e.g. item 110 in FIG. 1) can receive RFID signals originating from or reflected from a medication or medication packaging, and process this information to be transmitted to the computer system 120. The instructions 3720 can include instructions for extracting the radio frequency identification (RFID) information obtained from or reflected from a medication or medication packaging.

Instructions 3730, as shown in FIG. 37, include instructions for comparing the one or more identifiers of the medication with a set of standard medication identifier parameters. In some embodiments, instructions 3730 can include instructions for comparing visual features. For example, instructions 3730 can include instructions for comparing visual features such as visual features of the medication itself (e.g. pill size, color and shape), of its administration devices (e.g. syringe or inhaler) or its packaging (e.g. box color, logo, bar code or Q code).

Instructions 3740, as shown in FIG. 37, include instructions for extracting, from the accepted data regarding the medication event for the individual, the one or more visual features of the medication event. In some embodiments, instructions 3740 include instructions for extracting one or more visual features over time. For example, the instructions for extracting one or more visual features over time can include instructions for extracting one or more visual features from a series of images taken by a camera over time. For example, the instructions for extracting one or more visual features over time can include instructions for extracting one or more visual features from a series of images taken by multiple cameras over time. For example, the instructions for extracting one or more visual features over time can include instructions for extracting one or more visual features from a video.

Instructions 3750, as shown in FIG. 37, include instructions for comparing the one or more visual features of the medication event with the set of medication event parameters. In some embodiments, instructions 3750 include: instructions for determining, from a set of standard medication event visual features, at least one expected visual feature; and instructions for comparing the accepted data regarding a medication event for the individual with the determined at least one expected visual feature. For example, an expected visual feature can include the placement of an inhaler adjacent to an individual's mouth. For example, an expected visual feature can include placement of pills in the individual's mouth. For example, an expected visual feature can include placement of a syringe adjacent to the individual's skin.

Instructions 3760, as shown in FIG. 37, include instructions for extracting, from the accepted data regarding the medication event for the individual, the one or more non-visual features of the medication event. For example, the instructions 3760 can include instructions for extracting one or more non-visual features over time. For example, one or more features can be extracted from a video (e.g. as a sound over time). For example, the instructions 3760 can include instructions for extracting one or more audio features. For example, one or more features can be extracted from data obtained from a microphone. For example, the instructions 3760 can include instructions for extracting one or more thermal features. For example, instructions for extracting one or more thermal features can include thermal features of the individual (e.g. skin temperature) or thermal features of a medication administration device (e.g. an inhaler may change temperature during use). For example, the instructions 3760 can include instructions for extracting one or more features detectable by micropower impulse radar (MIR). See: "Micropower Impulse Radar," Azevedo and McEwan, Science and Technology Review, January/February 1996, pages 17-29; and US Patent Application Publications No. 2004/0249257 and 2004/0249258 to Tupin et al., each titled "Article of Manufacture for Extracting Physiological Data Using Ultra-Wideband Radar and Improved Signal Processing Techniques," which are all incorporated by reference herein. See also: US Patent Application Publication No. 2009/0227882 to Foo, titled "Ultra Wideband Monitoring Systems and Antennas," which is incorporated by reference herein.

Instructions 3770, as shown in FIG. 37, include instructions for comparing the one or more non-visual features of the medication event with the set of medication event parameters. In some embodiments, instructions 3770 include: instructions for determining, from a set of standard medication event non-visual parameters, expected parameters for at least one expected non-visual feature; and instructions for comparing the accepted data regarding a medication event for the individual with the expected parameters for at least one expected non-visual feature. For example, instructions 3770 can include: instructions for determining, from a set of standard medication event audio parameters, expected audio parameters for at least one expected audio feature, such as tone or pitch; and instructions for comparing the accepted data regarding a medication event for the individual with the expected parameters for at least one expected audio feature. For example, instructions 3770 can include: instructions for determining, from a set of standard medication event thermal parameters, expected parameters for at least one expected thermal feature, such as thermal parameters for an individual's skin temperature in a region adjacent to an injection; and instructions for comparing the accepted data regarding a medication event for the individual with the expected thermal parameters for at least one expected thermal feature.

Instructions 3780, as shown in FIG. 37, include instructions for extracting, from the accepted data regarding the medication event for the individual, the time associated with the medication event. In some embodiments, instructions 3780 include instructions for extracting a time interval associated with the medication event. For example, a time interval can include a clock time interval (e.g. between 2:00 and 2:15 PM). For example, a time interval can include an elapsed time interval (e.g. 3 hours since the last medication event). For example, a time interval can include a time interval relative to another event (e.g. between 1 hour and 2 hours after a meal).

Instructions 3790, as shown in FIG. 37, include instructions for comparing the time associated with the medication event with the expected medication event time for the individual. In some embodiments, instructions 3790 include: instructions for determining, from a set of standard medication event times, at least one expected medication event time; and instructions for comparing the extracted time associated with the medication event with the determined at least one expected medication event time.

Instructions 3795, as shown in FIG. 37, include instructions for saving the comparisons into a memory. For example, the instructions can be saved into a computer memory within the computer system 120.

In some embodiments, the flowchart illustrated in FIG. 37 includes additional set of instructions. In some embodiments, the computer-readable storage medium including executable instructions for monitoring medication events relating to an individual includes: instructions for determining, from the comparison of the one or more identifiers of the medication with the set of standard medication identifier parameters, if the one or more identifiers of the medication are within the set of standard medication identifier parameters. In some embodiments, the computer-readable storage medium including executable instructions for monitoring medication events relating to an individual includes: instructions for determining, from the comparison of the one or more visual features of the medication event with a set of medication event parameters, if the one or more visual features of the medication event are within the set of medication event parameters. In some embodiments, the computer-readable storage medium including executable instructions for monitoring medication events relating to an individual includes: instructions for determining, from the comparison of the one or more non-visual features of the medication event with the set of medication event parameters, if the one or more non-visual features of the medication event are within the set of medication event parameters. In some embodiments, the computer-readable storage medium including executable instructions for monitoring medication events relating to an individual includes: instructions for determining, from the comparison of the time associated with the medication event with the expected medication event time for the individual, if the time associated with the medication event is within the expected medication event time for the individual. In some embodiments, the computer-readable storage medium including executable instructions for monitoring medication events relating to an individual includes: instructions for saving one or more of the comparisons into a medical record for the individual. For example, a medical record can be stored in computer memory on the computer system (e.g. 120 of FIG. 1). In some embodiments, the computer-readable storage medium including executable instructions for monitoring medication events relating to an individual includes: instructions for determining, from the comparisons, a medication compliance score for the medication event. In some embodiments, the computer-readable storage medium including executable instructions for monitoring medication events relating to an individual includes: instructions for indicating one or more of the comparisons. For example, instructions for indicating one or more of the comparisons can include indicating on a display device attached to the computer system (e.g. 120 of FIG. 1). In some embodiments, the computer-readable storage medium including executable instructions for monitoring medication events relating to an individual includes: instructions for activating, depending on one or more of the comparisons, an alert indicator. For example, instructions for instructions for activating, depending on one or more of the comparisons, an alert indicator can include an alert indicator (such as a light or a sound emitter device) attached to the computer system (e.g. 120 of FIG. 1).

In some embodiments, the computer-readable storage medium including executable instructions for monitoring medication events relating to an individual includes: instructions for accepting data regarding a second medication event for the individual; instructions for extracting, from the accepted data regarding the second medication event for the individual, one or more identifiers of the medication; instructions for comparing the one or more identifiers of the medication with the set of standard medication identifier parameters; instructions for extracting, from the accepted data regarding the second medication event for the individual, one or more visual features of the medication event; instructions for comparing the one or more visual features of the second medication event with the set of medication event parameters; instructions for extracting, from the accepted data regarding the second medication event for the individual, one or more non-visual features of the second medication event; instructions for comparing the one or more non-visual features of the second medication event with the set of medication event parameters; instructions for extracting, from the accepted data regarding the second medication event for the individual, a time associated with the second medication event; instructions for comparing the time associated with the second medication event with an expected second medication event time for the individual; and instructions for saving the comparisons associated with the second medication event into a memory. In some embodiments, the instructions include: instructions for determining, from the saved comparisons associated with the medication event and the comparisons associated with the second medication event, if the medication events meet at least one standard; and instructions for activating an indicator in response to the determination.

FIG. 38 illustrates a flowchart of a method 3800 for monitoring medication events. These method steps can be carried out, for example, by a computer system (e.g. item 120 in FIG. 1). FIG. 38 shows that the method includes a series of steps, 3810, 3820, 3830, 3840, 3850, 3860, 3870, 3880, 3890, 3895. Method step 3810 includes accepting data regarding a medication event for an individual. For example, a computer system (e.g. item 120 in FIG. 1) can accept data transmitted from a monitoring device (e.g. item 110 in FIG. 1). Method step 3820 includes extracting, from the accepted data regarding the medication event for the individual, one or more identifiers of the medication. Method step 3830 includes comparing the one or more identifiers of the medication with a set of standard medication identifier parameters. Method step 3840 includes extracting, from the accepted data regarding the medication event for the individual, one or more visual features of the medication event. Method step 3850 includes comparing the one or more visual features of the medication event with a set of medication event parameters. Method step 3860 includes extracting, from the accepted data regarding the medication event for the individual, one or more non-visual features of the medication event. Method step 3870 includes comparing the one or more non-visual features of the medication event with the set of medication event parameters. Method step 3880 includes extracting, from the accepted data regarding the medication event for the individual, a time associated with the medication event. Method step 3890 includes comparing the time associated with the medication event with an expected medication event time for the individual. Method step 3895 includes saving the comparisons into a memory.

As shown in FIG. 38, method step 3810 includes accepting data regarding a medication event for an individual. In some embodiments, method step 3810 can include accepting data originating from a cell phone. In some embodiments, method step 3810 can include accepting data originating from a portable computing device. In some embodiments, method step 3810 can include accepting data originating from a fixed position camera unit. In some embodiments, method step 3810 can include accepting data originating from a plurality of devices. For example, a computer system (e.g. 120 in FIG. 1) can accept data regarding a medication event for an individual from a monitoring device (e.g. 110 in FIG. 1). The monitoring device can include one or more of a cell phone, a portable computing device (e.g. a laptop, tablet computer, or PDA). In some embodiments, method step 3810 can include accepting data originating from a micropower impulse radar (MIR) device. See: "Micropower Impulse Radar," Azevedo and McEwan, Science and Technology Review, January/February 1996, pages 17-29; and US Patent Application Publications No. 2004/0249257 and 2004/0249258 to Tupin et al., each titled "Article of Manufacture for Extracting Physiological Data Using Ultra-Wideband Radar and Improved Signal Processing Techniques," which are all incorporated by reference herein. See also: US Patent Application Publication No. 2009/0227882 to Foo, titled "Ultra Wideband Monitoring Systems and Antennas," which is incorporated by reference herein.

FIG. 38 illustrates that method step 3820 includes extracting, from the accepted data regarding the medication event for the individual, one or more identifiers of the medication. In some embodiments, method step 3820 includes extracting visual data. For example, method step 3820 can include extracting visual data from data generated by a camera integrated into a computing device (e.g. a laptop, smartphone, PDA or tablet computer). In some embodiments, method step 3820 includes extracting radio frequency identification (RFID) information. For example, the accepted data regarding the medication event for the individual can include data obtained from a RFID signal originating from or reflected by a RFID tag included with a medication or medication packaging.

FIG. 38 shows that method step 3830 includes comparing the one or more identifiers of the medication with a set of standard medication identifier parameters. In some embodiments, method step 3830 includes comparing visual features. For example, the method can include comparing visual features such as visual features of the medication (e.g. pill color, size and shape) or visual features of the medication administration devices (e.g. syringe or inhaler) or visual features of the medication packaging (e.g. color, logo, or shape).

FIG. 38 shows that method step 3840 includes extracting, from the accepted data regarding a medication event for the individual, one or more visual features of the medication event. In some embodiments, method step 3840 includes extracting one or more visual features over time. For example, method step 3840 can include extracting one or more visual features over time, such as from a series of images or a video recorded by a camera unit.

FIG. 38 depicts that method step 3850 includes comparing the one or more visual features of the medication event with a set of medication event parameters. In some embodiments, method step 3850 includes: determining, from a set of standard medication event visual features, at least one expected visual feature; and comparing the accepted data regarding a medication event for the individual with the determined at least one expected visual feature.

FIG. 38 illustrates that method step 3860 includes extracting, from the accepted data regarding a medication event for the individual, one or more non-visual features of the medication event. In some embodiments, method step 3860 includes extracting one or more non-visual features over time. For example, method step 3860 can include extracting audio features from an audio recording over time. In some embodiments, method step 3860 includes extracting one or more audio features. For example, method step 3860 can include extracting audio features recorded by a microphone device integrated in the monitoring device (e.g. item 110 in FIG. 1). For example, method step 3860 can include extracting one or more near-infrared (IR) features. For example, method step 3860 can include extracting one or more thermal features. For example, method step 3860 can include extracting one or more features detectable by micropower impulse radar (MIR).

FIG. 38 shows that method step 3870 includes comparing the one or more non-visual features of the medication event with a set of medication event parameters. In some embodiments, method step 3870 includes: determining, from a set of standard medication event non-visual parameters, expected parameters for at least one expected non-visual feature; and comparing the accepted data regarding a medication event for the individual with the expected parameters for at least one expected non-visual feature.

FIG. 38 shows that method step 3880 includes extracting, from the accepted data regarding a medication event for the individual, a time associated with the medication event. In some embodiments, method step 3880 includes extracting a clock time associated with the medication event. For example, method step 3880 can extract a clock time such as "3:45 PM." In some embodiments, method step 3880 includes extracting a time interval associated with the medication event. For example, method step 3880 can extract a clock time interval, such as "between 10:00 AM and 10:10 AM." For example, method step 3880 can extract an elapsed time interval, such as "the audio recording of the inhaler sound lasted 30 seconds." For example, method step 3880 can extract an elapsed time interval, such as "there was 5 minutes between the injection of medication A and the swallowing of medication B."

FIG. 38 shows that method step 3890 includes comparing the time associated with the medication event with an expected medication event time for the individual. In some embodiments, method step 3890 includes: determining, from a set of standard medication event times, at least one expected medication event time; and comparing the extracted time associated with the medication event with the determined at least one expected medication event time.

FIG. 38 shows that method step 3895 includes saving the comparisons into a memory. For example, method step 3895 can include saving the comparisons into a memory in a computer system (e.g. item 120 in FIG. 1).

In some embodiments, there are one or more additional steps to the method illustrated in FIG. 38. For example, the method for monitoring medication events can include determining, from the comparison of the one or more identifiers of the medication with the set of standard medication identifier parameters, if the one or more identifiers of the medication are within the set of standard medication identifier parameters. For example, the method for monitoring medication events can include determining, from the comparison of the one or more visual features of the medication event with a set of medication event parameters, if the one or more visual features of the medication event are within the set of medication event parameters. For example, the method for monitoring medication events can include determining, from the comparison of the one or more non-visual features of the medication event with the set of medication event parameters, if the one or more non-visual features of the medication event are within the set of medication event parameters. For example, the method for monitoring medication events can include determining, from the comparison of the time associated with the medication event with the expected medication event time for the individual, if the time associated with the medication event is within the expected medication event time for the individual. For example, the method for monitoring medication events can include saving one or more of the comparisons into a medical record for the individual. For example, method for monitoring medication events can include saving the comparisons into medical record for the individual in a memory in a computer system (e.g. item 120 in FIG. 1). For example, the method for monitoring medication events can include determining, from the comparisons, a medication compliance score for the medication event. A medication compliance score can be saved in memory, such as into a memory in a computer system (e.g. item 120 in FIG. 1). A medication compliance score can be displayed, such as with a display device attached to the computer system (e.g. item 120 in FIG. 1). For example, the method for monitoring medication events can include indicating one or more of the comparisons. One or more of the comparisons can be indicated on a device attached to the computer system (e.g. item 120 in FIG. 1), or on a monitoring device (e.g. item 110 in FIG. 1). For example, the method for monitoring medication events can include activating, depending on one or more of the comparisons, an alert indicator. An alert indicator, for example, can be attached to the computer system (e.g. item 120 in FIG. 1).

For example, the method for monitoring medication events can include: accepting data regarding a second medication event for the individual; extracting, from the accepted data regarding the second medication event for the individual, one or more identifiers of the medication; comparing the one or more identifiers of the medication with a set of standard medication identifier parameters; extracting, from the accepted data regarding the second medication event for the individual, one or more visual features of the medication event; comparing the one or more visual features of the second medication event with a set of medication event parameters; extracting, from the accepted data regarding the second medication event for the individual, one or more non-visual features of the second medication event; comparing the one or more non-visual features of the second medication event with the set of medication event parameters; extracting, from the accepted data regarding the second medication event for the individual, a time associated with the second medication event; comparing the time associated with the second medication event with an expected second medication event time for the individual; and saving the comparisons associated with the second medication event into a memory. The method can also include: determining, from the saved comparisons associated with the medication event and the comparisons associated with the second medication event, if the medication events meet at least one standard; and activating an indicator in response to the determination.

FIG. 39 illustrates diagram of aspects of a system for monitoring medication events. The system can be a computer system such as depicted in FIG. 1 and described herein. The system 3900 depicted in FIG. 39 includes electrical circuitry. The circuitry of the system 3900 is configured to carry out a series of logical processes. As illustrated in FIG. 39, a system 3900 for monitoring medication events relating to an individual includes one or more circuitry components 3910, 3920, 3930, 3940, 3950, 3960, 3970. The circuitry is configured to carry out specific processes.

The system 3900 includes circuitry 3910 for associating a time interval with a first medication event for an individual. The system 3900 includes circuitry 3920 for identifying a start of the time interval associated with the first medication event. The system 3900 includes circuitry 3930 for activating an indicator in response to the identification of the start of the time interval associated with the first medication event. The system 3900 includes circuitry 3940 for activating at least one camera unit associated with the individual, the activating in response to the identification of the start of the time interval associated with the first medication event. The system 3900 includes circuitry 3950 for identifying an end of the time interval associated with the first medication event. The system 3900 includes circuitry 3960 for accepting data relating to the time interval associated with the first medication event from the at least one camera unit. The system 3900 includes circuitry 3970 for deactivating the at least one camera unit in response to the identification of the end of the time interval associated with the first medication event.

FIG. 40 illustrates aspects of the system 3900 shown in FIG. 39. FIG. 40 shows that, in some embodiments, circuitry 3910 for associating the time interval with the first medication event for the individual includes one or more of circuitry 4000, 4010. In some embodiments, circuitry 3910 includes circuitry 4000 for associating a clock time interval with the first medication event. For example, circuitry for associating a clock time interval with the first medication event can include associating that the medication event lasted from a clock time to another clock time, such as from 9:45 to 10:00 AM. In some embodiments, circuitry 3910 includes circuitry 4010 for associating an elapsed time interval with the first medication event. For example, circuitry 4010 can associate an elapsed time interval from a prior event with the first medication event, such as the elapsed time interval from an individual's prior meal.

FIG. 40 also illustrates that, in some embodiments, circuitry 3920 for identifying a start of the time interval associated with the first medication event includes one or more of circuitry 4020, 4030. Circuitry 4020 includes circuitry for identifying the start of a clock time interval associated with the first medication event. For example, circuitry 4020 can identify that the first medication event started at 10:00 AM and had a duration of 5 minutes. Circuitry 4030 includes circuitry for identifying the start of an elapsed time interval associated with the first medication event. For example, circuitry 4020 can identify that the first medication event started 2 hours after another event, such as 2 hours since the individual drank a glass of water.

FIG. 40 also illustrates that, in some embodiments, circuitry 3930 for activating the indicator in response to the identification of the start of the time interval associated with the first medication event includes circuitry 4040, 4050, 4060. Circuitry 4040 includes circuitry for activating a visual indicator. For example, a system 3900 can include circuitry 4040 for activating a visual indicator attached to a computer system (e.g. item 120 in FIG. 1) or a visual indicator integrated into a monitoring device (e.g. item 110 in FIG. 1) in response to the identification of the start of the time interval associated with the first medication event. Circuitry 4050 includes circuitry for activating an auditory indicator. For example, a system 3900 can include circuitry 4040 for activating an auditory indicator attached to a computer system (e.g. item 120 in FIG. 1) or an auditory indicator integrated into a monitoring device (e.g. item 110 in FIG. 1) in response to the identification of the start of the time interval associated with the first medication event. Circuitry 4060 includes circuitry for activating a vibratory indicator. For example, a system 3900 can include circuitry 4060 for activating a vibratory indicator attached to a computer system (e.g. item 120 in FIG. 1) or a vibratory indicator integrated into a monitoring device (e.g. item 110 in FIG. 1) in response to the identification of the start of the time interval associated with the first medication event.

FIG. 41 depicts aspects of the system 3900 illustrated in FIG. 39. FIG. 41 shows that, in some embodiments, circuitry 3940 for activating the at least one camera unit associated with the individual, the activating in response to the identification of the start of the time interval associated with the first medication event includes one or more of circuitry 4100, 4110, 4120, 4130, 4140. Circuitry 4100 includes circuitry for activating at least one camera unit within a mobile phone. For example, circuitry 4100 can include circuitry for activating at least one camera unit within a mobile phone integrated into a monitoring device (e.g. item 110 in FIG. 1). Circuitry 4110 includes circuitry for activating at least one camera unit within a portable computing device. For example, circuitry 4110 can include circuitry for activating at least one camera unit within a portable computing device used as a monitoring device (e.g. item 110 in FIG. 1). Circuitry 4120 includes circuitry for activating at least one camera unit within a fixed position camera unit. For example, circuitry 4120 can include circuitry for activating a fixed position camera unit integrated into a monitoring device (e.g. item 110 in FIG. 1). Circuitry 4130 includes circuitry for activating a plurality of camera units. For example, circuitry 4130 can include circuitry for activating at least two of: camera unit within a cell phone, a camera unit within a portable computing device, or a fixed position camera unit. Circuitry 4140 includes circuitry for activating the at least one camera unit including activating non-visual components of the at least one camera unit. For example, circuitry 4140 can include activating a MIR integrated into a laptop computer.

FIG. 42 shows aspects of the system 3900 illustrated in FIG. 39. FIG. 4s shows that, in some embodiments, circuitry 3940 for activating the at least one camera unit associated with the individual, the activating in response to the identification of the start of the time interval associated with the first medication event includes one or more of circuitry 4200, 4210, 4220, 4230, 4240. Circuitry 4200 includes circuitry for activating at least one camera unit including a microphone. For example, circuitry 4200 can include circuitry for activating at least one camera unit including a microphone integrated into a portable computing device. Circuitry 4210 includes circuitry for activating at least one camera unit including a RFID detector. For example, circuitry 4210 can include circuitry for activating at least one camera unit including a RFID detector integrated into a monitoring device (e.g. item 110 in FIG. 1). Circuitry 4220 includes circuitry for activating the at least one camera unit for video data acquisition. Circuitry 4230 includes circuitry for activating the at least one camera unit for a series of data acquisition events. For example, a camera unit can be activated to obtain images every 5 seconds for a period of time corresponding to the expected time of the medication event. Circuitry 4240 includes circuitry for activating the at least one camera unit for data acquisition including near-infrared (IR) data.

FIG. 43 illustrates aspects of the system 3900 illustrated in FIG. 39. FIG. 43 shows that, in some embodiments, circuitry 3940 for activating the at least one camera unit associated with the individual, the activating in response to the identification of the start of the time interval associated with the first medication event includes one or more of circuitry 4300, 4310. Circuitry 4300 includes circuitry for activating the at least one camera unit for data acquisition including thermal data. Circuitry 4310 includes circuitry for activating at least one micropower impulse radar (MIR) device.

FIG. 43 also depicts that, in some embodiments, circuitry 3950 for identifying the end of the time interval associated with the first medication event includes one or more of circuitry 4320, 4330. Circuitry 4320 includes circuitry for associating a clock time interval with the end of the time interval associated with the first medication event. For example, circuitry 4320 can include circuitry for associating a clock time of 10:15 to 10:20 AM with the end of the time interval associated with the first medication event. Circuitry 4330 includes circuitry for associating an elapsed time interval with the end of the time interval associated with the first medication event. For example, circuitry 4330 can include circuitry for associating the end of a 20 minute interval with the end of the time interval associated with the first medication event.

FIG. 44 depicts aspects of the system 3900 illustrated in FIG. 39. FIG. 44 illustrates that, in some embodiments, circuitry 3960 for accepting data relating to the time interval associated with the first medication event from the at least one camera unit includes one or more of circuitry 4400, 4410. Circuitry 4400 includes circuitry for accepting data generated by the at least one camera unit during the time interval associated with the first medication event. Circuitry 4410 includes circuitry for accepting data relating to the time interval associated with the first medication event from each of a plurality of camera units.

FIG. 44 also shows that, in some embodiments, circuitry 3970 for deactivating the at least one camera unit in response to the identification of the end of the time interval associated with the first medication event includes one or more of circuitry 4420, 4430. Circuitry 4420 includes circuitry for deactivating at least one camera unit within a mobile phone. Circuitry 4430 includes circuitry for deactivating at least one camera unit within a portable computing device.

FIG. 45 illustrates aspects of the system 3900 shown in FIG. 39. FIG. 45 depicts that, in some embodiments, circuitry 3970 for deactivating the at least one camera unit in response to the identification of the end of the time interval associated with the first medication event includes one or more of circuitry 4500, 4510. Circuitry 4500 includes circuitry for deactivating at least one camera unit within a fixed position camera unit. Circuitry 4510 includes circuitry for deactivating a plurality of camera units.

FIG. 45 also illustrates that, in some embodiments, the system depicted in FIG. 39 includes one or more of circuitry 4520, 4530. Circuitry 4520 includes circuitry for activating an indicator in response to the circuitry for accepting data relating to the time interval associated with the first medication event from the at least one camera unit. For example, circuitry 4520 can include circuitry for activating an indicator attached to the computer system (e.g. item 120 in FIG. 1) in response to the circuitry for accepting data relating to the time interval associated with the first medication event from the at least one camera unit. Circuitry 4530 includes circuitry for saving the accepted data relating to the time interval associated with the first medication event from the at least one camera unit into a memory. For example, circuitry 4520 can include circuitry for saving the accepted data relating to the time interval associated with the first medication event from the at least one camera unit into a memory attached to the computer system (e.g. item 120 in FIG. 1).

FIG. 46 depicts that, in some embodiments, the system shown in FIG. 39 includes one or more of circuitry 4600, 4610, 4620. Circuitry 4600 includes: circuitry for processing the accepted data relating to the time interval associated with the first medication event from the at least one camera unit into a transmission; and circuitry for transmitting the processed data. For example, the computer system (e.g. item 120 in FIG. 1) can transmit the processed data to another computing device. Circuitry 4610 includes circuitry for activating an indicator in response to the identification of the end of the time interval associated with the first medication event. For example, a computer system (e.g. item 120 in FIG. 1) can include an attached indicator device. Circuitry 4620 includes: circuitry for retrieving at least one attribute of the individual from memory; circuitry for examining the accepted data for the at least one attribute of the individual; circuitry for forming an identification result for the individual from the examination; and circuitry for transmitting the identification result for the individual.

FIG. 47 illustrates that, in some embodiments, the system shown in FIG. 39 includes one or more of circuitry 4700, 4710. Circuitry 4700 includes: circuitry for retrieving at least one attribute of the medication from memory; circuitry for examining the accepted data for the at least one attribute of the medication; circuitry for forming an identification result for the medication from the examination; and circuitry for transmitting the identification result for the medication. Circuitry 4710 includes circuitry for initiating a transmission in response to the identification of the start of the time interval associated with the first medication event.

FIG. 48 shows that, in some embodiments, the system depicted in FIG. 39 includes circuitry 4800. Circuitry 4800 includes: circuitry for associating a second time interval with a second medication event for the individual; circuitry for identifying a start of the second time interval associated with the second medication event; circuitry for activating an indicator in response to the identification of the start of the second time interval associated with the second medication event; circuitry for activating at least one camera unit associated with the individual, the activating in response to the identification of the start of the second time interval associated with the second medication event; circuitry for identifying an end of the second time interval associated with the second medication event; circuitry for accepting data relating to the second time interval associated with the second medication event from the at least one camera unit; and circuitry for deactivating the at least one camera unit in response to the identification of the end of the second time interval associated with the second medication event.

FIG. 49 shows that, in some embodiments, the system illustrated in FIG. 39 includes circuitry 4900, 4910. Circuitry 4900 includes: circuitry for comparing the time interval associated with the first medication event and the second time interval associated with the second medication event with a standard time interval; and circuitry for activating an indicator if either the time interval associated with the first medication event or the second time interval associated with the second medication event are distinct from the standard time interval. In some embodiments, circuitry 4900 is included within circuitry 4800, described above. Circuitry 4910 includes: circuitry for comparing the accepted data relating to the time interval associated with the first medication event with the set of standard medication event parameters; circuitry for comparing the accepted data relating to the second time interval associated with the second medication event with a set of standard medication event parameters; and circuitry for activating an indicator if either the accepted data relating to the time interval associated with the first medication event or the accepted data relating to the second time interval associated with the second medication event are distinct from the set of standard medication event parameters.

FIG. 50 shows aspects of a computer system 120 including at least one main computing unit 125. Although a single main computing unit 125 is illustrated in FIG. 50, in some embodiments there may be a plurality of main computing units 125. A main computing unit 125 includes computer-readable storage medium including executable instructions for monitoring medication events 5000. The computer-readable storage medium including executable instructions for monitoring medication events 5000 includes instructions 5010, 5020, 5030, 5040, 5050, 5060, 5070. Instructions 5010 include instructions for associating a time interval with a first medication event for an individual. Instructions 5020 include instructions for identifying a start of the time interval associated with the first medication event. Instructions 5030 include instructions for activating an indicator in response to the identification of the start of the time interval associated with the first medication event. Instructions 5040 include instructions for activating at least one camera unit associated with the individual, the activating in response to the identification of the start of the time interval associated with the first medication event. Instructions 5050 include instructions for identifying an end of the time interval associated with the first medication event. Instructions 5060 include instructions for accepting data relating to the time interval associated with the first medication event from the at least one camera unit. Instructions 5070 include instructions for deactivating the at least one camera unit in response to the identification of the end of the time interval associated with the first medication event.

Instructions 5010 include instructions for associating a time interval with a first medication event for an individual. In some embodiments, instructions 5010 include additional instructions. For example, in some embodiments, instructions 5010 include instructions for associating a clock time interval with the first medication event. For example, in some embodiments, instructions 5010 include instructions for associating an elapsed time interval with the first medication event.

Instructions 5020 include the instructions for identifying the start of the time interval associated with the first medication event. In some embodiments, instructions 5020 include additional instructions. For example, in some embodiments, instructions 5020 include instructions for identifying the start of a clock time interval associated with the first medication event. For example, in some embodiments, instructions 5020 include instructions for identifying the start of an elapsed time interval associated with the first medication event.

Instructions 5030 include the instructions for activating the indicator in response to the identification of the start of the time interval associated with the first medication event. In some embodiments, instructions 5030 include additional instructions. For example, in some embodiments, instructions 5030 include instructions for activating a visual indicator. For example, the instructions 5030 can lead to the activation of a visible indicator, such as a light, attached to the computer system (e.g. item 120 in FIG. 1). In some embodiments, instructions 5030 include instructions for activating an auditory indicator. For example, the instructions 5030 can lead to the activation of an auditory indicator, such as a buzzer, attached to the computer system (e.g. item 120 in FIG. 1). In some embodiments, instructions 5030 include instructions for activating an vibratory indicator. For example, the instructions 5030 can lead to the activation of an vibratory indicator, such as to result in the vibration of a component attached to the computer system (e.g. item 120 in FIG. 1).

Instructions 5040 include the instructions for activating the at least one camera unit associated with the individual, the activating in response to the identification of the start of the time interval associated with the first medication event. In some embodiments, instructions 5040 include additional instructions. For example, in some embodiments, instructions 5040 include instructions for activating at least one camera unit within a mobile phone. For example, the instructions 5040 can be processed into a transmission to a mobile phone that is a monitoring device (e.g. as item 110 in FIG. 1). In some embodiments, instructions 5040 can include instructions for activating at least one camera unit within a portable computing device. For example, the instructions 5040 can be processed into a transmission to a portable computing device (e.g. a laptop, a tablet computer, or a PDA) that is a monitoring device (e.g. as item 110 in FIG. 1). In some embodiments, instructions 5040 can include instructions for activating at least one camera unit within a fixed position camera unit. For example, the instructions 5040 can be processed into a transmission to a fixed position camera unit, such as a camera unit that is affixed to a wall at a location, that is a monitoring device (e.g. as item 110 in FIG. 1). In some embodiments, instructions 5040 can include instructions for activating plurality of camera units. For example, the instructions 5040 can be processed into a transmission to a plurality of monitoring devices (e.g. as item 110 in FIG. 1) including camera units. In some embodiments, instructions 5040 can include instructions activating the at least one camera unit including activating non-visual components of the at least one camera unit. For example, the instructions 5040 can be processed into a transmission to a portable computing device (e.g. a laptop, a tablet computer, or a PDA) that is a monitoring device (e.g. as item 110 in FIG. 1) and which includes non-visual components, such as a microphone, a RFID transceiver, or a micropoer impulse radar (MIR) device. In some embodiments, instructions 5040 can include instructions for activating at least one camera unit including a microphone. For example, the instructions 5040 can be processed into a transmission to a cell phone (e.g. a laptop, a tablet computer, or a PDA) that is a monitoring device (e.g. as item 110 in FIG. 1) leading to the activation of a microphone in the cell phone. In some embodiments, instructions 5040 can include instructions for activating at least one camera unit including a RFID detector. For example, the instructions 5040 can be processed into a transmission to a portable computing device (e.g. a laptop, a tablet computer, or a PDA) that is a monitoring device (e.g. as item 110 in FIG. 1) and that includes an RFID detector, resulting in the activation of the RFID detector. In some embodiments, instructions 5040 can include instructions for activating the at least one camera unit for video data acquisition. For example, the instructions 5040 can be processed into a transmission to a cell phone that is a monitoring device (e.g. as item 110 in FIG. 1) and resulting in the activation of video data acquisition by the cell phone. In some embodiments, instructions 5040 can include instructions activating the at least one camera unit for a series of data acquisition events. For example, the instructions 5040 can be processed into a transmission to a cell phone that is a monitoring device (e.g. as item 110 in FIG. 1) resulting in the activation of a camera in the cell phone for a series of short video recordings (e.g. a series of 100 events, each of 2 second duration) being taken by the cell phone camera. In some embodiments, instructions 5040 can include instructions for activating the at least one camera unit for data acquisition including near-infrared (IR) data. For example, the instructions 5040 can be processed into a transmission to a portable computing device (e.g. a laptop, a tablet computer, or a PDA) that is a monitoring device (e.g. as item 110 in FIG. 1) which results in the activation of a near-IR reader in the portable computing device. In some embodiments, instructions 5040 can include instructions for activating the at least one camera unit for data acquisition including thermal data. For example, the instructions 5040 can be processed into a transmission to a portable computing device (e.g. a laptop, a tablet computer, or a PDA) that is a monitoring device (e.g. as item 110 in FIG. 1) which results in the activation of a thermal reader in the portable computing device In some embodiments, instructions 5040 can include instructions for activating at least one micropower impulse radar (MIR) device. For example, the instructions 5040 can be processed into a transmission to a portable computing device (e.g. a laptop, a tablet computer, or a PDA) that is a monitoring device (e.g. as item 110 in FIG. 1) and that includes a MIR device, resulting in the activation of the MIR device.

Instructions 5050 include the instructions for identifying the end of the time interval associated with the first medication event. In some embodiments, instructions 5050 include additional instructions. For example, in some embodiments, instructions 5050 include instructions for associating a clock time interval with the end of the time interval associated with the first medication event. For example, in some embodiments instructions 5050 include instructions for associating an elapsed time interval with the end of the time interval associated with the first medication event.

Instructions 5060 include the instructions for accepting data relating to the time interval associated with the first medication event from the at least one camera unit. In some embodiments, instructions 5060 include additional instructions. For example, in some embodiments, instructions 5060 include instructions for accepting data generated by the at least one camera unit during the time interval associated with the first medication event. For example, in some embodiments, instructions 5060 include instructions for accepting data relating to the time interval associated with the first medication event from each of a plurality of camera units.

Instructions 5070 include the instructions for deactivating the at least one camera unit in response to the identification of the end of the time interval associated with the first medication event. In some embodiments, instructions 5070 include additional instructions. For example, in some embodiments, instructions 5070 include instructions for deactivating at least one camera unit within a mobile phone. For example, in some embodiments, instructions 5070 include instructions for deactivating at least one camera unit within a portable computing device. For example, in some embodiments, instructions 5070 include instructions for deactivating at least one camera unit within a fixed position camera unit. For example, in some embodiments, instructions 5070 include instructions for deactivating a plurality of camera units.

In some embodiments, the computer-readable storage medium 5000 including executable instructions for monitoring medication events includes instructions in addition to instructions 5010, 5020, 5030, 5040, 5050, 5060, 5070. In some embodiments, the computer-readable storage medium 5000 including executable instructions for monitoring medication events includes instructions for activating an indicator in response to the instructions for accepting data relating to the time interval associated with the first medication event from the at least one camera unit. In some embodiments, the computer-readable storage medium 5000 including executable instructions for monitoring medication events includes instructions for saving the accepted data relating to the time interval associated with the first medication event from the at least one camera unit into a memory. In some embodiments, the computer-readable storage medium 5000 including executable instructions for monitoring medication events includes: instructions for processing the accepted data relating to the time interval associated with the first medication event from the at least one camera unit into a transmission; and instructions for transmitting the processed data. In some embodiments, the computer-readable storage medium 5000 including executable instructions for monitoring medication events includes instructions activating an indicator in response to the identification of the end of the time interval associated with the first medication event. In some embodiments, the computer-readable storage medium 5000 including executable instructions for monitoring medication events includes: instructions for retrieving at least one attribute of the individual from memory; instructions for examining the accepted data for the at least one attribute of the individual; instructions for forming an identification result for the individual from the examination; and instructions for transmitting the identification result for the individual. In some embodiments, the computer-readable storage medium 5000 including executable instructions for monitoring medication events includes: instructions for retrieving at least one attribute of the medication from memory; instructions for examining the accepted data for the at least one attribute of the medication; instructions for forming an identification result for the medication from the examination; and instructions for transmitting the identification result for the medication. In some embodiments, the computer-readable storage medium 5000 including executable instructions for monitoring medication events includes instructions for initiating a transmission in response to the identification of the start of the time interval associated with the first medication event. In some embodiments, the computer-readable storage medium 5000 including executable instructions for monitoring medication events includes: instructions for comparing the accepted data relating to the time interval associated with the first medication event with a set of standard medication event parameters; instructions for comparing the accepted data relating to the second time interval associated with the second medication event with the set of standard medication event parameters; and instructions for activating an indicator if either the accepted data relating to the time interval associated with the first medication event or the accepted data relating to the second time interval associated with the second medication event are distinct from the set of standard medication event parameters.

In some embodiments, the computer-readable storage medium 5000 including executable instructions for monitoring medication events includes: instructions for identifying a start of the second time interval associated with the second medication event; instructions for activating an indicator in response to the identification of the start of the second time interval associated with the second medication event; instructions for activating at least one camera unit associated with the individual, the activating in response to the identification of the start of the second time interval associated with the second medication event; instructions for identifying an end of the second time interval associated with the second medication event; instructions for accepting data relating to the second time interval associated with the second medication event from the at least one camera unit; and instructions for deactivating the at least one camera unit in response to the identification of the end of the second time interval associated with the second medication event. In some embodiments, these instructions also include: instructions for comparing the time interval associated with the first medication event and the second time interval associated with the second medication event with a standard time interval; and instructions for activating an indicator if either the time interval associated with the first medication event or the second time interval associated with the second medication event are distinct from the standard time interval.

FIG. 51 illustrates aspects of a method for monitoring medication events. FIG. 51 illustrates a flowchart of the method. Block 5100 illustrates that the method is for monitoring medication event. Block 5100 includes blocks 5110, 5120, 5130, 5140, 5150, 5160, 5170. Block 5110 shows associating a time interval with a first medication event for an individual. Block 5120 illustrates identifying a start of the time interval associated with the first medication event. Block 5130 depicts activating an indicator in response to the identification of the start of the time interval associated with the first medication event. Block 5140 shows activating at least one camera unit associated with the individual, the activating in response to the identification of the start of the time interval associated with the first medication event. Block 5150 illustrates identifying an end of the time interval associated with the first medication event. Block 5160 shows accepting data relating to the time interval associated with the first medication event from the at least one camera unit. Block 5170 shows deactivating the at least one camera unit in response to the identification of the end of the time interval associated with the first medication event.

In some embodiments, the method includes further steps that can be represented in the flowchart format of FIG. 51. For example, block 5110 shows associating a time interval with a first medication event for an individual. In some embodiments, block 5110 can include associating a clock time interval with the first medication event. In some embodiments, block 5110 can include associating an elapsed time interval with the first medication event.

Block 5120 illustrates identifying a start of the time interval associated with the first medication event. In some embodiments, block 5120 includes identifying the start of a clock time interval associated with the first medication event. In some embodiments, block 5120 includes identifying the start of an elapsed time interval associated with the first medication event.

Block 5130 depicts activating an indicator in response to the identification of the start of the time interval associated with the first medication event. In some embodiments, block 5130 can include activating a visual indicator. In some embodiments, block 5130 can include activating an auditory indicator. In some embodiments, block 5130 can include activating a vibratory indicator.

Block 5140 shows activating at least one camera unit associated with the individual, the activating in response to the identification of the start of the time interval associated with the first medication event. In some embodiments, block 5140 includes activating at least one camera unit within a mobile phone. In some embodiments, block 5140 includes activating at least one camera unit within a portable computing device. In some embodiments, block 5140 includes activating at least one camera unit within a fixed position camera unit. In some embodiments, block 5140 includes activating a plurality of camera units. In some embodiments, block 5140 includes activating at least one camera unit including activating non-visual components of the at least one camera unit. In some embodiments, block 5140 includes activating at least one camera unit including a microphone. In some embodiments, block 5140 includes activating at least one camera unit including a RFID detector. In some embodiments, block 5140 can include activating at least one camera unit for video data acquisition. In some embodiments, block 5140 can include activating at least one camera unit for a series of data acquisition events. In some embodiments, block 5140 includes activating at least one camera unit for data acquisition including near-infrared (IR) data. In some embodiments, block 5140 includes activating at least one camera unit for data acquisition including thermal data. In some embodiments, block 5140 includes activating at least one micropower impulse radar (MIR) device Block 5150 illustrates identifying an end of the time interval associated with the first medication event. In some embodiments, block 5150 includes associating a clock time interval with the end of the time interval associated with the first medication event. In some embodiments, block 5150 includes associating an elapsed time interval with the end of the time interval associated with the first medication event.

Block 5160 shows accepting data relating to the time interval associated with the first medication event from the at least one camera unit. In some embodiments, block 5160 includes accepting data generated by the at least one camera unit during the time interval associated with the first medication event. In some embodiments, block 5160 includes accepting data relating to the time interval associated with the first medication event from each of a plurality of camera units.

Block 5170 shows deactivating the at least one camera unit in response to the identification of the end of the time interval associated with the first medication event. In some embodiments, block 5170 includes deactivating at least one camera unit within a mobile phone. In some embodiments, block 5170 includes deactivating at least one camera unit within a portable computing device. In some embodiments, block 5170 includes deactivating at least one camera unit within a fixed position camera unit. In some embodiments, block 5170 includes deactivating a plurality of camera units.

In some embodiments, the method illustrated in FIG. 51 can include additional steps. For example, in some embodiments the method includes activating an indicator in response to the circuitry for accepting data relating to the time interval associated with the first medication event from the at least one camera unit. For example, in some embodiments the method includes saving the accepted data relating to the time interval associated with the first medication event from the at least one camera unit into a memory, for example a memory within the computer system. For example, in some embodiments the method includes: processing the accepted data relating to the time interval associated with the first medication event from the at least one camera unit into a transmission; and transmitting the processed data, for example within units of the computer system or to a secondary computing unit. For example, in some embodiments the method includes activating an indicator in response to the identification of the end of the time interval associated with the first medication event. An indicator can be part of the computer system or a secondary computing unit. For example, in some embodiments the method includes: retrieving at least one attribute of the individual from memory; examining the accepted data for the at least one attribute of the individual; forming an identification result for the individual from the examination; and transmitting the identification result for the individual. For example, in some embodiments the method includes: retrieving at least one attribute of the medication from memory; examining the accepted data for the at least one attribute of the medication; forming an identification result for the medication from the examination; and transmitting the identification result for the medication. For example, in some embodiments the method includes initiating a transmission in response to the identification of the start of the time interval associated with the first medication event.

In some embodiments the method includes: associating a second time interval with a second medication event for the individual; identifying a start of the second time interval associated with the second medication event; activating an indicator in response to the identification of the start of the second time interval associated with the second medication event; activating at least one camera unit associated with the individual, the activating in response to the identification of the start of the second time interval associated with the second medication event; identifying an end of the second time interval associated with the second medication event; accepting data relating to the second time interval associated with the second medication event from the at least one camera unit; and deactivating the at least one camera unit in response to the identification of the end of the second time interval associated with the second medication event. The method can further include: comparing the time interval associated with the first medication event and the second time interval associated with the second medication event with a standard time interval; and activating an indicator if either the time interval associated with the first medication event or the second time interval associated with the second medication event are distinct from the standard time interval. The method can further include: comparing the accepted data relating to the time interval associated with the first medication event with a set of standard medication event parameters; comparing the accepted data relating to the second time interval associated with the second medication event with a set of standard medication event parameters; and activating an indicator if either the accepted data relating to the time interval associated with the first medication event or the accepted data relating to the second time interval associated with the second medication event are distinct from the set of standard medication event parameters.

FIG. 52 illustrates diagram of aspects of a system for monitoring medication events. The system can be a computer system such as depicted in FIG. 1 and described herein. The system 5200 depicted in FIG. 52 includes electrical circuitry. The circuitry of the system 5200 is configured to carry out a series of logical processes. As illustrated in FIG. 52, a system 5200 for monitoring medication events includes one or more circuitry components 5210, 5220, 5230, 5240, 5250, 5260, 5270, 5280, 5290, 5295. The circuitry is configured to carry out specific processes.

The system 5200 includes circuitry 5210 for identifying a start of a time interval associated with a first medication event for an individual. The system 5200 includes circuitry 5220 for activating at least one camera unit associated with the individual, the activating in response to the identification of the start of the time interval. The system 5200 includes circuitry 5230 for accepting data from the at least one camera unit, the data including both visual and non-visual data. The system 5200 includes circuitry 5240 for providing at least one sufficiency parameter for visual data from the first medication event. The system 5200 includes circuitry 5250 for providing at least one sufficiency parameter for non-visual data from the first medication event. The system 5200 includes circuitry 5260 for comparing the accepted data from the at least one camera unit with the provided at least one sufficiency parameter for visual data and with the provided at least one sufficiency parameter for non-visual data. The system 5200 includes circuitry 5270 for determining, from the comparison, if the accepted data from the at least one camera unit is sufficient. The system 5200 includes circuitry 5280 for activating an indicator in response to the determined sufficiency. The system 5200 includes circuitry 5290 for identifying an end of the time interval associated with the first medication event. The system 5200 includes circuitry 5295 for deactivating the at least one camera unit in response to the identification of the end of the time interval associated with the first medication event.

FIG. 53 illustrates additional aspects of the system shown in FIG. 52. The system 5200 includes circuitry 5210 for identifying a start of a time interval associated with a first medication event for an individual. FIG. 53 illustrates that circuitry 5210 can include one or more of circuitry 5300 and circuitry 5310. Circuitry 5300 includes circuitry for identifying the start of a clock time interval. Circuitry 5310 includes circuitry for identifying the start of an elapsed time interval. The system 5200 includes circuitry 5220 for activating at least one camera unit associated with the individual, the activating in response to the identification of the start of the time interval. FIG. 53 illustrates that circuitry 5220 can include one or more of circuitry 5320 and circuitry 5330. Circuitry 5320 includes circuitry for activating at least one camera unit within a mobile device associated with the individual. Circuitry 5330 includes circuitry for activating the at least one camera unit at a fixed location associated with the individual.

FIG. 54 illustrates additional aspects of the system shown in FIG. 52. The system 5200 includes circuitry 5230 for accepting data from the at least one camera unit, the data including both visual and non-visual data. FIG. 54 illustrates that circuitry 5230 can include one or more of circuitry 5400, 5410, 5420, 5430, 5440, 5450, 5460. Circuitry 5400 includes circuitry for accepting data including at least two visual images. Circuitry 5410 includes circuitry for accepting data including video data. Circuitry 5420 includes circuitry for accepting data including near-infrared (IR) data. Circuitry 5430 includes circuitry for accepting data including thermal data. Circuitry 5440 includes circuitry for accepting data including audio data. Circuitry 5450 includes circuitry for accepting data including RF (radio frequency) data. Circuitry 5460 includes circuitry for accepting data including micropower impulse radar (MIR)-generated data.

FIG. 55 shows additional aspects of the system shown in FIG. 52. The system 5200 includes circuitry 5240 for providing at least one sufficiency parameter for visual data from the first medication event. FIG. 55 illustrates that, in some embodiments, circuitry 5240 includes one or more of circuitry 5500, 5510, 5520. Circuitry 5500 includes circuitry for providing the at least one sufficiency parameter for visual data specific to the individual. Circuitry 5510 includes circuitry for providing the at least one sufficiency parameter for visual data including a range of values. Circuitry 5520 includes circuitry for providing the at least one sufficiency parameter for visual data including a minimum value.

Figure 56:
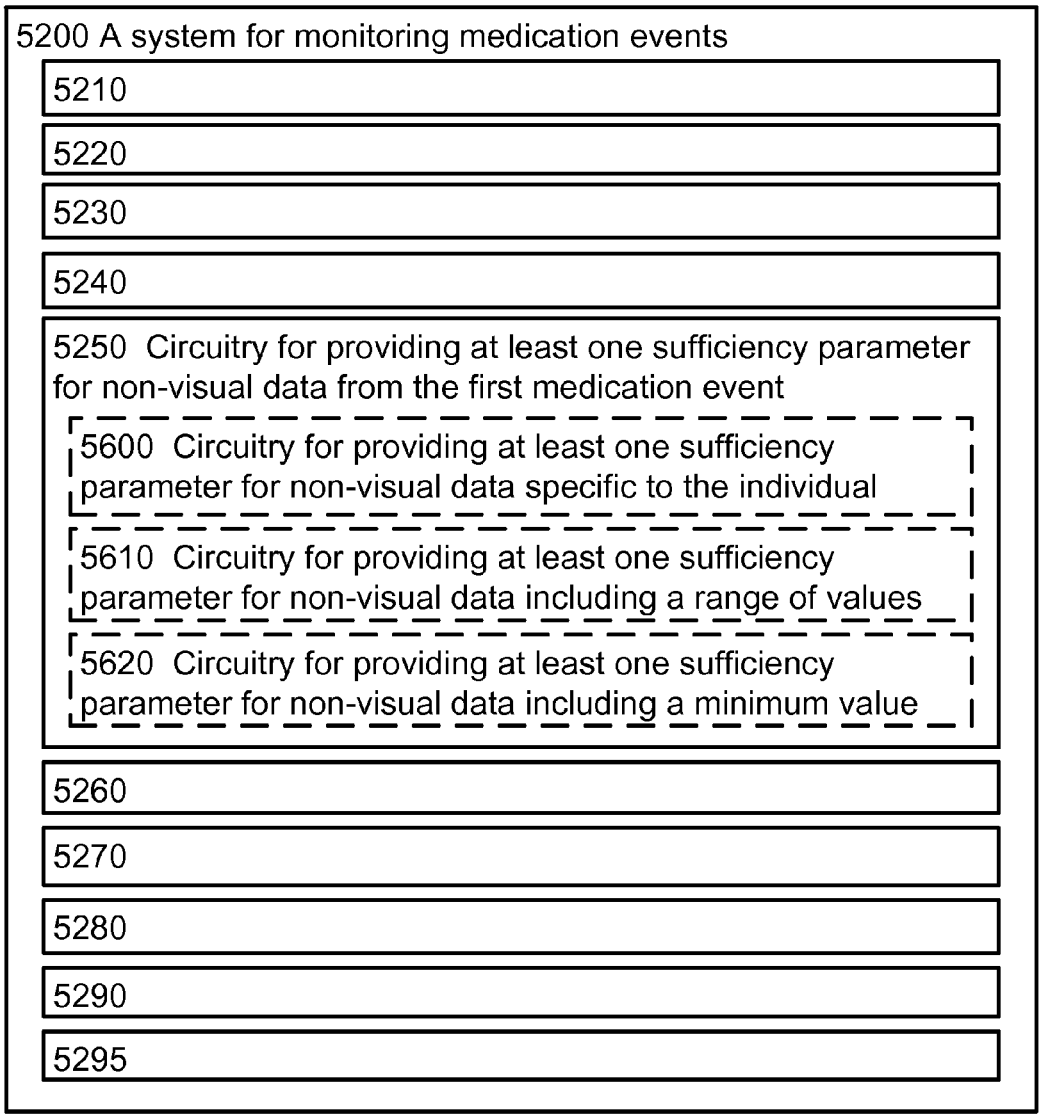
FIG. 56 shows aspects of the system of FIG. 52.

FIG. 56 shows additional aspects of the system shown in FIG. 52. The system 5200 includes circuitry 5250 for providing at least one sufficiency parameter for non-visual data from the first medication event. FIG. 56 shows that, in some embodiments, circuitry 5250 can include one or more of circuitry 5600, 5610, 5620. Circuitry 5600 includes circuitry for providing the at least one sufficiency parameter for non-visual data specific to the individual. Circuitry 5610 includes circuitry for providing the at least one sufficiency parameter for non-visual data including a range of values. Circuitry 5620 includes circuitry for providing the at least one sufficiency parameter for non-visual data including a minimum value.

FIG. 57 depicts additional aspects of the system shown in FIG. 52. The system 5200 includes circuitry 5260 for comparing the accepted data from the at least one camera unit with the provided at least one sufficiency parameter for visual data and with the provided at least one sufficiency parameter for non-visual data. FIG. 57 depicts that, in some embodiments, circuitry 5260 includes one or more of circuitry 5700, 5710, 5720. Circuitry 5700 includes circuitry for comparing the accepted data from the at least one camera unit with at least one minimum value for visual data and at least one minimum value for non-visual data. Circuitry 5710 includes circuitry for comparing the accepted data from the at least one camera unit with at least one range of values for visual data and at least one range of values for non-visual data. Circuitry 5720 includes circuitry for comparing the accepted data from the at least one camera unit with at least one sufficiency parameter for visual data specific to the individual and at least one sufficiency parameter for non-visual data specific to the individual.

FIG. 57 depicts additional aspects of the system shown in FIG. 52. The system 5200 includes circuitry 5270 for determining, from the comparison, if the accepted data from the at least one camera unit is sufficient. In some embodiments, circuitry 5270 includes circuitry 5800. Circuitry 5800 includes circuitry for determining that the accepted data from the at least one camera unit is insufficient. As illustrated in FIG. 57, the system 5200 includes circuitry 5280 for activating an indicator in response to the determined sufficiency. In some embodiments, circuitry 5280 includes one or more of circuitry 5810, 5820. Circuitry 5810 includes circuitry for activating a visual indicator. Circuitry 5820 includes circuitry for activating an audio indicator. As shown in FIG. 57, the system 5200 includes circuitry 5290 for identifying an end of the time interval associated with the first medication event. In some embodiments, circuitry 5290 includes one or more of circuitry 5830, 5840. Circuitry 5830 includes circuitry for identifying the end of a clock time interval. Circuitry 5840 includes circuitry for identifying the end of an elapsed time interval.

Figure 59:
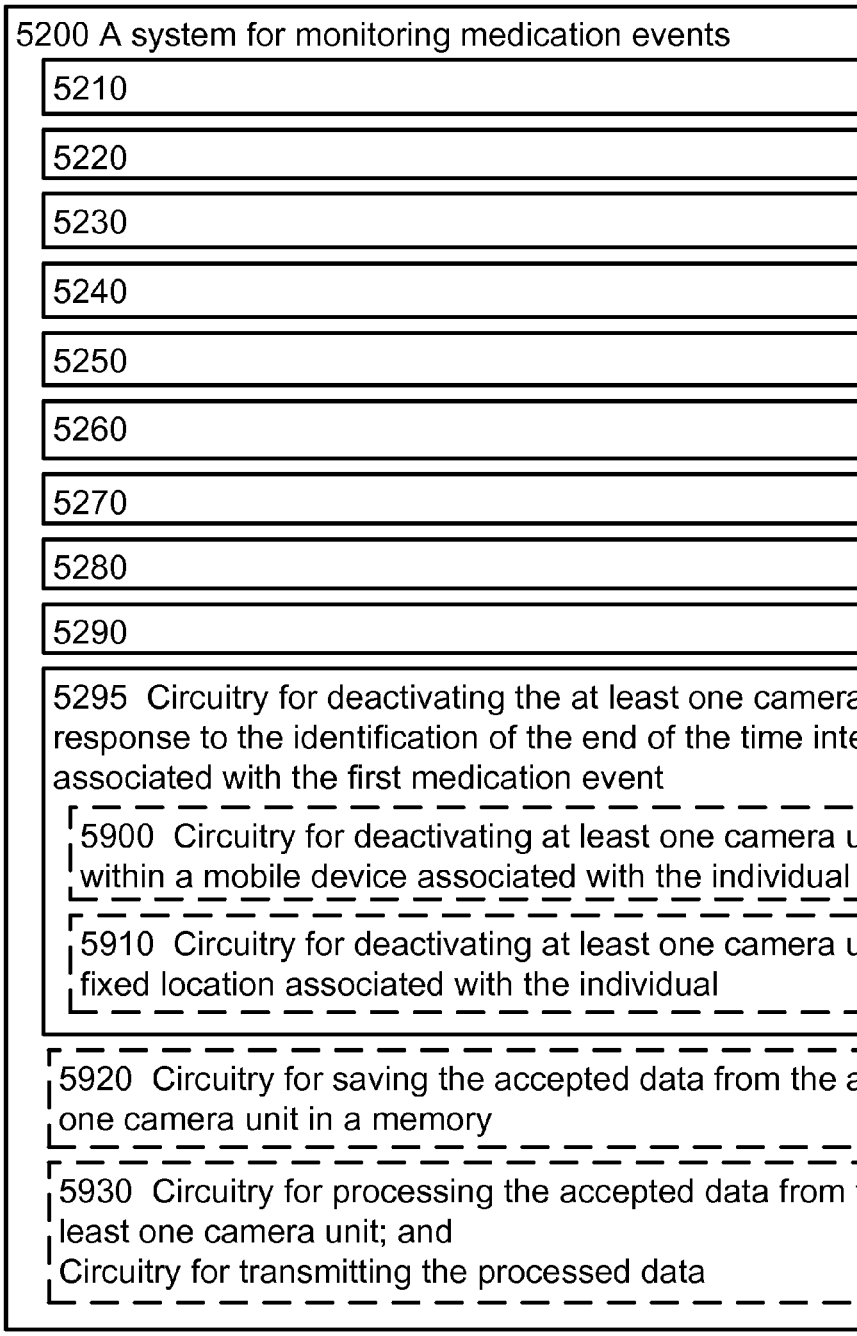
FIG. 59 shows aspects of the system of FIG. 52.

FIG. 59 shows additional aspects of the system shown in FIG. 52. The system 5200 includes circuitry 5295 for deactivating the at least one camera unit in response to the identification of the end of the time interval associated with the first medication event. In some embodiments, circuitry 5295 includes one or more of circuitry 5900, 5910. Circuitry 5900 includes circuitry for deactivating at least one camera unit within a mobile device associated with the individual. Circuitry 5910 includes circuitry for deactivating at least one camera unit at a fixed location associated with the individual. FIG. 59 also illustrates that, in some embodiments, the system 5200 can include one or more of circuitry 5920, 5930. Circuitry 5920 includes circuitry for saving the accepted data from the at least one camera unit in a memory. Circuitry 5930 includes: circuitry for processing the accepted data from the at least one camera unit; and circuitry for transmitting the processed data.

FIG. 60 illustrates additional aspects of the system depicted in FIG. 52. FIG. 60 shows that, in some embodiments, the system can include one or more of circuitry 6000, 6010, 6020, 6030, 6040. Circuitry 6000 includes circuitry for saving the determined sufficiency in a memory. Circuitry 6010 includes circuitry for transmitting the determined sufficiency. Circuitry 6020 includes circuitry for identifying, in response to the determined sufficiency, a start of a time interval associated with a supplementary medication event for the individual. Circuitry 6030 includes circuitry for activating an indicator in response to the identification of the start of the time interval associated with the first medication event. Circuitry 6040 includes circuitry for deactivating an indicator in response to the identification of the end of the time interval associated with the first medication event.

Figure 61:
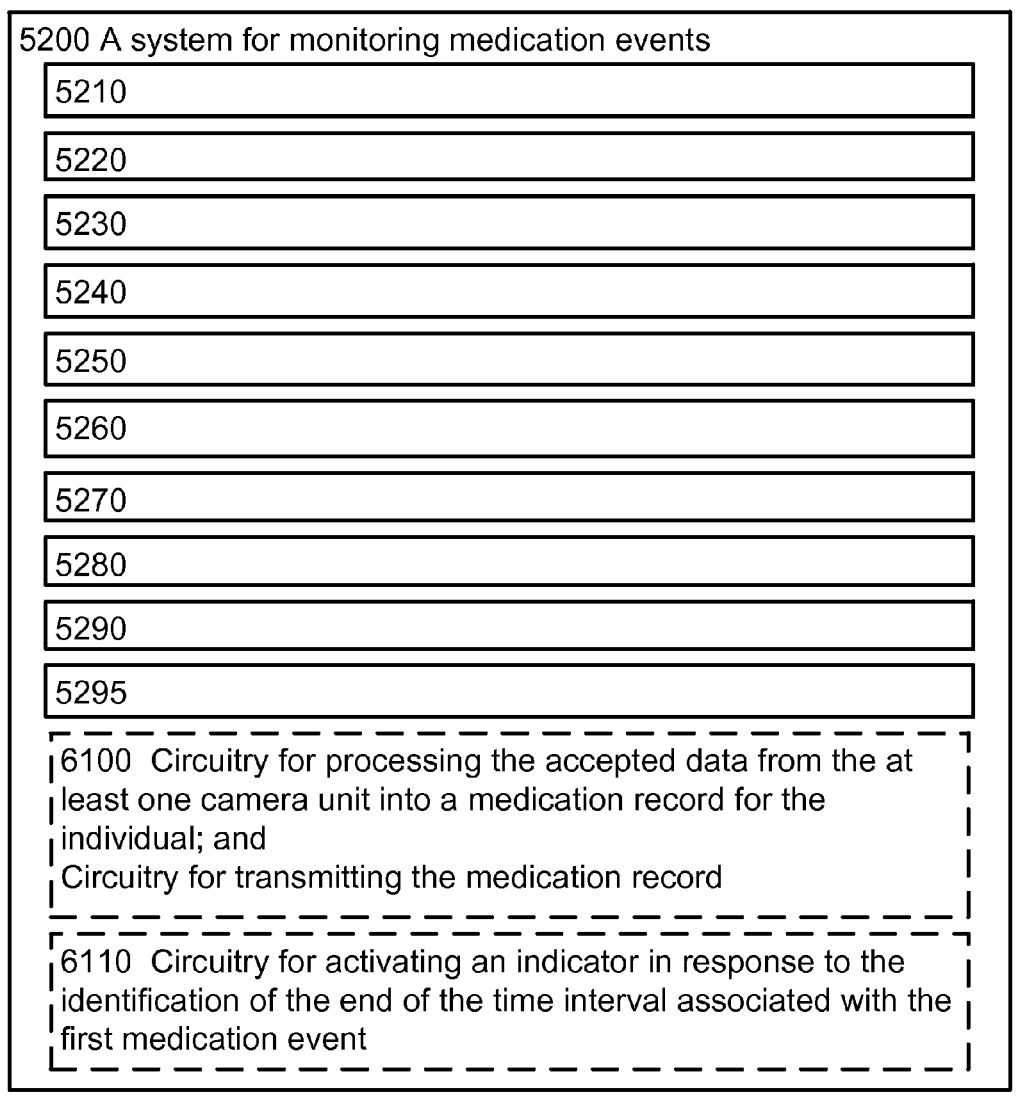
FIG. 61 illustrates aspects of the system of FIG. 52.

FIG. 61 shows additional aspects of the system depicted in FIG. 52. FIG. 61 shows that, in some embodiments, the system can include one or more of circuitry 6100, 6110. Circuitry 6100 includes: circuitry for processing the accepted data from the at least one camera unit into a medication record for the individual; and circuitry for transmitting the medication record. Circuitry 6110 includes circuitry for activating an indicator in response to the identification of the end of the time interval associated with the first medication event.

FIG. 62 depicts additional aspects of the system shown in FIG. 52. FIG. 62 shows that, in some embodiments, system 5200 for monitoring medication events can include circuitry 6200, and can also include circuitry 6210. As illustrated in FIG. 52, a system 5200 for monitoring medication events includes one or more circuitry components 5210, 5220, 5230, 5240, 5250, 5260, 5270, 5280, 5290, 5295. Although circuitry 5210, 5220, 5230, 5240, 5250, 5260, 5270, 5280, 5290, 5295 are not depicted in FIG. 62 to improve clarity, the system 5200 should be understood to include those components. Circuitry 6200 includes: circuitry for identifying a start of a second time interval associated with a second medication event for the individual; circuitry for activating the at least one camera unit associated with the individual, the activating in response to the identification of the start of the second time interval; circuitry for accepting data from the at least one camera unit, the data including both visual and non-visual data; circuitry for providing the at least one sufficiency parameter for visual data from the second medication event; circuitry for providing the at least one sufficiency parameter for non-visual data from the second medication event; circuitry for comparing the accepted data from the at least one camera unit with the provided at least one sufficiency parameter for visual data and with the provided at least one sufficiency parameter for non-visual data; circuitry for determining, from the comparison, if the accepted data from the at least one camera unit is sufficient; circuitry for activating an indicator in response to the determined sufficiency; circuitry for identifying an end of the second time interval associated with the second medication event; and circuitry for deactivating the at least one camera unit in response to the identification of the end of the time interval associated with the second medication event. In some embodiments, circuitry 6200 can include circuitry 6210. Circuitry 6210 includes circuitry for identifying, in response to the determined sufficiency of the second medication event, a start of a time interval associated with a supplementary medication event for the individual.

FIG. 63 shows aspects of a computer system 120 including at least one main computing unit 125. Although a single main computing unit 125 is illustrated in FIG. 63, in some embodiments there may be a plurality of main computing units 125. A main computing unit 125 includes computer-readable storage medium including executable instructions for monitoring medication events 6300. The computer-readable storage medium including executable instructions for monitoring medication events 6300 includes instructions 6310, 6320, 6330, 6340, 6350, 6360, 6370, 6380, 6390, 6395. Instructions 6310 include instructions for identifying a start of a time interval associated with a first medication event for an individual. Instructions 6320 include instructions for activating at least one camera unit associated with the individual, the activating in response to the identification of the start of the time interval. Instructions 6330 include instructions for accepting data from the at least one camera unit, the data including both visual and non-visual data. Instructions 6340 include instructions for providing at least one sufficiency parameter for visual data from the first medication event. Instructions 6350 include instructions for providing at least one sufficiency parameter for non-visual data from the first medication event. Instructions 6360 include instructions for comparing the accepted data from the at least one camera unit with the provided at least one sufficiency parameter for visual data and with the provided at least one sufficiency parameter for non-visual data. Instructions 6370 include instructions for determining, from the comparison, if the accepted data from the at least one camera unit is sufficient. Instructions 6380 include instructions for activating an indicator in response to the determined sufficiency. Instructions 6390 include instructions for identifying an end of the time interval associated with the first medication event. Instructions 6395 include instructions for deactivating the at least one camera unit in response to the identification of the end of the time interval associated with the first medication event.

Instructions 6310 include instructions for identifying a start of a time interval associated with a first medication event for an individual. In some embodiments, instructions 6310 include additional instructions. For example, in some embodiments, instructions 6310 include instructions for identifying the start of a clock time interval. For example, in some embodiments, instructions 6310 include instructions for identifying the start of an elapsed time interval.

Instructions 6320 include instructions for activating at least one camera unit associated with the individual, the activating in response to the identification of the start of the time interval. In some embodiments, instructions 6320 include additional instructions. For example, in some embodiments, instructions 6320 include instructions for activating at least one camera unit within a mobile device associated with the individual. For example, in some embodiments, instructions 6320 include instructions for activating the at least one camera unit at a fixed location associated with the individual.

Instructions 6330 include instructions for accepting data from the at least one camera unit, the data including both visual and non-visual data. In some embodiments, instructions 6330 include additional instructions. For example, in some embodiments, instructions 6330 include instructions for accepting data including at least two visual images. For example, in some embodiments, instructions 6330 include instructions for accepting data including video data. For example, in some embodiments, instructions 6330 include instructions for accepting data including near-infrared (IR) data. For example, in some embodiments, instructions 6330 include instructions for accepting data including thermal data. For example, in some embodiments, instructions 6330 include instructions for accepting data including audio data. For example, in some embodiments, instructions 6330 include instructions for accepting data including RF (radio frequency) data. For example, in some embodiments, instructions 6330 include instructions for accepting data including micropower impulse radar (MIR)-generated data.

Instructions 6340 include instructions for providing at least one sufficiency parameter for visual data from the first medication event. In some embodiments, instructions 6340 include additional instructions. For example, in some embodiments, instructions 6340 include instructions for providing at least one sufficiency parameter for visual data specific to the individual. For example, in some embodiments, instructions 6340 include instructions for providing at least one sufficiency parameter for visual data including a range of values. For example, in some embodiments, instructions 6340 include instructions for providing at least one sufficiency parameter for visual data including a minimum value.

Instructions 6350 include instructions for providing at least one sufficiency parameter for non-visual data from the first medication event. In some embodiments, instructions 6350 include additional instructions. For example, in some embodiments, instructions 6350 include instructions for providing at least one sufficiency parameter for non-visual data specific to the individual. For example, in some embodiments, instructions 6350 include instructions for providing at least one sufficiency parameter for non-visual data including a range of values. For example, in some embodiments, instructions 6350 include instructions for providing at least one sufficiency parameter for non-visual data including a minimum value.

Instructions 6360 include instructions for comparing the accepted data from the at least one camera unit with the provided at least one sufficiency parameter for visual data and with the provided at least one sufficiency parameter for non-visual data. In some embodiments, instructions 6360 include additional instructions. For example, in some embodiments, instructions 6360 include instructions for comparing the accepted data from the at least one camera unit with at least one minimum value for visual data and at least one minimum value for non-visual data. For example, in some embodiments, instructions 6360 include instructions for comparing the accepted data from the at least one camera unit with at least one range of values for visual data and at least one range of values for non-visual data. For example, in some embodiments, instructions 6360 include instructions for comparing the accepted data from the at least one camera unit with at least one sufficiency parameter for visual data specific to the individual and at least one sufficiency parameter for non-visual data specific to the individual.

Instructions 6370 include instructions for determining, from the comparison, if the accepted data from the at least one camera unit is sufficient. In some embodiments, instructions 6370 include additional instructions. For example, in some embodiments, instructions 6370 include instructions for determining that the accepted data from the at least one camera unit is insufficient.

Instructions 6380 include instructions for activating an indicator in response to the determined sufficiency. In some embodiments, instructions 6380 include additional instructions. For example, in some embodiments, instructions 6380 include instructions for activating a visual indicator. For example, in some embodiments, instructions 6380 include instructions for activating an audio indicator.

Instructions 6390 include instructions for identifying an end of the time interval associated with the first medication event. In some embodiments, instructions 6390 include additional instructions. For example, in some embodiments, instructions 6390 include instructions for identifying the end of a clock time interval. For example, in some embodiments, instructions 6380 include instructions for identifying the end of an elapsed time interval.

Instructions 6395 include instructions for deactivating the at least one camera unit in response to the identification of the end of the time interval associated with the first medication event. In some embodiments, instructions 6395 include additional instructions. For example, in some embodiments, instructions 6395 include instructions for deactivating at least one camera unit within a mobile device associated with the individual. For example, in some embodiments, instructions 6395 include instructions for deactivating at least one camera unit at a fixed location associated with the individual.

As illustrated in FIG. 63, a computer-readable storage medium including executable instructions for monitoring medication events 6300 includes instructions 6310, 6320, 6330, 6340, 6350, 6360, 6370, 6380, 6390, 6395. In some embodiments, the executable instructions for monitoring medication events 6300 illustrated in FIG. 63 includes additional sets of instructions. In some embodiments, the computer-readable storage medium including executable instructions for monitoring medication events 6300 includes instructions for saving the accepted data from the at least one camera unit in a memory. In some embodiments, the computer-readable storage medium including executable instructions for monitoring medication events 6300 includes: instructions for processing the accepted data from the at least one camera unit; and instructions for transmitting the processed data. In some embodiments, the computer-readable storage medium including executable instructions for monitoring medication events 6300 includes instructions for saving the determined sufficiency in a memory. In some embodiments, the computer-readable storage medium including executable instructions for monitoring medication events 6300 includes instructions for transmitting the determined sufficiency. In some embodiments, the computer-readable storage medium including executable instructions for monitoring medication events 6300 includes instructions for identifying, in response to the determined sufficiency, a start of a time interval associated with a supplementary medication event for the individual. In some embodiments, the computer-readable storage medium including executable instructions for monitoring medication events 6300 includes instructions for activating an indicator in response to the identification of the start of the time interval associated with the first medication event. In some embodiments, the computer-readable storage medium including executable instructions for monitoring medication events 6300 includes instructions for deactivating an indicator in response to the identification of the end of the time interval associated with the first medication event. In some embodiments, the computer-readable storage medium including executable instructions for monitoring medication events 6300 includes instructions for activating an indicator in response to the identification of the end of the time interval associated with the first medication event. In some embodiments, the computer-readable storage medium including executable instructions for monitoring medication events 6300 includes: instructions for processing the accepted data from the at least one camera unit into a medication record for the individual; and instructions for transmitting the medication record. In some embodiments, the computer-readable storage medium including executable instructions for monitoring medication events 6300 includes: instructions for identifying a start of a second time interval associated with a second medication event for the individual; instructions for activating the at least one camera unit associated with the individual, the activating in response to the identification of the start of the second time interval; instructions for accepting data from the at least one camera unit, the data including both visual and non-visual data; instructions for providing the at least one sufficiency parameter for visual data from the second medication event; instructions for providing the at least one sufficiency parameter for non-visual data from the second medication event; instructions for comparing the accepted data from the at least one camera unit with the provided at least one sufficiency parameter for visual data and with the provided at least one sufficiency parameter for non-visual data; instructions for determining, from the comparison, if the accepted data from the at least one camera unit is sufficient; instructions for activating an indicator in response to the determined sufficiency; instructions for identifying an end of the second time interval associated with the second medication event; and instructions for deactivating the at least one camera unit in response to the identification of the end of the time interval associated with the second medication event. In some embodiments, the computer-readable storage medium including executable instructions for monitoring medication events 6300 includes instructions for identifying, in response to the determined sufficiency of the second medication event, a start of a time interval associated with a supplementary medication event for the individual.

FIG. 64 illustrates a flowchart of a method 6400 for monitoring medication events. These method steps can be carried out, for example, by a computer system (e.g. item 120 in FIG. 1). FIG. 64 shows that the method includes a series of steps, 6410, 6420, 6430, 6440, 6450, 6460, 6470, 6480, 6490, 6495. Method step 6410 includes identifying a start of a time interval associated with a first medication event for an individual. Method step 6420 includes activating at least one camera unit associated with the individual, the activating in response to the identification of the start of the time interval. Method step 6430 includes accepting data from the at least one camera unit, the data including both visual and non-visual data. Method step 6440 includes providing at least one sufficiency parameter for visual data from the first medication event. Method step 6450 includes providing at least one sufficiency parameter for non-visual data from the first medication event. Method step 6460 includes comparing the accepted data from the at least one camera unit with the provided at least one sufficiency parameter for visual data and with the provided at least one sufficiency parameter for non-visual data. Method step 6470 includes determining, from the comparison, if the accepted data from the at least one camera unit is sufficient. Method step 6480 includes activating an indicator in response to the determined sufficiency. Method step 6490 includes identifying an end of the time interval associated with the first medication event. Method step 6495 includes deactivating the at least one camera unit in response to the identification of the end of the time interval associated with the first medication event.

In some embodiments, the flowchart of the method illustrated in FIG. 64 can be shown with further details. For example, method step 6410 includes identifying a start of a time interval associated with a first medication event for an individual. In some embodiments, method step 6410 can include identifying the start of a clock time interval. In some embodiments, method step 6410 can include identifying the start of an elapsed time interval.

Method step 6420 includes activating at least one camera unit associated with the individual, the activating in response to the identification of the start of the time interval. In some embodiments, method step 6420 can include activating at least one camera unit within a mobile device associated with the individual. In some embodiments, method step 6420 can include activating at least one camera unit at a fixed location associated with the individual.

Method step 6430 includes accepting data from the at least one camera unit, the data including both visual and non-visual data. In some embodiments, method step 6430 can include accepting data including at least two visual images. In some embodiments, method step 6430 can include accepting data including video data. In some embodiments, method step 6430 can include accepting data including near-infrared (IR) data. In some embodiments, method step 6430 can include accepting data including thermal data. In some embodiments, method step 6430 can include accepting data including audio data. In some embodiments, method step 6430 can include accepting data including RF (radio frequency) data. In some embodiments, method step 6430 can include accepting data including micropower impulse radar (MIR)-generated data.

Method step 6440 includes providing at least one sufficiency parameter for visual data from the first medication event. In some embodiments, method step 6440 can include providing at least one sufficiency parameter for visual data specific to the individual. In some embodiments, method step 6440 can include providing at least one sufficiency parameter for visual data including a range of values. In some embodiments, method step 6440 can include providing at least one sufficiency parameter for visual data including a minimum value.

Method step 6450 includes providing at least one sufficiency parameter for visual data from the first medication event. In some embodiments, method step 6450 can include providing at least one sufficiency parameter for non-visual data specific to the individual. In some embodiments, method step 6450 can include providing at least one sufficiency parameter for non-visual data including a range of values. In some embodiments, method step 6450 can include providing at least one sufficiency parameter for non-visual data including a minimum value.

Method step 6460 includes comparing the accepted data from the at least one camera unit with the provided at least one sufficiency parameter for visual data and with the provided at least one sufficiency parameter for non-visual data. In some embodiments, method step 6460 can include comparing the accepted data from the at least one camera unit with at least one minimum value for visual data and at least one minimum value for non-visual data. In some embodiments, method step 6460 can include comparing the accepted data from the at least one camera unit with at least one range of values for visual data and at least one range of values for non-visual data. In some embodiments, method step 64560 can include comparing the accepted data from the at least one camera unit with at least one sufficiency parameter for visual data specific to the individual and at least one sufficiency parameter for non-visual data specific to the individual.

Method step 6470 includes determining, from the comparison, if the accepted data from the at least one camera unit is sufficient. In some embodiments, method step 6470 can include determining that the accepted data from the at least one camera unit is insufficient.

Method step 6480 includes activating an indicator in response to the determined sufficiency. In some embodiments, method step 6480 can include activating a visual indicator. In some embodiments, method step 6480 can include activating an audio indicator.

Method step 6490 includes identifying an end of the time interval associated with the first medication event. In some embodiments, method step 6490 can include identifying the end of a clock time interval. In some embodiments, method step 6490 can include identifying the end of an elapsed time interval.

Method step 6495 includes deactivating the at least one camera unit in response to the identification of the end of the time interval associated with the first medication event. In some embodiments, method step 6495 can include deactivating at least one camera unit within a mobile device associated with the individual. In some embodiments, method step 6495 can include deactivating at least one camera unit at a fixed location associated with the individual.

In some embodiments, the flowchart illustrated in FIG. 64 can include additional steps. For example, the method can include saving the accepted data from the at least one camera unit in a memory. For example, the method can include: processing the accepted data from the at least one camera unit; and transmitting the processed data. For example, the method can include saving the determined sufficiency in a memory. For example, the method can include transmitting the determined sufficiency. For example, the method can include identifying, in response to the determined sufficiency, a start of a time interval associated with a supplementary medication event for the individual. For example, the method can include activating an indicator in response to the identification of the start of the time interval associated with the first medication event. For example, the method can include deactivating an indicator in response to the identification of the end of the time interval associated with the first medication event. For example, the method can include activating an indicator in response to the identification of the end of the time interval associated with the first medication event. For example, the method can include: processing the accepted data from the at least one camera unit into a medication record for the individual; and transmitting the medication record.

In some embodiments, the flowchart shown in FIG. 64 can include additional steps. For example, the method can include: identifying a start of a second time interval associated with a second medication event for the individual; activating the at least one camera unit associated with the individual, the activating in response to the identification of the start of the second time interval; accepting data from the at least one camera unit, the data including both visual and non-visual data; providing the at least one sufficiency parameter for visual data from the second medication event; providing the at least one sufficiency parameter for non-visual data from the second medication event; comparing the accepted data from the at least one camera unit with the provided at least one sufficiency parameter for visual data and with the provided at least one sufficiency parameter for non-visual data; determining, from the comparison, if the accepted data from the at least one camera unit is sufficient; activating an indicator in response to the determined sufficiency; identifying an end of the second time interval associated with the second medication event; and deactivating the at least one camera unit in response to the identification of the end of the time interval associated with the second medication event. This method can also include: identifying, in response to the determined sufficiency of the second medication event, a start of a time interval associated with a supplementary medication event for the individual.

FIG. 65 illustrates further aspects of the systems and methods described herein. FIG. 65 illustrates diagram of aspects of a system for monitoring medication events. The system can be a computer system such as depicted in FIG. 1 and described herein. The system 6500 depicted in FIG. 65 includes electrical circuitry. The circuitry of the system 6500 is configured to carry out a series of logical processes. As illustrated in FIG. 65, a system 6500 for monitoring medication events relating to an individual includes one or more circuitry components 6510, 6520, 6530, 6540, 6550, 6560, 6570, 6580, 6590, 6595. The circuitry is configured to carry out specific processes.

The system 6500 includes circuitry 6510 for accepting first data from a camera unit associated with an individual. The system 6500 includes circuitry 6520 for providing a set of medication intervention parameters for the individual. The system 6500 includes circuitry 6530 for comparing the accepted first data from the camera unit associated with the individual with the provided set of medication intervention parameters for the individual. The system 6500 includes circuitry 6540 for determining if the accepted first data is within the provided set of medication intervention parameters. The system 6500 includes circuitry 6550 for activating at least one indicator in response to the first determination. The system 6500 includes circuitry 6560 for accepting second data from the camera unit associated with the individual, the second data obtained after the activation of the at least one indicator. The system 6500 includes circuitry 6570 for analyzing the accepted second data for at least one attribute relating to the medication event. The system 6500 includes circuitry 6580 for comparing the accepted second data with the provided set of medication intervention parameters for the individual. The system 6500 includes circuitry 6590 for determining if the accepted second data is within the provided set of medication intervention parameters. The system 6500 includes circuitry 6595 for activating the at least one indicator in response to the second determination.

FIG. 66 illustrates other aspects of the system 6500 depicted in FIG. 65. As shown in FIG. 66, in some embodiments the circuitry 6510 for accepting first data from a camera unit associated with an individual includes additional aspects. FIG. 66 illustrates that in some embodiments, circuitry 6510 can include one or more of circuitry 6600, 6610, 6620, 6630, 6640, 6650. Circuitry 6600 includes circuitry for accepting visual data and accepting non-visual data. Circuitry 6610 includes circuitry for accepting data from a camera unit integral to a mobile device. Circuitry 6620 includes circuitry for accepting data from a camera unit integral to a fixed-location device. Circuitry 6630 includes circuitry for accepting data including at least two visual images. Circuitry 6640 includes circuitry for accepting data including video data. Circuitry 6650 includes circuitry for accepting data including near-infrared (IR) data.

FIG. 67 illustrates further aspects of the circuitry depicted in FIG. 65. FIG. 67 illustrates that, in some embodiments, circuitry 6510 for accepting first data from a camera unit associated with an individual includes additional aspects. FIG. 67 illustrates that in some embodiments, circuitry 6510 can include one or more of circuitry 6700, 6710, 6720, 6730. Circuitry 6700 includes circuitry for accepting data including radio frequency (RF) data. Circuitry 6710 includes circuitry for accepting data including data from a micropower impulse radar (MIR) device.

FIG. 67 also shows that, in some embodiments, the circuitry 6520 of FIG. 65 can also include one or more of circuitry 6740, 6750. The system 6500 includes circuitry 6520 for providing a set of medication intervention parameters for the individual. Circuitry 6720 includes circuitry for accepting data including thermal data. Circuitry 6730 includes circuitry for accepting data including audio data.

FIG. 68 depicts further aspects of the circuitry depicted in FIG. 65. FIG. 68 illustrates that, in some embodiments, circuitry 6520 for providing a set of medication intervention parameters for the individual includes additional aspects.

FIG. 68 illustrates that in some embodiments, circuitry 6520 can include one or more of circuitry 6800, 6810, 6820, 6830. Circuitry 6800 includes providing the set of medication intervention parameters for the individual including audio parameters. Circuitry 6810 includes circuitry for providing the set of medication intervention parameters for the individual including near-infrared (IR) parameters. Circuitry 6820 includes circuitry for providing the set of medication intervention parameters for the individual including thermal parameters. Circuitry 6830 includes circuitry for providing the set of medication intervention parameters for the individual including micropower impulse radar parameters.

FIG. 69 shows aspects of the circuitry illustrated in FIG. 65. FIG. 69 illustrates that, in some embodiments, circuitry 6530 for comparing the accepted first data from the camera unit associated with the individual with the provided set of medication intervention parameters for the individual can include one or more of circuitry 6900, 6910, 6920, 6930. Circuitry 6900 includes circuitry for comparing the accepted first data with at least one minimum sufficiency parameter. Circuitry 6910 includes circuitry for comparing the accepted first data with a set of parameters associated with the individual. Circuitry 6920 includes circuitry for comparing the accepted first data with a range of sufficiency parameters. Circuitry 6930 includes circuitry for comparing the accepted first data with a series of minimum medication intervention parameters.

FIG. 70 shows aspects of the system 6500 illustrated in FIG. 65. FIG. 70 depicts that, in some embodiments, circuitry 6540 for determining if the accepted first data is within the provided set of medication intervention parameters can include circuitry 7000. Circuitry 7000 includes circuitry for determining that the accepted first data either is within the provided set of medication intervention parameters or is not within the provided set of medication intervention parameters. FIG. 70 also depicts that, in some embodiments, circuitry 6550 for activating at least one indicator in response to the first determination can include one or more of circuitry 7010, 7020, or 7030. Circuitry 7010 includes circuitry for activating a visual indicator. Circuitry 7020 includes circuitry for activating an audio indicator. Circuitry 7030 includes circuitry for activating a vibratory indicator.

FIG. 71 depicts aspects of the system 6500 illustrated in FIG. 65. FIG. 71 shows that, in some embodiments, circuitry 6560 for accepting second data from the camera unit associated with the individual, the second data obtained after the activation of the at least one indicator can include one or more of circuitry 7100, 7110. Circuitry 7100 includes circuitry for accepting second data from at least one camera unit, the second data including at least one time value. Circuitry 7110 includes circuitry for accepting data including visual data, non-visual data, and at least one time value. FIG. 71 also shows that, in some embodiments, circuitry 6570 for analyzing the accepted second data for at least one attribute relating to the medication event can include circuitry 7120. Circuitry 7120 includes: circuitry for presenting at least one attribute relating to a medication event; and circuitry for analyzing the accepted second data for the at least one attribute relating to a medication event.

FIG. 72 shows aspects of the system 6500 illustrated in FIG. 65. FIG. 72 depicts that, in some embodiments, circuitry 6570 for analyzing the accepted second data for at least one attribute relating to the medication event can include one or more of circuitry 7200, 7210. Circuitry 7200 includes circuitry for analyzing the accepted second data for at least one visual attribute. Circuitry 7210 includes circuitry for analyzing the accepted second data for at least one non-visual attribute. FIG. 72 also depicts that, in some embodiments, circuitry 6580 for comparing the accepted second data with the provided set of medication intervention parameters for the individual includes circuitry 7220. Circuitry 7220 includes circuitry for comparing both visual data and non-visual data.

FIG. 73 shows that the system 6500 illustrated in FIG. 65 can also include circuitry 7300, 7310, 7320, 7330. FIG. 73 shows that, in some embodiments, circuitry 6590 for determining if the accepted second data is within the provided set of medication intervention parameters can include circuitry 7300. Circuitry 7300 includes circuitry for determining that the accepted second data either is within the provided set of medication intervention parameters or is not within the provided set of medication intervention parameters. FIG. 73 shows that, in some embodiments, circuitry 6595 for activating the at least one indicator in response to the second determination can include one or more of circuitry 7310, 7320, 7330. Circuitry 73010 includes circuitry for activating at least one visual indicator. Circuitry 7320 includes circuitry for activating at least one audio indicator. Circuitry 7330 includes circuitry for activating at least one vibratory indicator.

FIG. 74 shows additional aspects of the system 6500 shown in FIG. 65. FIG. 74 depicts that, in some embodiments, system 6500 can include one or more of circuitry 7400, 7410, 7420, 7430. Circuitry 7400 includes: circuitry for presenting at least one attribute of the individual; and circuitry for analyzing the accepted first data for the at least one attribute of the individual. Circuitry 7410 includes: circuitry for presenting at least one attribute of the individual; and circuitry for analyzing the accepted second data for the at least one attribute of the individual. Circuitry 7420 includes circuitry for saving the accepted first data in a memory. Circuitry 7430 includes circuitry for saving the accepted second data in a memory.

FIG. 75 depicts additional aspects of the system 6500 shown in FIG. 65. FIG. 75 illustrates that, in some embodiments, system 6500 can include one or more of circuitry 7500, 7510. Circuitry 7500 includes: circuitry for processing the at least one accepted first data; circuitry for processing the at least one accepted second data; circuitry for integrating the processed at least one accepted first data and the processed at least one accepted second data into a medication record; and circuitry for saving the medication record in a memory. Circuitry 7510 includes: circuitry for processing the determination if the accepted first data is within the provided set of medication intervention parameters into a first result; and circuitry for transmitting the first result.

FIG. 76 illustrates additional aspects of the system 6500 shown in FIG. 65. FIG. 76 shows that, in some embodiments, system 6500 can include circuitry 7600. Circuitry 7600 includes: circuitry for processing the determination if the accepted second data is within the provided set of medication intervention parameters into a second result; and circuitry for transmitting the second result.

FIG. 77 depicts additional aspects of the system 6500 shown in FIG. 65. FIG. 77 illustrates that, in some embodiments, system 6500 can include circuitry 7710. Circuitry 7710 includes: circuitry for accepting third data from the camera unit associated with the individual, the third data obtained after the activation of the at least one indicator in response to the second determination; circuitry for analyzing the accepted third data for the at least one attribute relating to the medication event; circuitry for comparing the accepted third data with the provided set of medication intervention parameters for the individual; circuitry for determining if the accepted third data is within the provided set of medication intervention parameters; and circuitry for activating the at least one indicator in response to the third determination.

FIG. 78 shows aspects of a computer system 120 including at least one main computing unit 125. Although a single main computing unit 125 is illustrated in FIG. 78, in some embodiments there may be a plurality of main computing units 125. A main computing unit 125 includes computer-readable storage medium including executable instructions for monitoring medication events 7800. The computer-readable storage medium including executable instructions for monitoring medication events 7800 includes instructions 7810, 7820, 7830, 7840, 7850, 7860, 7870, 7880, 7890, 7895. Instructions 7810 include instructions for accepting first data from a camera unit associated with an individual. Instructions 7820 include instructions for providing a set of medication intervention parameters for the individual. Instructions 7830 include instructions for comparing the accepted first data from the camera unit associated with the individual with the provided set of medication intervention parameters for the individual. Instructions 7840 include instructions for determining if the accepted first data is within the provided set of medication intervention parameters. Instructions 7850 include instructions for activating at least one indicator in response to the first determination. Instructions 7860 include instructions for accepting second data from the camera unit associated with the individual, the second data obtained after the activation of the at least one indicator. Instructions 7870 include instructions for analyzing the accepted second data for at least one attribute relating to the medication event. Instructions 7880 include instructions for comparing the accepted second data with the provided set of medication intervention parameters for the individual. Instructions 7890 include instructions for determining if the accepted second data is within the provided set of medication intervention parameters. Instructions 7895 include instructions for activating the at least one indicator in response to the second determination.

Some embodiments include a computer-readable storage medium including executable instructions for monitoring medication events 7800 including additional aspects. In some embodiments, instructions 7810 for accepting first data from a camera unit associated with an individual include one or more additional instructions. For example, instructions 7810 can include instructions for accepting visual data and accepting non-visual data. Instructions 7810 can also include instructions for accepting data from a camera unit integral to a mobile device. Instructions 7810 can include instructions for accepting data from a camera unit integral to a fixed-location device. Instructions 7810 can include instructions for accepting data including at least two visual images. Instructions 7810 can include instructions for accepting data including video data. Instructions 7810 can include instructions for accepting data including near-infrared (IR) data. Instructions 7810 can include instructions for accepting data including radio frequency (RF) data. Instructions 7810 can include instructions for accepting data including data from a micropower impulse radar (MIR) device. Instructions 7810 can include instructions for accepting data including thermal data. Instructions 7810 can include instructions for accepting data including audio data.

In some embodiments, instructions 7820 for providing a set of medication intervention parameters for the individual include one or more additional instructions. For example, instructions 7820 can include instructions for providing the set of medication intervention parameters for the individual including time parameters. Instructions 7820 can include instructions for providing the set of medication intervention parameters for the individual including visual parameters. Instructions 7820 can include instructions for providing the set of medication intervention parameters for the individual including audio parameters. Instructions 7820 can include instructions for providing the set of medication intervention parameters for the individual including near-infrared (IR) parameters. Instructions 7820 can include instructions for providing the set of medication intervention parameters for the individual including thermal parameters. Instructions 7820 can include instructions for providing the set of medication intervention parameters for the individual including micropower impulse radar parameters.

In some embodiments, instructions 7830 for comparing the accepted first data from the camera unit associated with the individual with the provided set of medication intervention parameters for the individual can include one or more additional instructions. For example, in some embodiments instructions 7830 can include instructions for comparing the accepted first data with at least one minimum sufficiency parameter. For example, in some embodiments instructions 7830 can include instructions for comparing the accepted first data with a set of parameters associated with the individual. For example, in some embodiments instructions 7830 can include instructions for comparing the accepted first data with a range of sufficiency parameters. For example, in some embodiments instructions 7830 can include instructions for comparing the accepted first data with a series of minimum medication intervention parameters.

In some embodiments, instructions 7840 for determining if the accepted first data is within the provided set of medication intervention parameters can include one or more additional instructions. For example, in some embodiments instructions 7840 can include instructions for determining that the accepted first data either is within the provided set of medication intervention parameters or is not within the provided set of medication intervention parameters.

In some embodiments, instructions 7850 for activating at least one indicator in response to the first determination can include one or more additional instructions. For example, in some embodiments instructions 7850 can include instructions for activating a visual indicator. In some embodiments, instructions 7850 can include instructions for activating an audio indicator. In some embodiments, instructions 7850 can include instructions for activating a vibratory indicator.

In some embodiments, instructions 7860 include instructions for accepting second data from the camera unit associated with the individual, the second data obtained after the activation of the at least one indicator can include one or more additional instructions. For example, in some embodiments instructions 7860 can include instructions for accepting second data from the at least one camera unit, the second data including at least one time value. In some embodiments, instructions 7860 can include instructions for accepting data including visual data, non-visual data, and at least one time value.

In some embodiments, instructions 7870 for analyzing the accepted second data for at least one attribute relating to the medication event can include one or more additional instructions. For example, in some embodiments instructions 7870 can include: instructions for presenting at least one attribute relating to the medication event; and instructions for analyzing the accepted second data for the at least one attribute relating to the medication event. In some embodiments, instructions 7870 can include instructions for analyzing the accepted second data for at least one visual attribute. In some embodiments, instructions 7870 can include instructions for analyzing the accepted second data for at least one non-visual attribute.

In some embodiments, instructions 7880 for comparing the accepted second data with the provided set of medication intervention parameters for the individual can include can include one or more additional instructions. For example, in some embodiments instructions 7880 can include instructions for comparing both visual data and non-visual data.

In some embodiments, instructions 7890 for determining if the accepted second data is within the provided set of medication intervention parameters can include one or more additional instructions. For example, in some embodiments instructions 7890 can include instructions for determining that the accepted second data either is within the provided set of medication intervention parameters or is not within the provided set of medication intervention parameters.

In some embodiments, instructions 7895 for activating the at least one indicator in response to the second determination includes one or more additional sets of instructions. For example, the instructions 7895 can include instructions for activating at least one audio indicator. For example, the instructions 7895 can include instructions for activating at least one vibratory indicator.

In some embodiments, the computer-readable storage medium including executable instructions for monitoring medication events 7800 includes one or more sets of additional instructions. For example, the computer-readable storage medium including executable instructions for monitoring medication events 7800 can include instructions including: instructions for presenting at least one attribute of the individual; and instructions for analyzing the accepted first data for the at least one attribute of the individual. For example, the computer-readable storage medium including executable instructions for monitoring medication events 7800 can include instructions including: instructions for presenting at least one attribute of the individual; and instructions for analyzing the accepted second data for the at least one attribute of the individual. For example, the computer-readable storage medium including executable instructions for monitoring medication events 7800 can include instructions including: instructions for saving the accepted first data in a memory. For example, the computer-readable storage medium including executable instructions for monitoring medication events 7800 can include instructions including: instructions for saving the accepted second data in a memory. For example, the computer-readable storage medium including executable instructions for monitoring medication events 7800 can include instructions including: instructions for processing the at least one accepted first data; instructions for processing the at least one accepted second data; instructions for integrating the processed at least one accepted first data and the processed at least one accepted second data into a medication record; and instructions for saving the medication record in a memory. For example, the computer-readable storage medium including executable instructions for monitoring medication events 7800 can include instructions including: instructions for processing the determination if the accepted first data is within the provided set of medication intervention parameters into a first result; and instructions for transmitting the first result. For example, the computer-readable storage medium including executable instructions for monitoring medication events 7800 can include instructions including: instructions for processing the determination if the accepted second data is within the provided set of medication intervention parameters into a second result; and instructions for transmitting the second result. For example, the computer-readable storage medium including executable instructions for monitoring medication events 7800 can include instructions including: instructions for accepting third data from the camera unit associated with the individual, the third data obtained after the activation of the at least one indicator in response to the second determination; instructions for analyzing the accepted third data for the at least one attribute relating to the medication event; instructions for comparing the accepted third data with the provided set of medication intervention parameters for the individual; instructions for determining if the accepted third data is within the provided set of medication intervention parameters; and instructions for activating the at least one indicator in response to the third determination.

FIG. 79 illustrates a flowchart of a method 7900 for monitoring medication events. These method steps can be carried out, for example, by a computer system (e.g. item 120 in FIG. 1). FIG. 79 shows that the method includes a series of steps, 7910, 7920, 7930, 7940, 7950, 7960, 7970, 7980, 7790, 7995. Method step 7910 includes accepting first data from a camera unit associated with an individual. Method step 7920 includes providing a set of medication intervention parameters for the individual. Method step 7930 includes comparing the accepted first data from the camera unit associated with the individual with the provided set of medication intervention parameters for the individual. Method step 7940 includes determining if the accepted first data is within the provided set of medication intervention parameters. Method step 7950 includes activating at least one indicator in response to the first determination. Method step 7960 includes accepting second data from the camera unit associated with the individual, the second data obtained after the activation of the at least one indicator. Method step 7970 includes analyzing the accepted second data for at least one attribute relating to the medication event. Method step 7980 includes comparing the accepted second data with the provided set of medication intervention parameters for the individual. Method step 7990 includes determining if the accepted second data is within the provided set of medication intervention parameters. Method step 7995 includes activating the at least one indicator in response to the second determination.

In some embodiments, the flowchart of a method 7900 for monitoring medication events illustrated in FIG. 79 includes additional aspects. As illustrated in FIG. 79, method step 7910 includes accepting first data from a camera unit associated with an individual. Method step 7910 can include one or more additional steps. For example, method step 7910 can include accepting visual data and accepting non-visual data. For example, method step 7910 can include accepting data from a camera unit integral to a mobile device. For example, method step 7910 can include accepting data from a camera unit integral to a fixed-location device. For example, method step 7910 can include accepting data including at least two visual images. For example, method step 7910 can include accepting data including video data. For example, method step 7910 can include accepting data including near-infrared (IR) data. For example, method step 7910 can include accepting data including radio frequency (RF) data. For example, method step 7910 can include accepting data including data from a micropower impulse radar (MIR) device. For example, method step 7910 can include accepting data including thermal data. For example, method step 7910 can include accepting data including audio data.

As illustrated in FIG. 79, method step 7920 includes providing a set of medication intervention parameters for the individual. Method step 7920 can include one or more additional steps. For example, method step 7920 can include providing a set of medication intervention parameters for the individual including time parameters. For example, method step 7920 can include providing a set of medication intervention parameters for the individual including visual parameters. For example, method step 7920 can include providing a set of medication intervention parameters for the individual including audio parameters. For example, method step 7920 can include providing a set of medication intervention parameters for the individual including near-infrared (IR) parameters. For example, method step 7920 can include providing a set of medication intervention parameters for the individual including thermal parameters. For example, method step 7920 can include providing a set of medication intervention parameters for the individual including micropower impulse radar parameters.

As shown in FIG. 79, method step 7930 includes comparing the accepted first data from the camera unit associated with the individual with the provided set of medication intervention parameters for the individual. Method step 7930 can include one or more additional steps. For example, method step 7930 can include comparing the accepted first data with at least one minimum sufficiency parameter. For example, method step 7930 can include comparing the accepted first data with a set of parameters associated with the individual. For example, method step 7930 can include comparing the accepted first data with a range of sufficiency parameters. For example, method step 7920 can include comparing the accepted first data with a series of minimum medication intervention parameters.

As depicted in FIG. 79, method step 7940 includes determining if the accepted first data is within the provided set of medication intervention parameters. Method step 7940 can include one or more additional steps. For example, method step 7940 can include determining that the accepted first data either is within the provided set of medication intervention parameters or is not within the provided set of medication intervention parameters.

As shown in FIG. 79, method step 7950 includes activating at least one indicator in response to the first determination. Method step 7950 can include one or more additional steps. For example, method step 7950 can include activating a visual indicator. For example, method step 7950 can include activating an audio indicator. For example, method step 7950 can include activating a vibratory indicator.

As depicted in FIG. 79, method step 7960 includes accepting second data from the camera unit associated with the individual, the second data obtained after the activation of the at least one indicator. Method step 7960 can include one or more additional steps. For example, method step 7960 can include accepting second data from at least one camera unit, the second data including at least one time value. For example, method step 7960 can include accepting data including visual data, non-visual data, and at least one time value.

As shown in FIG. 79, method step 7970 includes analyzing the accepted second data for at least one attribute relating to the medication event. Method step 7970 can include one or more additional steps. For example, method step 7970 can include analyzing the accepted second data for the at least one attribute relating to a medication event. For example, method step 7970 can include analyzing the accepted second data for at least one visual attribute. For example, method step 7970 can include analyzing the accepted second data for at least one non-visual attribute.

As illustrated in FIG. 79, method step 7980 includes comparing the accepted second data with the provided set of medication intervention parameters for the individual.

Method step 7980 can include one or more additional steps. For example, method step 7980 can include comparing both visual data and non-visual data.

As depicted in FIG. 79, method step 7990 includes determining if the accepted second data is within the provided set of medication intervention parameters. Method step 7990 can include one or more additional steps. For example, method step 7990 can include determining that the accepted second data either is within the provided set of medication intervention parameters or is not within the provided set of medication intervention parameters.

As shown in FIG. 79, method step 7995 includes activating the at least one indicator in response to the second determination. Method step 7995 can include one or more additional steps. For example, method step 7995 can include activating at least one visual indicator. For example, method step 7995 can include activating at least one audio indicator. For example, method step 7995 can include activating at least one vibratory indicator.

In some embodiments, the flowchart of a method 7900 for monitoring medication events shown in FIG. 79 includes one or more additional aspects. For example, the method can include: presenting at least one attribute of the individual; and analyzing the accepted first data for the at least one attribute of the individual. For example, the method can include: presenting at least one attribute of the individual; and analyzing the accepted second data for the at least one attribute of the individual. For example, the method can include: saving the accepted first data in a memory. For example, the method can include: saving the accepted second data in a memory. For example, the method can include: processing the at least one accepted first data; processing the at least one accepted second data; integrating the processed at least one accepted first data and the processed at least one accepted second data into a medication record; and saving the medication record in a memory. For example, the method can include: processing the determination if the accepted first data is within the provided set of medication intervention parameters into a first result; and transmitting the first result. For example, the method can include: processing the determination if the accepted second data is within the provided set of medication intervention parameters into a second result; and transmitting the second result. For example, the method can include: accepting third data from the camera unit associated with the individual, the third data obtained after the activation of the at least one indicator in response to the second determination; analyzing the accepted third data for the at least one attribute relating to the medication event; comparing the accepted third data with the provided set of medication intervention parameters for the individual; determining if the accepted third data is within the provided set of medication intervention parameters; and activating the at least one indicator in response to the third determination.

FIG. 80 illustrates diagram of aspects of a system for monitoring medication events relating to an individual. The system can be a computer system such as depicted in FIG. 1 and described herein. The system 8000 depicted in FIG. 80 includes electrical circuitry. The circuitry of the system 8000 is configured to carry out a series of logical processes. As illustrated in FIG. 80, a system 8000 for monitoring medication events relating to an individual includes one or more circuitry components 8010, 8020, 8030, 8040, 8050, 8060, 8070, 8080, 8090, 8095. The circuitry is configured to carry out specific processes.

The system 8000 includes circuitry 8010 for providing a set of attributes for an individual, the set of attributes identifiable in camera unit data. The system 8000 includes circuitry 8020 for providing a set of medication condition parameters for the individual, the set of medication condition parameters identifiable in the camera unit data. The system 8000 includes circuitry 8030 for accepting first data from at least one camera unit. The system 8000 includes circuitry 8040 for comparing the accepted first data with the provided set of attributes for the individual and with the provided set of medication condition parameters for the individual. The system 8000 includes circuitry 8050 for determining, from the comparison, if the accepted first data includes attributes of the individual and meets the medication condition parameters. The system 8000 includes circuitry 8060 for initiating a first medication intervention event, dependent on the determination from the comparison. The system 8000 includes circuitry 8070 for accepting second data from the at least one camera unit. The system 8000 includes circuitry 8080 for providing a set of parameters for the first medication intervention event, the set of first medication intervention parameters identifiable in the camera unit data. The system 8000 includes circuitry 8085 for comparing the accepted second data with the provided set of attributes for the individual and with the provided set of parameters for the first medication intervention event. The system 8000 includes circuitry 8090 for determining, from the comparison, if the accepted second data includes attributes of the individual and meets the parameters for the first medication intervention event. The system 8000 includes circuitry 8095 for activating at least one indicator in response to the second determination.

FIG. 81 illustrates that, in some embodiments, the system 8000 including circuitry 8010 can include one or more of circuitry 8100, 8110, 8120, 8130, 8140. The system 8000 includes circuitry 8010 for providing a set of attributes for an individual, the set of attributes identifiable in camera unit data. In some embodiments, circuitry 8010 includes circuitry 8100 for: providing visual attributes; and circuitry for providing non-visual attributes. For example, the circuitry can provide attributes from camera data as well as provide attributes from an attached microphone. In some embodiments, circuitry 8010 includes circuitry 8110 for providing a set of attributes identifiable in the camera unit data originating with a mobile device. For example, the circuitry can provide a set of attributes identifiable in the camera unit data originating from at least one smartphone, PDA, tablet computer, or laptop. In some embodiments, circuitry 8010 includes circuitry 8120 for providing a set of attributes identifiable in the camera unit data originating with a fixed position camera unit. For example, the circuitry can provide a set of attributes identifiable in the camera unit data originating with a fixed position camera unit configured to be attached to a wall. In some embodiments, circuitry 8010 includes circuitry 8130 for providing a set of attributes identifiable in the camera unit data including at least two visual images. For example, the circuitry can provide a set of attributes identifiable in the camera unit data including at least two visual images taken from the same camera unit at different times. For example, the circuitry can provide a set of attributes identifiable in the camera unit data including at least two visual images taken from two different camera units. In some embodiments, circuitry 8010 includes circuitry 8140 for providing a set of attributes identifiable in the camera unit data including video data. For example, the circuitry can provide a set of attributes identifiable in the camera unit data including video data taken with the camera unit during the duration of an expected medication event.

FIG. 82 shows that, in some embodiments, the system 8000 including circuitry 8010 can include one or more of circuitry 8200, 8210, 8220, 8230, 8240. The system 8000 includes circuitry 8010 for providing a set of attributes for an individual, the set of attributes identifiable in camera unit data. In some embodiments, circuitry 8010 includes circuitry 8200 for providing a set of attributes identifiable in the camera unit data including near-infrared (IR) data. For example, the circuitry can provide attributes from camera data taken in the near-IR spectrum. In some embodiments, circuitry 8010 includes circuitry 8210 for providing a set of attributes identifiable in the camera unit data including thermal data. For example, the circuitry can provide a set of attributes identifiable in the camera unit data originating from a camera unit that includes a temperature monitor device. In some embodiments, circuitry 8010 includes circuitry 8220 for providing a set of attributes identifiable in the camera unit data including audio data. For example, the circuitry can provide a set of attributes identifiable in the camera unit data originating with a microphone attached to the camera unit. In some embodiments, circuitry 8010 includes circuitry 8230 for providing a set of attributes identifiable in the camera unit data including micropower impulse radar (MIR) data. For example, the camera unit can include a MIR device. In some embodiments, circuitry 8010 includes circuitry 8240 for providing a set of attributes specific to the individual. For example, the circuitry can provide a set of attributes identifiable in the camera unit data including aspects of the facial features of the individual.

FIG. 83 shows that, in some embodiments, the system 8000 can include additional features. The system 8000 includes circuitry 8020 for providing a set of medication condition parameters for the individual, the set of medication condition parameters identifiable in the camera unit data. FIG. 83 shows that in some embodiments, circuitry 8020 can include one or more of circuitry 8300, 8310, 8320, 8330, 8340. Circuitry 8300 includes circuitry for providing visual parameters and providing non-visual parameters. For example, the circuitry can provide parameter for data originating from the optic features of a camera unit, as well as parameters for data originating from a microphone attached to the camera unit. Circuitry 8310 includes circuitry for providing a set of parameters identifiable in the camera unit data originating with a mobile device. For example, the data can originate with a camera unit integral to a PDA, laptop, or tablet computing device. Circuitry 8320 includes circuitry for providing a set of parameters identifiable in the camera unit data originating with a fixed position camera unit. For example, the data can originate with a camera unit integral to a camera unit affixed to a post or beam of a building. Circuitry 8330 includes circuitry for providing a set of parameters including at least two visual parameters. For example, the visual parameters can include brightness parameters as well as pixel size parameters. Circuitry 8340 includes circuitry for providing a set of parameters identifiable in video data. For example, the data can originate with a camera unit including video capabilities.

FIG. 84 depicts that, in some embodiments, the system 8000 can include additional features. The system 8000 includes circuitry 8020 for providing a set of medication condition parameters for the individual, the set of medication condition parameters identifiable in the camera unit data. FIG. 84 shows that in some embodiments, circuitry 8020 can include one or more of circuitry 8400, 8410, 8420, 8430, 8440. Circuitry 8400 includes circuitry for a set of parameters including audio parameters. For example, the circuitry can provide parameters for data originating from a microphone attached to the camera unit, such as pitch, decibel level, or tone. Circuitry 8410 includes circuitry for providing a set of parameters including thermal parameters. For example, the data can originate with a camera unit including a thermal reader, and the parameters can include high and low temperature readings. Circuitry 8420 includes circuitry for providing a set of parameters including near-infrared (IR) parameters. For example, the data can originate with a camera unit including near-IR detection capabilities. Circuitry 8430 includes circuitry for providing a set of parameters including radio frequency (RF) parameters. For example, the visual parameters can include RFID code parameters. Circuitry 8440 includes circuitry for providing a set of parameters including micropower impulse radar (MIR) parameters. For example, the data can originate with a camera unit integrated with a MIR device.

FIG. 85 shows that, in some embodiments, the system 8000 can include additional features. The system 8000 includes circuitry 8020 for providing a set of medication condition parameters for the individual, the set of medication condition parameters identifiable in the camera unit data. FIG. 85 illustrates that in some embodiments, circuitry 8020 can include circuitry 8500. Circuitry 8500 includes circuitry for providing a set of parameters specific to the individual. For example, the circuitry 8500 can include providing a set of parameters such as eye color, height, facial shape, and similar parameters specific to the individual.

FIG. 85 also illustrates that, in some embodiments, circuitry 8030 can include one or more of circuitry 8510, 8520, 8530, 8540, 8550, 8560. Circuitry 8030 includes circuitry for accepting first data from at least one camera unit. Circuitry 8510 includes circuitry for accepting both visual and non-visual data. For example, the circuitry can be configured to accept visual data obtained by a camera unit and audio data from an attached microphone. Circuitry 8520 includes circuitry for accepting video data. Circuitry 8530 includes circuitry for accepting audio data. Circuitry 8540 includes circuitry for accepting thermal data. Circuitry 8550 includes circuitry for accepting near-infrared (IR) data. Circuitry 8550 includes circuitry for accepting radio frequency (RF) data.

FIG. 86 depicts that, in some embodiments, the system 8000 can include additional features. The system 8000 includes circuitry 8030 for accepting first data from at least one camera unit. FIG. 86 illustrates that in some embodiments, circuitry 8030 can include one or more of circuitry 8600, 8610, 8620, 8630. Circuitry 8600 includes circuitry for accepting micropower impulse radar (MIR) data. Circuitry 8610 includes circuitry for accepting data from a camera unit integral to a mobile device. Circuitry 8620 includes circuitry for accepting data from the camera unit integral to a fixed-position device. Circuitry 8630 includes circuitry for accepting data from a plurality of camera units. For example, the circuitry can accept data from a plurality of camera units integrated into one or more mobile devices, or a plurality of fixed-position camera units, or a combination thereof.

FIG. 86 also shows that, in some embodiments, circuitry 8040 can include circuitry 8640. Circuitry 8040 includes circuitry for comparing the accepted first data with the provided set of attributes for the individual and with the provided set of medication condition parameters for the individual. Circuitry 8640 includes circuitry for comparing a subset of the accepted first data with the provided set of medication condition parameters for the individual and with the provided set of medication condition parameters for the individual.

FIG. 87 shows additional features of the system 8000 for monitoring medication events. FIG. 87 illustrates that circuitry 8040 can include circuitry 8700. Circuitry 8700 includes circuitry for comparing visual and non-visual components of the accepted first data with the provided set of medication condition parameters for the individual and with the provided set of medication condition parameters for the individual. FIG. 87 also illustrates that, in some embodiments, circuitry 8050 can include circuitry 8710. Circuitry 8050 includes circuitry for determining, from the comparison, if the accepted first data includes attributes of the individual and meets the medication condition parameters. Circuitry 8710 includes circuitry for determining, from the comparison, if the accepted first data meets both visual and non-visual aspects of the medication condition parameters.

FIG. 88 depicts additional features of the system 8000 for monitoring medication events. FIG. 88 shows that circuitry 8060 can, in some embodiments, include one or more of circuitry 8800, 8810. Circuitry 8060 includes circuitry for initiating the first medication intervention event, dependent on the determination from the comparison. Circuitry 8800 includes circuitry for activating at least one indicator. For example, the circuitry can function to activate at least one indicator attached to the computer system (i.e. item 120 in FIG. 1). Circuitry 8810 includes circuitry for activating at least one alarm. For example, the circuitry can function to activate at least one alarm attached to the computer system (i.e. item 120 in FIG. 1).

FIG. 88 also illustrates that, in some embodiments, circuitry 8070 can include on or more of circuitry 8820, 8830, 8840. Circuitry 8070 includes the circuitry for accepting the second data from the at least one camera unit. Circuitry 8820 includes circuitry for accepting second data including both visual and non-visual aspects. Circuitry 8830 includes circuitry for accepting second data including at least one time value. Circuitry 8840 includes circuitry for accepting data including a personal identifier of the individual. For example, the circuitry can be configured to accept data including an RFID code identifying the individual, such as from an RF signal reflected from an ID band. For example, the circuitry can be configured to accept data including a personal identifier such as a name or ID number input into the system, such as from a keyboard integrated into a monitoring device (e.g. item 160 in FIG. 1).

FIG. 89 shows that, in some embodiments, circuitry 8070 includes circuitry 8900. Circuitry 8070 includes the circuitry for accepting the second data from the at least one camera unit. Circuitry 8900 includes accepting data from a plurality of camera units. FIG. 89 also shows that, in some embodiments, circuitry 8080 includes one or more of circuitry 8910, 8920, 8930. Circuitry 8080 includes providing the set of parameters for the first medication intervention event, the set of medication intervention parameters identifiable in the camera unit data. Circuitry 8910 includes circuitry for providing a set of parameters including minimum values. For example, the minimum values can include minimum brightness values or numbers of pixels. Circuitry 8920 includes circuitry for providing a set of both visual and non-visual parameters. Circuitry 8930 includes circuitry for providing a set of parameters including a range of values. For example, the circuitry can include a range of acceptable brightness values or a range of pixel levels in the data.

FIG. 90 shows that, in some embodiments, circuitry 8090 includes one or more of circuitry 9000, 9010. Circuitry 8090 includes circuitry for determining, from the comparison, if the accepted second data includes attributes of the individual and meets the parameters for the first medication intervention event. Circuitry 9000 includes circuitry for comparing the accepted data including both visual and non-visual data with the provided set of attributes for the individual and with the provided set of medication intervention parameters for the individual. Circuitry 9010 includes circuitry for determining, from the comparison, if the accepted second data meets both visual and non-visual aspects of the medication condition parameters. FIG. 90 also shows that, in some embodiments, circuitry 9095 includes circuitry 9020. Circuitry 9095 includes circuitry for activating the at least one indicator in response to the second determination. Circuitry 9020 includes circuitry for activating at least one visual indicator. For example, circuitry can be configured to activate at least one visual indicator on a display unit attached to a main computing unit within the computer system (e.g. item 125 in FIG. 1).

FIG. 91 shows that, in some embodiments, the system 8000 for monitoring medication events includes additional components in addition to circuitry 8010, 8020, 8030, 8040, 8050, 8060, 8070, 8080, 8090, 8095. FIG. 91 illustrates that the system can include one or more of circuitry 9100, 9110, 9120, 9230. Circuitry 9100 includes circuitry for saving the first determination in a memory. Circuitry 9110 includes circuitry for saving the second determination in a memory. For example, the system can save the first or second determination in a memory within the hard drive of a main computing unit (e.g. item 125 in FIG. 1). Circuitry 9120 includes circuitry for saving the accepted first data in a memory. Circuitry 9130 includes circuitry for saving the accepted second data in a memory. For example, the system can save the accepted first or second data in a memory within the hard drive of a main computing unit (e.g. item 125 in FIG. 1).

FIG. 92 depicts that, in some embodiments, the system 8000 for monitoring medication events includes additional components in addition to circuitry 8010, 8020, 8030, 8040, 8050, 8060, 8070, 8080, 8090, 8095. FIG. 92 shows that the system can include one or more of circuitry 9200, 9210. Circuitry 9200 includes: circuitry for processing the at least one accepted first data; circuitry for processing the at least one accepted second data; circuitry for integrating the processed at least one accepted first data and the processed at least one accepted second data into a medication record; and circuitry for saving the medication record in a memory. Circuitry 9210 includes: circuitry for processing the if the accepted first data includes attributes of the individual and meets the medication condition parameters into a first result; and circuitry for transmitting the first result. For example, the first result can be transmitted to a secondary computing unit (e.g. items 130, 135 in FIG. 1).

FIG. 93 illustrates that, in some embodiments, the system 8000 for monitoring medication events includes additional components in addition to circuitry 8010, 8020, 8030, 8040, 8050, 8060, 8070, 8080, 8090, 8095. FIG. 93 depicts that the system can include one or more of circuitry 9300, 9310. Circuitry 9300 includes circuitry for indicating, to at least one system user, the initiating a first medication intervention event. Circuitry 9310 includes: circuitry for indicating, to at least one system user, the determining, from the comparison, if the accepted second data includes attributes of the individual and meets the parameters for the first medication intervention event.

FIG. 94 depicts that, in some embodiments, the system 8000 for monitoring medication events includes additional components in addition to circuitry 8010, 8020, 8030, 8040, 8050, 8060, 8070, 8080, 8090, 8095. FIG. 94 depicts that the system can include circuitry 9400. Circuitry 9400 includes: circuitry for accepting third data from the at least one camera unit; circuitry for providing a set of parameters for a second medication intervention event, the set of second medication intervention parameters identifiable in camera unit data; circuitry for comparing the accepted third data with the provided set of attributes for the individual and with the provided set of parameters for the second medication intervention event; circuitry for determining, from the comparison, if the accepted third data includes attributes of the individual and meets the parameters for the second medication intervention event; and circuitry for activating at least one indicator in response to the third determination.

FIG. 95 illustrates aspects of a computer system 120 including at least one main computing unit 125. Although a single main computing unit 125 is illustrated in FIG. 95, in some embodiments there may be a plurality of main computing units 125. A main computing unit 125 includes computer-readable storage medium including executable instructions for monitoring medication events 9500. The computer-readable storage medium including executable instructions for monitoring medication events relating to an individual 9500 includes instructions 9510, 9520, 9530, 9540, 9550, 9560, 9570, 9580, 9585, 9590, 9595. Instructions 9510 include instructions for providing a set of attributes for an individual, the set of attributes identifiable in camera unit data. Instructions 9520 include instructions for providing a set of medication condition parameters for the individual, the set of medication condition parameters identifiable in camera unit data. Instructions 9530 include instructions for accepting first data from at least one camera unit. Instructions 9540 include instructions for comparing the accepted first data with the provided set of attributes for the individual and with the provided set of medication condition parameters for the individual. Instructions 9550 include instructions for determining, from the comparison, if the accepted first data includes attributes of the individual and meets the medication condition parameters. Instructions 9560 include instructions for initiating a first medication intervention event, dependent on the determination from the comparison. Instructions 9570 include instructions for accepting second data from the at least one camera unit. Instructions 9580 include instructions for providing a set of parameters for the first medication intervention event, the set of first medication intervention parameters identifiable in camera unit data. Instructions 9585 include instructions for comparing the accepted second data with the provided set of attributes for the individual and with the provided set of parameters for the first medication intervention event. Instructions 9590 include instructions for determining, from the comparison, if the accepted second data includes attributes of the individual and meets the parameters for the first medication intervention event. Instructions 9595 include instructions for activating at least one indicator in response to the second determination.

As shown in FIG. 95, instructions 9510 include instructions for providing a set of attributes for an individual, the set of attributes identifiable in camera unit data. In some embodiments, instructions 9510 can include one or more additional instructions. In some embodiments, instructions 9510 include: instructions for providing visual attributes; and instructions for providing non-visual attributes. In some embodiments, instructions 9510 include instructions for providing a set of attributes identifiable in camera unit data originating with a mobile device. In some embodiments, instructions 9510 include instructions for providing a set of attributes identifiable in camera unit data originating with a fixed position camera unit. In some embodiments, instructions 9510 include instructions for providing a set of attributes identifiable in camera unit data including at least two visual images. In some embodiments, instructions 9510 include instructions for providing a set of attributes identifiable in camera unit data including video data. In some embodiments, instructions 9510 include instructions for providing a set of attributes identifiable in camera unit data including near-infrared (IR) data. In some embodiments, instructions 9510 include instructions for providing a set of attributes identifiable in camera unit data including thermal data. In some embodiments, instructions 9510 include instructions for providing a set of attributes identifiable in camera unit data including audio data. In some embodiments, instructions 9510 include instructions for providing a set of attributes identifiable in camera unit data including micropower impulse radar (MIR) data. In some embodiments, instructions 9510 include instructions for providing a set of attributes specific to the individual.

As depicted in FIG. 95, instructions 9520 include instructions for providing the set of medication condition parameters for the individual, the set of medication condition parameters identifiable in the camera unit data. In some embodiments, instructions 9520 can include one or more additional instructions. In some embodiments, instructions 9520 include instructions for providing visual parameters and providing non-visual parameters. In some embodiments, instructions 9520 include instructions for providing a set of parameters identifiable in camera unit data originating with a mobile device. In some embodiments, instructions 9520 include instructions for providing a set of parameters identifiable in camera unit data originating with a fixed position camera unit. In some embodiments, instructions 9520 include instructions for providing a set of parameters including at least two visual parameters. In some embodiments, instructions 9520 include instructions for providing a set of parameters identifiable in video data. In some embodiments, instructions 9520 include instructions for providing a set of parameters including audio parameters. In some embodiments, instructions 9520 include instructions for providing a set of parameters including thermal parameters. In some embodiments, instructions 9520 include instructions for providing a set of parameters including near-infrared (IR) parameters. In some embodiments, instructions 9520 include instructions for providing a set of parameters including radio frequency (RF) parameters. In some embodiments, instructions 9520 include instructions for providing a set of parameters including micropower impulse radar (MIR) parameters. In some embodiments, instructions 9520 include instructions for providing a set of parameters specific to the individual.

As shown in FIG. 95, instructions 9530 include instructions for accepting the first data from the at least one camera unit. In some embodiments, instructions 9530 can include one or more additional instructions. In some embodiments, instructions 9530 include instructions for accepting both visual and non-visual data. In some embodiments, instructions 9530 include instructions for accepting video data. In some embodiments, instructions 9530 include instructions for accepting audio data. In some embodiments, instructions 9530 include instructions for accepting thermal data. In some embodiments, instructions 9530 include instructions for accepting near-infrared (IR) data. In some embodiments, instructions 9530 include instructions for accepting radio frequency (RF) data. In some embodiments, instructions 9530 include instructions for accepting micropower impulse radar (MIR) data. In some embodiments, instructions 9530 include instructions for accepting data from a camera unit integral to a mobile device. In some embodiments, instructions 9530 include instructions for accepting data from a camera unit integral to a fixed-position device. In some embodiments, instructions 9530 include instructions for accepting data from a plurality of camera units.

As shown in FIG. 95, instructions 9540 include instructions for comparing the accepted first data with the provided set of attributes for the individual and with the provided set of medication condition parameters for the individual. In some embodiments, instructions 9540 can include one or more additional instructions. In some embodiments, instructions 9540 include instructions for comparing a subset of the accepted first data with the provided set of medication condition parameters for the individual and with the provided set of medication condition parameters for the individual. In some embodiments, instructions 9540 include instructions for comparing visual and non-visual components of the accepted first data with the provided set of medication condition parameters for the individual and with the provided set of medication condition parameters for the individual.

As depicted in FIG. 95, instructions 9550 include instructions for determining, from the comparison, if the accepted first data includes attributes of the individual and meets the medication condition parameters. In some embodiments, instructions 9550 can include one or more additional instructions. In some embodiments, instructions 9550 include instructions for determining, from the comparison, if the accepted first data meets both visual and non-visual aspects of the medication condition parameters.

As shown in FIG. 95, instructions 9560 include instructions for initiating the first medication intervention event, dependent on the determination from the comparison. In some embodiments, instructions 9560 can include one or more additional instructions. In some embodiments, instructions 9560 include instructions for activating at least one indicator. In some embodiments, instructions 9560 include instructions for activating at least one alarm. For example, the instructions can cause the system to activate at least one indicator and/or at least one alarm attached to a main computing unit (e.g. item 120 in FIG. 95).

As illustrated in FIG. 95, instructions 9570 include instructions for accepting the second data from the at least one camera unit. In some embodiments, instructions 9570 can include one or more additional instructions. In some embodiments, instructions 9570 include instructions for accepting second data including both visual and non-visual aspects. In some embodiments, instructions 9570 include instructions for accepting second data including at least one time value. In some embodiments, instructions 9570 include instructions for accepting data including a personal identifier of the individual. In some embodiments, instructions 9570 include instructions for accepting data from a plurality of camera units. For example, the system can include instructions for accepting data from a plurality of monitoring devices (e.g. item 110 in FIG. 1) that are fixed camera units affixed to the walls of a room for the medication event (e.g. a therapy room).

As shown in FIG. 95, instructions 9580 include instructions providing the set of parameters for the first medication intervention event, the set of medication intervention parameters identifiable in the camera unit data. In some embodiments, instructions 9580 can include one or more additional instructions. In some embodiments, instructions 9580 include instructions for providing a set of parameters including minimum values. In some embodiments, instructions 9580 include instructions for providing a set of both visual and non-visual parameters. In some embodiments, instructions 9580 include instructions for providing a set of parameters including a range of values.

As depicted in FIG. 95, instructions 9590 include instructions for determining, from the comparison, if the accepted second data includes attributes of the individual and meets the parameters for the first medication intervention event. In some embodiments, instructions 9590 can include one or more additional instructions. In some embodiments, instructions 9590 include instructions for comparing accepted data including both visual and non-visual data with the provided set of attributes for the individual and with the provided set of medication intervention parameters for the individual. In some embodiments, instructions 9590 include instructions for determining, from the comparison, if the accepted second data meets both visual and non-visual aspects of the medication condition parameters.

As illustrated in FIG. 95, instructions 9595 include instructions for activating the at least one indicator in response to the second determination. In some embodiments, instructions 9595 can include one or more additional instructions. In some embodiments, instructions 9595 include instructions for activating at least one visual indicator.

In some embodiments, the computer-readable storage medium including executable instructions for monitoring medication events 9500 includes one or more sets of additional instructions. For example, the computer-readable storage medium including executable instructions for monitoring medication events 9500 can include instructions for saving the first determination in a memory. For example, the computer-readable storage medium including executable instructions for monitoring medication events 9500 can include instructions for saving the second determination in a memory. For example, the computer-readable storage medium including executable instructions for monitoring medication events 9500 can include instructions for saving the accepted first data in a memory. For example, the computer-readable storage medium including executable instructions for monitoring medication events 9500 can include instructions for saving the accepted second data in a memory. For example, the computer-readable storage medium including executable instructions for monitoring medication events 9500 can include: instructions for processing the at least one accepted first data; instructions for processing the at least one accepted second data; instructions for integrating the processed at least one accepted first data and the processed at least one accepted second data into a medication record; and instructions for saving the medication record in a memory. For example, the computer system (e.g. item 120 in FIG. 95) can include memory units, such as memory within a main computing unit (e.g. item 125 in FIG. 95) or additional computer memory storage devices within the computer system.

In some embodiments, the computer-readable storage medium including executable instructions for monitoring medication events 9500 includes one or more sets of additional instructions. For example, the computer-readable storage medium including executable instructions for monitoring medication events 9500 can include: instructions for processing the if the accepted first data includes attributes of the individual and meets the medication condition parameters into a first result; and instructions for transmitting the first result. For example, the first result can be transmitted within the computer system (e.g. item 120 in FIG. 95) from a transmitter attached to a main computing unit (e.g. item 125 in FIG. 95) to a secondary computing unit (e.g. items 140, 145 in FIG. 1).

In some embodiments, the computer-readable storage medium including executable instructions for monitoring medication events 9500 includes one or more sets of additional instructions. For example, the computer-readable storage medium including executable instructions for monitoring medication events 9500 can include instructions for indicating, to at least one system user, the initiating a first medication intervention event. For example, the computer-readable storage medium including executable instructions for monitoring medication events 9500 can include instructions for indicating, to at least one system user, the determining, from the comparison, if the accepted second data includes attributes of the individual and meets the parameters for the first medication intervention event. In some embodiments, the computer-readable storage medium including executable instructions for monitoring medication events 9500 includes one or more sets of additional instructions. For example, the computer-readable storage medium including executable instructions for monitoring medication events 9500 can include: instructions for accepting third data from the at least one camera unit; instructions for providing a set of parameters for a second medication intervention event, the set of second medication intervention parameters identifiable in camera unit data; instructions for comparing the accepted third data with the provided set of attributes for the individual and with the provided set of parameters for the second medication intervention event; instructions for determining, from the comparison, if the accepted third data includes attributes of the individual and meets the parameters for the second medication intervention event; and instructions for activating at least one indicator in response to the third determination. For example, a main computing unit (e.g. item 125 in FIG. 95) can include a monitor device, which can be configured to respond to instructions of the system for making an indication.

FIG. 96 illustrates a flowchart of a method 9600 for monitoring medication events. These method steps can be carried out, for example, by a computer system (e.g. item 120 in FIG. 1). FIG. 96 shows that the method includes a series of steps, 9610, 9620, 9630, 9640, 9650, 9660, 9670, 9680, 9685, 9690, 9695. Method step 9610 includes providing a set of attributes for an individual, the set of attributes identifiable in camera unit data. Method step 9620 includes providing a set of medication condition parameters for the individual, the set of medication condition parameters identifiable in camera unit data. Method step 9630 includes accepting first data from at least one camera unit. Method step 9640 includes comparing the accepted first data with the provided set of attributes for the individual and with the provided set of medication condition parameters for the individual. Method step 9650 includes determining, from the comparison, if the accepted first data includes attributes of the individual and meets the medication condition parameters. Method step 9660 includes initiating a first medication intervention event, dependent on the determination from the comparison. Method step 9670 includes accepting second data from the at least one camera unit. Method step 9680 includes providing a set of parameters for the first medication intervention event, the set of first medication intervention parameters identifiable in camera unit data. Method step 9685 includes comparing the accepted second data with the provided set of attributes for the individual and with the provided set of parameters for the first medication intervention event. Method step 9690 includes determining, from the comparison, if the accepted second data includes attributes of the individual and meets the parameters for the first medication intervention event. Method step 9695 includes activating at least one indicator in response to the second determination.

In some embodiments, the flowchart of a method 9600 for monitoring medication events illustrated in FIG. 96 includes additional aspects. As illustrated in FIG. 96, method step 9610 includes providing a set of attributes for an individual, the set of attributes identifiable in camera unit data. Method step 9610 can include one or more additional steps. For example, method step 9610 can include: providing visual attributes; and providing non-visual attributes. For example, method step 9610 can include providing a set of attributes identifiable in camera unit data originating with a mobile device. For example, method step 9610 can include providing at set of attributes identifiable in camera unit data originating with a fixed position camera unit. For example, method step 9610 can include providing a set of attributes identifiable in camera unit data including at least two visual images. For example, method step 9610 can include providing a set of attributes identifiable in camera unit data including video data. For example, method step 9610 can include providing a set of attributes identifiable in camera unit data including near-infrared (IR) data. For example, method step 9610 can include providing a set of attributes identifiable in camera unit data including thermal data. For example, method step 9610 can include providing a set of attributes identifiable in camera unit data including audio data. For example, method step 9610 can include providing a set of attributes identifiable in camera unit data including micropower impulse radar (MIR) data. For example, method step 9610 can include providing a set of attributes specific to the individual.

As shown in FIG. 96, method step 9620 includes providing a set of medication condition parameters for the individual, the set of medication condition parameters identifiable in camera unit data. Method step 9620 can include one or more additional steps. For example, method step 9620 can include providing visual parameters and providing non-visual parameters. For example, method step 9620 can include providing a set of parameters identifiable in camera unit data originating with a mobile device. For example, method step 9620 can include providing a set of parameters identifiable in camera unit data originating with a fixed position camera unit. For example, method step 9620 can include providing a set of parameters including at least two visual parameters. For example, method step 9620 can include providing a set of parameters identifiable in video data. For example, method step 9620 can include providing a set of parameters including audio parameters. For example, method step 9620 can include providing a set of parameters including thermal parameters. For example, method step 9620 can include providing a set of parameters including near-infrared (IR) parameters. For example, method step 9620 can include providing a set of parameters including radio frequency (RF) parameters. For example, method step 9620 can include providing a set of parameters including micropower impulse radar (MIR) parameters. For example, method step 9620 can include providing a set of parameters specific to the individual.

As illustrated in FIG. 96, method step 9630 includes accepting first data from at least one camera unit. Method step 9630 can include one or more additional steps. For example, method step 9630 can include accepting both visual and non-visual data. For example, method step 9630 can include accepting video data. For example, method step 9630 can include accepting audio data. For example, method step 9630 can include accepting thermal data. For example, method step 9630 can include accepting near-infrared (IR) data. For example, method step 9630 can include accepting radio frequency (RF) data. For example, method step 9630 can include accepting micropower impulse radar (MIR) data. For example, method step 9630 can include accepting data from a camera unit integral to a mobile device. For example, method step 9630 can include accepting data from a camera unit integral to a fixed-position device. For example, method step 9630 can include accepting data from a plurality of camera units.

As depicted in FIG. 96, method step 9640 includes comparing the accepted first data with the provided set of attributes for the individual and with the provided set of medication condition parameters for the individual. Method step 9640 can include one or more additional steps. For example, method step 9640 can include comparing a subset of the accepted first data with the provided set of medication condition parameters for the individual and with the provided set of medication condition parameters for the individual.

Method step 9640 can include comparing visual and non-visual components of the accepted first data with the provided set of medication condition parameters for the individual and with the provided set of medication condition parameters for the individual.

As depicted in FIG. 96, method step 9650 includes determining, from the comparison, if the accepted first data includes attributes of the individual and meets the medication condition parameters. Method step 9650 can include one or more additional steps. For example, method step 9650 can include determining, from the comparison, if the accepted first data meets both visual and non-visual aspects of the medication condition parameters.

As shown in FIG. 96, method step 9660 includes initiating a first medication intervention event, dependent on the determination from the comparison. Method step 9660 can include one or more additional steps. For example, method step 9660 can include activating at least one indicator. For example, method step 9660 can include activating at least one alarm.

As depicted in FIG. 96, method step 9670 includes accepting second data from the at least one camera unit. Method step 9670 can include one or more additional steps. For example, method step 9670 can include accepting second data including both visual and non-visual aspects. For example, method step 9670 can include accepting second data including at least one time value. For example, method step 9670 can include accepting data including a personal identifier of the individual. For example, method step 9670 can include accepting data from a plurality of camera units.

As shown in FIG. 96, method step 9680 includes providing a set of parameters for the first medication intervention event, the set of first medication intervention parameters identifiable in camera unit data. Method step 9680 can include one or more additional steps. For example, method step 9680 can include providing a set of parameters including minimum values. For example, method step 9680 can include providing a set of both visual and non-visual parameters. For example, method step 9680 can include providing a set of parameters including a range of values.

As illustrated in FIG. 96, method step 9690 includes determining, from the comparison, if the accepted second data includes attributes of the individual and meets the parameters for the first medication intervention event. Method step 9690 can include one or more additional steps. For example, method step 9690 can include comparing accepted data including both visual and non-visual data with the provided set of attributes for the individual and with the provided set of medication intervention parameters for the individual. For example, method step 9690 can include determining, from the comparison, if the accepted second data meets both visual and non-visual aspects of the medication condition parameters.

As shown in FIG. 96, method step 9695 includes activating at least one indicator in response to the second determination. Method step 9695 can include one or more additional steps. For example, method step 9695 can include activating at least one visual indicator.

The method flowchart illustrated in FIG. 96 can also include additional steps. For example, the method 9600 can include saving the first determination in a memory. For example, the method 9600 can include saving the second determination in a memory. For example, the method 9600 can include saving the accepted first data in a memory. For example, the method 9600 can include saving the accepted second data in a memory. For example, the method 9600 can include: processing the at least one accepted first data; processing the at least one accepted second data; integrating the processed at least one accepted first data and the processed at least one accepted second data into a medication record; and saving the medication record in a memory. A memory can, for example, be a computer memory integrated with the computer system (e.g. item 120 in FIG. 1).

The method flowchart depicted in FIG. 96 can also include additional steps. For example, the method 9600 can include: processing the if the accepted first data includes attributes of the individual and meets the medication condition parameters into a first result; and transmitting the first result. A transmitter can, for example, be integrated into the computer system (e.g. item 120 in FIG. 1) and transmit a result from the main computing unit (e.g. item 125 in FIG. 1) to one or more secondary computing units (e.g. items 130, 135 in FIG. 1).

The method flowchart shown in FIG. 96 can also include additional steps. For example, the method 9600 can include indicating, to at least one system user, the initiating a first medication intervention event. For example, the method 9600 can include indicating, to at least one system user, the determining, from the comparison, if the accepted second data includes attributes of the individual and meets the parameters for the first medication intervention event. For example, the method 9600 can include accepting third data from the at least one camera unit; providing a set of parameters for a second medication intervention event, the set of second medication intervention parameters identifiable in camera unit data; comparing the accepted third data with the provided set of attributes for the individual and with the provided set of parameters for the second medication intervention event; determining, from the comparison, if the accepted third data includes attributes of the individual and meets the parameters for the second medication intervention event; and activating at least one indicator in response to the third determination. An indicator can be attached, for example, to the main computing unit (e.g. item 125 in FIG. 1), such asn indicator light or a computer display.

Figure 97:
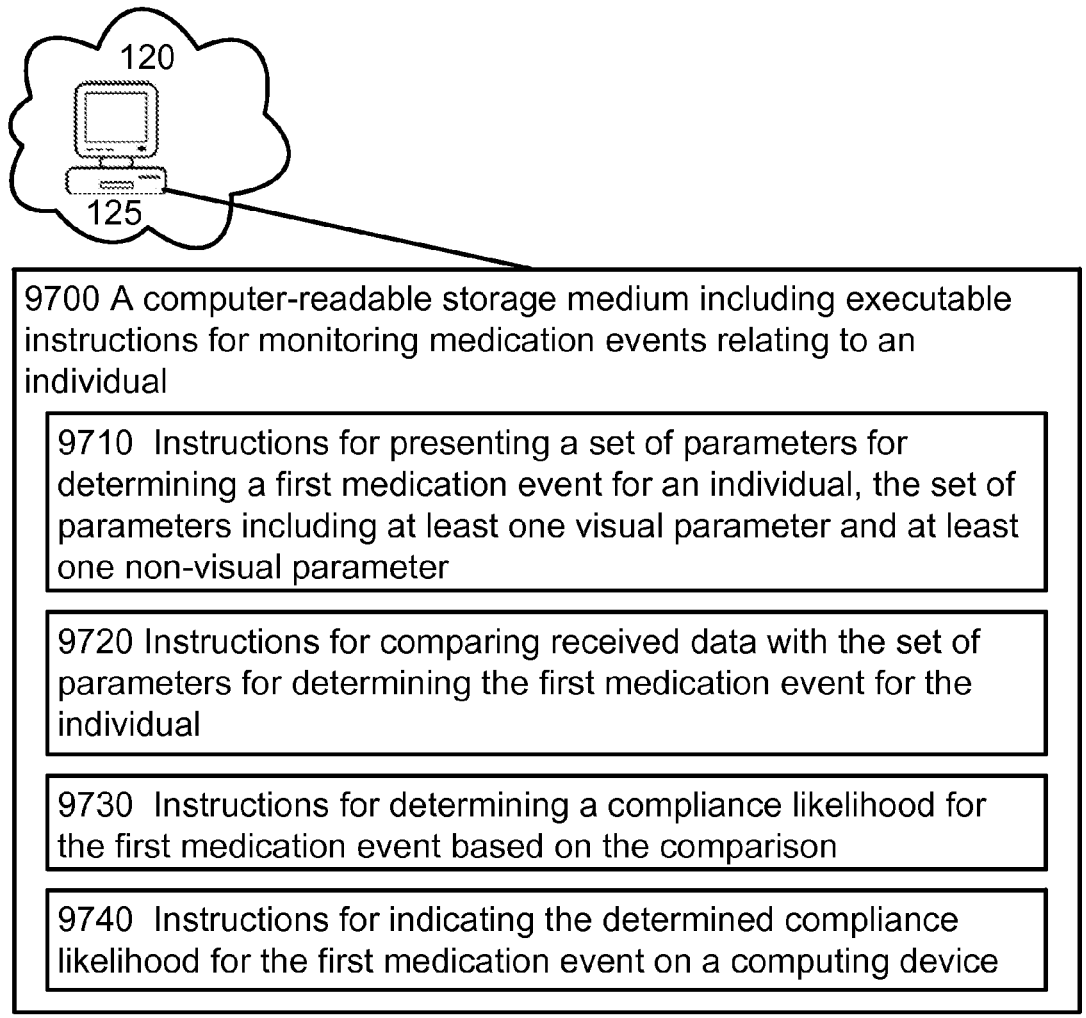
FIG. 97 depicts a system including computer-readable storage medium including executable instructions for monitoring medication events.

FIG. 97 illustrates aspects of a computer system 120 including at least one main computing unit 125. Although a single main computing unit 125 is illustrated in FIG. 97, in some embodiments there may be a plurality of main computing units 125. A main computing unit 125 includes computer-readable storage medium including executable instructions for monitoring medication events 9700. The computer-readable storage medium including executable instructions for monitoring medication events relating to an individual 9700 includes instructions 9710, 9720, 9730, 9740. Instructions 9710 include instructions for presenting a set of parameters for determining a first medication event for an individual, the set of parameters including at least one visual parameter and at least one non-visual parameter. Instructions 9720 include instructions for comparing received data with the set of parameters for determining the first medication event for the individual. Instructions 9730 include instructions for determining a compliance likelihood for the first medication event based on the comparison. Instructions 9740 include instructions for indicating the determined compliance likelihood for the first medication event on a computing device.

As shown in FIG. 97, instructions 9710 include instructions for presenting a set of parameters for determining a first medication event for an individual, the set of parameters including at least one visual parameter and at least one non-visual parameter. In some embodiments, instructions 9710 can include one or more additional instructions. For example, instructions 9710 can include instructions wherein the parameters include: at least one visual parameter specific to the individual; at least one visual parameter specific to a medication; at least one non-visual parameter specific to the individual; and at least one non-visual parameter specific to the medication.

In some embodiments, the computer-readable storage medium including executable instructions for monitoring medication events relating to an individual 9700 includes additional instructions as well as instructions 9710, 9720, 9730, 9740. For example, in some embodiments the instructions include instructions for saving the determined compliance likelihood into a memory. For example, in some embodiments the instructions include instructions for saving the determined compliance likelihood into a medical record for the individual. For example, in some embodiments the instructions include instructions for initiating a transmission including the determined compliance likelihood. For example, in some embodiments the instructions include instructions for saving the received data into a memory.

FIG. 98 depicts a flowchart of a method 9800 for monitoring medication events. These method steps can be carried out, for example, by a computer system (e.g. item 120 in FIG. 1). FIG. 98 shows that the method includes a series of steps, 9810, 9820, 9830, 9840. Method step 9810 includes presenting a set of parameters for determining a first medication event for an individual, the set of parameters including at least one visual parameter and at least one non-visual parameter. Method step 9820 includes comparing received data with the set of parameters for determining the first medication event for the individual. Method step 9830 includes determining a compliance likelihood for the first medication event based on the comparison. Method step 9840 includes indicating the determined compliance likelihood for the first medication event on a computing device.

In some embodiments, the method 9800 can include additional steps. For example, in some embodiments the set of parameters including at least one visual parameter and at least one non-visual parameter of method step 9810 includes: at least one visual parameter specific to the individual; at least one visual parameter specific to a medication; at least one non-visual parameter specific to the individual; and at least one non-visual parameter specific to the medication.

In some embodiments, the method 9800 can include further steps as well as the method steps 9810, 9820, 9830, 9840 illustrated in FIG. 98. For example, the method 9800 can include saving the determined compliance likelihood into a memory. For example, the method 9800 can include saving the determined compliance likelihood into a medical record for the individual. For example, the method 9800 can include initiating a transmission including the determined compliance likelihood. For example, the method 9800 can include saving the received data into a memory.

FIG. 99 illustrates further aspects of the systems and methods described herein. FIG. 99 illustrates aspects of a system for monitoring medication events relating to an individual. The system can be a computer system such as depicted in FIG. 1 and described herein. The system 9900 depicted in FIG. 99 includes electrical circuitry. The circuitry of the system 9900 is configured to carry out a series of logical processes. As illustrated in FIG. 99, a system 9900 for monitoring medication events relating to an individual includes one or more circuitry components 9910, 9920, 9930, 9940. The circuitry is configured to carry out specific processes.

The system 9900 includes circuitry 9910 for presenting a set of parameters for determining a first medication event for an individual, the set of parameters including at least one visual parameter and at least one non-visual parameter. The system 9900 includes circuitry 9920 for comparing received data with the set of parameters for determining the first medication event for the individual. The system 9900 includes circuitry 9930 for determining a compliance likelihood for the first medication event based on the comparison. The system 9900 includes circuitry 9940 for indicating the determined compliance likelihood for the first medication event on a computing device.

FIG. 99 also shows that, in some embodiments, the system 9900 includes additional aspects. For example, FIG. 99 shows that, in some embodiments, circuitry 9910 for presenting a set of parameters for determining a first medication event for an individual, the set of parameters including at least one visual parameter and at least one non-visual parameter includes circuitry 9950. Circuitry 9950 includes: circuitry including at least one visual parameter specific to the individual; circuitry including at least one visual parameter specific to a medication; circuitry including at least one non-visual parameter specific to the individual; and circuitry including at least one non-visual parameter specific to the medication.

FIG. 99 further depicts that, in some embodiments the system 9900 includes one or more additional aspects. For example, the system 9900 can include one or more of circuitry 9960, 9970, 9980, 9990. Circuitry 9960 includes circuitry for saving the determined compliance likelihood into a memory. Circuitry 9970 includes circuitry for saving the determined compliance likelihood into a medical record for the individual. Circuitry 9980 includes circuitry for initiating a transmission including the determined compliance likelihood. Circuitry 9990 includes circuitry for saving the received data into a memory.

FIG. 100 illustrates further aspects of the systems and methods described herein. FIG. 100 illustrates aspects of a system for monitoring medication events relating to an individual. The system can be a computer system such as depicted in FIG. 1 and described herein. The system 10000 depicted in FIG. 100 includes electrical circuitry. The circuitry of the system 10000 is configured to carry out a series of logical processes. As illustrated in FIG. 100, a system 10000 for monitoring medication events relating to an individual includes one or more circuitry components 10010, 10020, 10030, 10040, 10050, 10060. The circuitry is configured to carry out specific processes.

The system 10000 includes circuitry 10010 for determining a start of a medication event interval for an individual. The system 10000 includes circuitry 10020 for receiving data from at least one camera unit associated with the individual, the data including both visual data and non-visual data. The system 10000 includes circuitry presenting a set of parameters for determining a first medication event for an individual, the set of parameters including at least one visual parameter and at least one non-visual parameter. The system 10000 includes circuitry 10040 for comparing the received data with the set of parameters for determining the first medication event for the individual. The system 10000 includes circuitry 10050 for determining a compliance likelihood for the first medication event based on the comparison. The system 10000 includes circuitry 10060 for indicating the determined compliance likelihood for the first medication event.

FIG. 101 illustrates aspects of a computer system 120 including at least one main computing unit 125. Although a single main computing unit 125 is illustrated in FIG. 101, in some embodiments there may be a plurality of main computing units 125. A main computing unit 125 includes computer-readable storage medium including executable instructions for monitoring medication events 10100. The computer-readable storage medium including executable instructions for monitoring medication events relating to an individual 10100 includes instructions 10110, 10120, 10130, 10140. Instructions 10110 include instructions for determining a start of a medication event interval for an individual. Instructions 10120 include instructions for receiving data from at least one camera unit associated with the individual, the data including both visual data and non-visual data. Instructions 10130 include instructions for presenting a set of parameters for determining a first medication event for an individual, the set of parameters including at least one visual parameter and at least one non-visual parameter. Instructions 10140 include instructions for comparing the received data with the set of parameters for determining the first medication event for the individual. Instructions 10150 include instructions for determining a compliance likelihood for the first medication event based on the comparison. Instructions 10160 include instructions for indicating the determined compliance likelihood for the first medication event.

FIG. 102 illustrates a flowchart of a method 10200 for monitoring medication events relating to an individual. These method steps can be carried out, for example, by a computer system (e.g. item 120 in FIG. 1). FIG. 102 shows that the method includes a series of steps, 10210, 10220, 10230, 10240, 10250, 10260. Method step 10210 includes determining a start of a medication event interval for an individual. Method step 10220 includes receiving data from at least one camera unit associated with the individual, the data including both visual data and non-visual data. Method step 10230 includes presenting a set of parameters for determining a first medication event for an individual, the set of parameters including at least one visual parameter and at least one non-visual parameter. Method step 10240 includes comparing the received data with the set of parameters for determining the first medication event for the individual. Method step 10250 includes determining a compliance likelihood for the first medication event based on the comparison. Method step 10260 includes indicating the determined compliance likelihood for the first medication event. In some embodiments, additional method steps are included in the method.

A series of flowcharts depicting implementations are presented above. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. The style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, the style of presentation used herein also lends itself well to modular and/or object-oriented program design paradigms.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or a combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as a combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Examples of electro-mechanical systems include but are not limited to a variety of consumer electronics systems, medical devices, as well as other systems such as motorized transport systems, factory automation systems, security systems, and/or communication/computing systems. Electro-mechanical, as used herein, is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

At least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

With respect to the use of substantially any plural and/or singular terms herein, it is possible to translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components. In some instances, one or more components may be referred to herein as "configured to," "configured by," "configurable to," "operable/operative to," "adapted/adaptable," "able to," "conformable/conformed to," etc. Such terms (e.g. "configured to") can generally encompass active-state components and/or inactive-state components and/or standby-state components, unless context requires otherwise.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). When a specific number of an introduced claim recitation is intended, such an intent will be explicitly recited in the claim, and in the absence of such recitation no such intent is present. For example, as an aid to understanding, the following appended claims contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the above (e.g., "a system having at least one of A, B, and C" would include but not be limited to systems that have A alone, B alone, C alone, A and B together, A and C together, B and C together, and/or A, B, and C together, etc.). In those instances where a construction analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The foregoing specific exemplary processes and/or devices and/or technologies are representative of more general processes and/or devices and/or technologies taught elsewhere herein, such as in the claims filed herewith and/or elsewhere in the present application.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent. The various aspects and embodiments disclosed herein are for purposes of illustration and are not intended to be limiting, with the true scope and spirit being indicated by the following claims.

What is claimed is:

1. A system for monitoring medication events, comprising:
    circuitry for accepting first data from a camera unit associated with an individual;
    circuitry for providing a set of medication intervention parameters for the individual;
    circuitry for comparing the accepted first data from the camera unit associated with the individual with the provided set of medication intervention parameters for the individual;
    circuitry for determining if the accepted first data is within the provided set of medication intervention parameters;
    circuitry for activating at least one indicator in response to the first determination;
    circuitry for accepting second data from the camera unit associated with the individual, the second data obtained after the activation of the at least one indicator;
    circuitry for analyzing the accepted second data for at least one attribute relating to the medication event;
    circuitry for comparing the accepted second data with the provided set of medication intervention parameters for the individual;
    circuitry for determining if the accepted second data is within the provided set of medication intervention parameters; and
    circuitry for activating the at least one indicator in response to the second determination.

2. The system of claim 1, wherein the circuitry for accepting first data from the camera unit associated with the individual comprises:
    circuitry for accepting visual data and accepting non-visual data.

3. The system of claim 1, wherein the circuitry for accepting first data from the camera unit associated with the individual comprises:
    circuitry for accepting data including audio data.

4. The system of claim 1, wherein the circuitry for providing the set of medication intervention parameters for the individual comprises:
    circuitry for providing the set of medication intervention parameters for the individual including audio parameters.

5. The system of claim 1, wherein the circuitry for comparing the accepted first data from the camera unit associated with the individual with the provided set of medication intervention parameters for the individual comprises:
    circuitry for comparing the accepted first data with at least one minimum sufficiency parameter.

6. The system of claim 1, wherein the circuitry for accepting second data from the camera unit associated with the individual, the second data obtained after the activation of the at least one indicator, comprises:
    circuitry for accepting data including visual data, non-visual data, and at least one time value.

7. The system of claim 1, wherein the circuitry for analyzing the accepted second data for at least one attribute relating to a medication event comprises:
    circuitry for analyzing the accepted second data for at least one non-visual attribute.

8. The system of claim 1, comprising:
    circuitry for accepting third data from the camera unit associated with the individual, the third data obtained after the activation of the at least one indicator in response to the second determination;
    circuitry for analyzing the accepted third data for the at least one attribute relating to the medication event;
    circuitry for comparing the accepted third data with the provided set of medication intervention parameters for the individual;
    circuitry for determining if the accepted third data is within the provided set of medication intervention parameters; and
    circuitry for activating the at least one indicator in response to the third determination.

9. A computer-readable storage medium including executable instructions for monitoring medication events, the computer-readable storage medium comprising:
    instructions for accepting first data from a camera unit associated with an individual;
    instructions for providing a set of medication intervention parameters for the individual;
    instructions for comparing the accepted first data from the camera unit associated with the individual with the provided set of medication intervention parameters for the individual;
    instructions for determining if the accepted first data is within the provided set of medication intervention parameters;
    instructions for activating at least one indicator in response to the first determination;
    instructions for accepting second data from the camera unit associated with the individual, the second data obtained after the activation of the at least one indicator;
    instructions for analyzing the accepted second data for at least one attribute relating to the medication event;
    instructions for comparing the accepted second data with the provided set of medication intervention parameters for the individual;

instructions for determining if the accepted second data is within the provided set of medication intervention parameters; and instructions for activating the at least one indicator in response to the second determination.

10. The computer-readable storage medium of claim 9, wherein the instructions for accepting first data from the camera unit associated with the individual comprises:

instructions for accepting visual data and accepting non-visual data.

11. The computer-readable storage medium of claim 9, wherein the instructions for accepting first data from the camera unit associated with the individual comprises:

instructions for accepting data including audio data.

12. The computer-readable storage medium of claim 9, wherein the instructions for providing the set of medication intervention parameters for the individual comprises:

instructions for providing the set of medication intervention parameters for the individual including audio parameters.

13. The computer-readable storage medium of claim 9, wherein the instructions for comparing the accepted first data from the camera unit associated with the individual with the provided set of medication intervention parameters for the individual comprises:

instructions for comparing the accepted first data with at least one minimum sufficiency parameter.

14. The computer-readable storage medium of claim 9, wherein the instructions for accepting second data from the camera unit associated with the individual, the second data obtained after the activation of the at least one indicator, comprises:

instructions for accepting data including visual data, non-visual data, and at least one time value.

15. The computer-readable storage medium of claim 9, wherein the instructions for analyzing the accepted second data for the at least one attribute relating to the medication event comprises:

instructions for analyzing the accepted second data for at least one non-visual attribute.

16. The computer-readable storage medium of claim 9, comprising:

instructions for accepting third data from the camera unit associated with the individual, the third data obtained after the activation of the at least one indicator in response to the second determination;

instructions for analyzing the accepted third data for the at least one attribute relating to the medication event;

instructions for comparing the accepted third data with the provided set of medication intervention parameters for the individual;

instructions for determining if the accepted third data is within the provided set of medication intervention parameters; and instructions for activating the at least one indicator in response to the third determination.

17. A system for monitoring medication events, comprising:

circuitry for providing a set of attributes for an individual, the set of attributes identifiable in camera unit data;

circuitry for providing a set of medication condition parameters for the individual, the set of medication condition parameters identifiable in the camera unit data;

circuitry for accepting first data from at least one camera unit;

circuitry for comparing the accepted first data with the provided set of attributes for the individual and with the provided set of medication condition parameters for the individual;

circuitry for determining, from the comparison, if the accepted first data includes attributes of the individual and meets the medication condition parameters;

circuitry for initiating a first medication intervention event, dependent on the determination from the comparison;

circuitry for accepting second data from the at least one camera unit;

circuitry for providing a set of parameters for the first medication intervention event, the set of first medication intervention parameters identifiable in the camera unit data;

circuitry for comparing the accepted second data with the provided set of attributes for the individual and with the provided set of parameters for the first medication intervention event;

circuitry for determining, from the comparison, if the accepted second data includes attributes of the individual and meets the parameters for the first medication intervention event; and circuitry for activating at least one indicator in response to the second determination.

18. The system of claim 17, wherein the circuitry for providing the set of attributes for the individual, the set of attributes identifiable in the camera unit data, comprises:

circuitry for providing visual attributes; and
circuitry for providing non-visual attributes.

19. The system of claim 17, wherein the circuitry for providing the set of attributes for the individual, the set of attributes identifiable in the camera unit data, comprises:

circuitry for providing a set of attributes identifiable in the camera unit data including video data.

20. The system of claim 17, wherein the circuitry for providing the set of attributes for the individual, the set of attributes identifiable in the camera unit data, comprises:

circuitry for providing a set of attributes identifiable in the camera unit data including audio data.

21. The system of claim 17, wherein the circuitry for providing the set of medication condition parameters for the individual, the set of medication condition parameters identifiable in the camera unit data, comprises:

circuitry for providing a set of parameters including audio parameters.

22. The system of claim 17, wherein the circuitry for accepting the first data from the at least one camera unit comprises:

circuitry for accepting both visual and non-visual data.

23. The system of claim 17, wherein the circuitry for accepting first data from at least one camera unit comprises:

circuitry for accepting audio data.

24. The system of claim 17, wherein the circuitry for comparing the accepted first data with the provided set of attributes for the individual and with the provided set of medication condition parameters for the individual comprises:

circuitry for comparing visual and non-visual components of the accepted first data with the provided set of medication condition parameters for the individual and with the provided set of medication condition parameters for the individual.

25. The system of claim 17, wherein the circuitry for determining, from the comparison, if the accepted first data includes attributes of the individual and meets the medication condition parameters, comprises:

circuitry for determining, from the comparison, if the accepted first data meets both visual and non-visual aspects of the medication condition parameters.

26. The system of claim 17, comprising:
circuitry for processing the at least one accepted first data;
circuitry for processing the at least one accepted second data;
circuitry for integrating the processed at least one accepted first data and the processed at least one accepted second data into a medication record; and
circuitry for saving the medication record in a memory.

27. The system of claim 17, comprising:
circuitry for indicating, to at least one system user, the initiating a first medication intervention event.

28. A computer-readable storage medium including executable instructions for monitoring medication events, the computer-readable storage medium comprising:
instructions for providing a set of attributes for an individual, the set of attributes identifiable in camera unit data;
instructions for providing a set of medication condition parameters for the individual, the set of medication condition parameters identifiable in camera unit data;
instructions for accepting first data from at least one camera unit;
instructions for comparing the accepted first data with the provided set of attributes for the individual and with the provided set of medication condition parameters for the individual;
instructions for determining, from the comparison, if the accepted first data includes attributes of the individual and meets the medication condition parameters;
instructions for initiating a first medication intervention event, dependent on the determination from the comparison;
instructions for accepting second data from the at least one camera unit;
instructions for providing a set of parameters for the first medication intervention event, the set of first medication intervention parameters identifiable in camera unit data;
instructions for comparing the accepted second data with the provided set of attributes for the individual and with the provided set of parameters for the first medication intervention event;
instructions for determining, from the comparison, if the accepted second data includes attributes of the individual and meets the parameters for the first medication intervention event; and
instructions for activating at least one indicator in response to the second determination.

29. The computer-readable storage medium of claim 28, wherein the instructions for providing the set of attributes for the individual, the set of attributes identifiable in the camera unit data, comprises:
instructions for providing visual attributes; and
instructions for providing non-visual attributes.

30. The computer-readable storage medium of claim 28, wherein the instructions for providing the set of attributes for the individual, the set of attributes identifiable in the camera unit data, comprises:
instructions for providing a set of attributes identifiable in camera unit data including video data.

31. The computer-readable storage medium of claim 28, wherein the instructions for providing the set of attributes for an individual, the set of attributes identifiable in the camera unit data, comprises:
instructions for providing a set of attributes identifiable in camera unit data including audio data.

32. The computer-readable storage medium of claim 28, wherein the instructions for providing the set of medication condition parameters for the individual, the set of medication condition parameters identifiable in the camera unit data, comprises:
instructions for providing a set of parameters including audio parameters.

33. The computer-readable storage medium of claim 28, wherein the instructions for accepting the first data from the at least one camera unit comprises:
instructions for accepting audio data.

34. The computer-readable storage medium of claim 28, wherein the instructions for comparing the accepted first data with the provided set of attributes for the individual and with the provided set of medication condition parameters for the individual comprises:
instructions for comparing visual and non-visual components of the accepted first data with the provided set of medication condition parameters for the individual and with the provided set of medication condition parameters for the individual.

35. The computer-readable storage medium of claim 28, wherein the instructions for determining, from the comparison, if the accepted first data includes attributes of the individual and meets the medication condition parameters, comprises:
instructions for determining, from the comparison, if the accepted first data meets both visual and non-visual aspects of the medication condition parameters.

36. The computer-readable storage medium of claim 28, comprising:
instructions for processing the at least one accepted first data;
instructions for processing the at least one accepted second data;
instructions for integrating the processed at least one accepted first data and the processed at least one accepted second data into a medication record; and
instructions for saving the medication record in a memory.

37. The computer-readable storage medium of claim 28, comprising:
instructions for indicating, to at least one system user, the initiating a first medication intervention event.

* * * * *